US005595733A

United States Patent [19]

Carswell et al.

[11] Patent Number: 5,595,733

[45] Date of Patent: Jan. 21, 1997

[54] METHODS FOR PROTECTING ZEA MAYS PLANTS AGAINST PEST DAMAGE

[75] Inventors: Gleta Carswell, Cary; Christian Harms, Chapel Hill, both of N.C.; Yin-Fu Chang, Hayward, Calif.; Mary-Dell Chilton, Raleigh, N.C.

[73] Assignee: Ciba-Geigy Corporation, Tarrytown, N.Y.

[21] Appl. No.: 445,526

[22] Filed: May 22, 1995

Related U.S. Application Data

[62] Division of Ser. No. 269,677, Jul. 1, 1994, which is a continuation of Ser. No. 24,875, Mar. 1, 1993, Pat. No. 5,350,689, which is a continuation of Ser. No. 276,210, Nov. 23, 1988, abandoned, which is a continuation-in-part of Ser. No. 178,170, Apr. 6, 1988, abandoned, which is a continuation-in-part of Ser. No. 56,552, May 29, 1987, abandoned, and Ser. No. 56,506, May 29, 1987, abandoned, which is a continuation-in-part of Ser. No. 53,241, May 22, 1987, abandoned, which is a continuation-in-part of Ser. No. 52,440, May 20, 1987, abandoned.

[51] Int. Cl.$^6$ ............... A01N 65/00; C12N 5/04; C12N 5/14

[52] U.S. Cl. ................ 424/93.21; 536/23.71; 800/205

[58] Field of Search ............ 424/93.2, 93.461, 424/93.21; 800/205, 250, DIG. 56; 435/172.3, 172.1

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,665,030 | 5/1987 | Close | 435/240 |
| 4,666,844 | 5/1987 | Cheng | 435/240 |
| 4,684,611 | 8/1987 | Schilperoort et al. | 435/172.3 |
| 4,806,483 | 2/1989 | Wang | 435/240 |
| 4,820,639 | 4/1989 | Gehrke | 435/68 |
| 4,830,966 | 5/1989 | Close | 435/240 |
| 4,999,299 | 3/1991 | Shillito et al. | 435/240 |
| 5,049,500 | 9/1991 | Arnizen et al. | 435/172.3 |
| 5,164,310 | 11/1992 | Smith et al. | 435/172.3 |
| 5,177,010 | 1/1993 | Goldman et al. | 435/172.3 |
| 5,177,308 | 1/1993 | Barton et al. | 800/205 |
| 5,187,073 | 2/1993 | Golman et al. | 435/172.3 |
| 5,231,019 | 7/1993 | Paszkowski et al. | 435/172.3 |
| 5,254,799 | 10/1993 | De Greve et al. | 800/205 |
| 5,350,689 | 9/1994 | Shillito et al. | 435/240.47 |
| 5,371,003 | 12/1994 | Murry et al. | 435/172.3 |
| 5,380,831 | 1/1995 | Adang et al. | 536/23.71 |
| 5,384,253 | 1/1995 | Krzyzek et al. | 435/172.3 |
| 5,484,956 | 1/1996 | Lundquist et al. | 800/205 |
| 5,489,520 | 2/1996 | Adams et al. | 435/172.3 |
| 5,500,365 | 3/1996 | Fischhoff et al. | 435/240.4 |

FOREIGN PATENT DOCUMENTS

| | | |
|---|---|---|
| 0086537 | 8/1983 | European Pat. Off. . |
| 0140556 | 5/1985 | European Pat. Off. . |
| 0142924 | 5/1985 | European Pat. Off. . |
| 0160390 | 11/1985 | European Pat. Off. . |
| 0164575 | 12/1985 | European Pat. Off. . |
| 0174791 | 3/1986 | European Pat. Off. . |
| 0177738 | 4/1986 | European Pat. Off. . |
| 0193259 | 9/1986 | European Pat. Off. . |
| 0202739 | 11/1986 | European Pat. Off. . |
| 0213818 | 3/1987 | European Pat. Off. . |
| 0223247 | 5/1987 | European Pat. Off. . |
| 0243533 | 11/1987 | European Pat. Off. . |
| 0257472 | 3/1988 | European Pat. Off. . |
| 0290395 | 11/1988 | European Pat. Off. . |
| 0292435 | 11/1988 | European Pat. Off. . |
| 0317511 | 5/1989 | European Pat. Off. . |
| 0359472 | 3/1990 | European Pat. Off. . |
| 0465875 | 1/1992 | European Pat. Off. . |
| 0469273 | 2/1992 | European Pat. Off. . |
| 0574356 | 12/1993 | European Pat. Off. . |
| 62-129207 | 6/1987 | Japan . |
| 62-239994 | 10/1987 | Japan . |
| 63-137684 | 6/1988 | Japan . |
| 287485 | 11/1988 | Japan . |
| 2140822 | 12/1984 | United Kingdom . |
| 2183660 | 11/1985 | United Kingdom . |
| WO83/01176 | 4/1983 | WIPO . |
| WO85/01856 | 5/1985 | WIPO . |
| WO85/04899 | 11/1985 | WIPO . |
| WO86/01536 | 3/1986 | WIPO . |
| WO86/03776 | 7/1986 | WIPO . |
| WO87/00551 | 1/1987 | WIPO . |
| WO91/02071 | 2/1991 | WIPO . |
| WO93/07278 | 4/1993 | WIPO . |

OTHER PUBLICATIONS

Ammirato, P. V., "Chapter 3. Embryogenesis," in *Handbook of Plant Cell Culture. vol. 1, Techniques for Propagation and Breeding*, Evans et al., eds., MacMillan Publishing Co., New York, pp. 82–123 (1983).

Bryant, J. A., "Transformation of Monocot Plants by the Ti Plasmid of *Agrobacterium*," *Trends in Biotechnology* 3(1):21 (1985).

Bytebier, B., et al., "T–DNA Organization in Tumor Cultures and Transgenic Plants of the Monocotyledon *Asparagus officinalis*," *Proc. Natl. Acad. Sci USA*. 84:5345–5349 (Aug. 1987).

Christou, P., et al., "Opine Synthesis in Wild–Type Plant Tissue," *Plant Physiol.* 82:218–221 (Sep. 1986).

de Wet, J. M. J., et al., "Gametophyte Transformation in Maize (*Zea mays*, Gramineae)," ILLUS ISBN 0–387–96267–0, pp. 59–64 (1986).

French, R., et al., "Bacterial Gene Inserted in an Engineered RNA Virus: Efficient Expression in Monocotyledonous Plant Cells," *Science* 231:1294–1297 (Mar. 1986).

Goodman, R. M., et al., "Gene Transfer in Crop Improvement," *Science* 236:48–54 (Apr. 1987).

(List continued on next page.)

*Primary Examiner*—Gary Benzion
*Attorney, Agent, or Firm*—Sterne, Kessler, Goldstein & Fox P.L.L.C.

[57] ABSTRACT

According to the invention there is provided a method of controlling insect larvae comprising the steps of feeding said larvae an insecticidal amount of a transgenic *Zea mays* plant that expresses a polypeptide having the insect toxicity properties of *Bacillus thuringiensis* crystal protein.

4 Claims, 27 Drawing Sheets

OTHER PUBLICATIONS

Graves, A. C. F., and Goldman, S. L., "*Agrobacterium tumefaciens*–Mediated Transformation of the Monocot Genus Gladiolus : Detection of Expression of T–DNA–Encoded Genes," *J. Bacteriol.* 169 (4):1745–1746 (Apr. 1987).

Green, C. E., "Somatic Embryogenesis and Plant Regeneration from the Friable Callus of *Zea mays*," *Proc. 5th Intl. Cong. Plant Tissue and Cell Culture*, pp. 107–108 (1982).

Green, C. E., and Rhodes, C. A., "Plant Regeneration in Tissue Cultures of Maize," in: *Maize for Biological Research*, University Press, University of North Dakota, Grand Forks, ND, pp. 367–372 (1982).

Harms, C. T., et al., "Regeneration of Plantlets from Callus Cultures of *Zea mays* L.," *Z. pflanzenzüchtg.* 77: 347–351 (1976).

Hauptmann, R. M., et al., "Transient Expression of Electroporated DNA in Monocotyledonous and Dicotyledonous Species," *Plant Cell Reports* 6:265–270 (Jul. 1987).

Hepher, A., et al., "Microinjection of DNA into Pollen, Ovaries and Somatic Cells," (Conference Paper), ILLUS ISBN 90–247–3131–3–32–33 (1985).

Hernalsteens, J.–P., et al., "An Agrobacterium–Transformed Cell Culture From the Monocot *Asparagus officinalis*," *EMBO J.* 3(13):3039–3041 (1984).

Hodges, T. K., et al., "Genotype Specificity of Somatic Embryogenesis and Regeneration in Maize," *Bio/Technology* 4:219–223 (Mar. 1986).

Junker, B., et al., "Transient Expression of Chimaeric Genes in Dividing and Non–Dividing Cereal Protoplasts After PEG–Induced DNA Uptake," *Plant Cell Reports* 6:329–332 (Oct. 1987).

Kamo, K. K., et al., "Embryogenic Callus Formation From Maize Protoplasts," *Planta* 172:245–251 (Oct. 1987).

Kordyum, V. A., et al., "Transfer of dominant Allel [sic] of the Gene $Su_1$ in Maize by Means of Exogenous DNA," *Dopov. Akad. Nauk Ukr. Rsr Ser. B. Geol. Geofiz. Khim. Biol.* 36(8):759–762 (1974).

Korohoda, J., and Strzalka, K., "High Efficiency Genetic Transformation in Maize Induced by Exogenous DNA," *Z. pflanzenphysiol. Bd.* 94 (S):95–99 (1979).

Lehman, P., and Nebiolo, C. M., "The Degree of Degradation of the *Agrobacterium tumefaciens* Ti Plasmid in *Zea mays* and *Phaseolus vulgaris* Protoplasts," *Proc. Penn. Acad. Sci.* 59(10):80 (1985).

Sheridan, W. F., "Tissue Culture of Maize. I. Callus Induction and Growth," *Physiol. Plant* 33:151–156 (1975).

Vasil, I. K., and Vasil, V., "Chapter 6. Regeneration in Cereal and Other Grass Species," in: *Cell Culture and Somatic Cell Genetics of Plants, vol. 3: Plant Regeneration and Genetic Variability*, I. K. Vasil, ed., Academic Press, Inc., Orlando, FL, pp. 121–150 (1986).

Welter, M. E., et al., "Morphotypes of Friable Embryogenic Maize Callus," *Plant Cell Reports* 14:725–729 (1995).

Werr, W., and Lörz, H., "Transient Gene Expression In a Gramineae Cell Line. A Rapid Procedure for Studying Plant Promoters," *Mol. Gen. Genet.* 202:471–475 (Mar. 1986).

English Abstract for Japanese Patent Document Number JP62–239994 (reference AM6), Derwent World Patent Index Accession No. 87–332762/47.

Armstrong et el., "Factors affecting PEG–mediated stable transformation of maize protoplasts", *Plant Cell Reports* 9:335–339 (1990).

Barton et el., "*Bacillus thuringiensis* δ–endotoxin expressed in transgenic *Nicotiana tabacum* provides resistance to lipidopteran insects", *Plant Physiol.* 85:1103–1109 (1987).

Bevan et el., "A chimaeric antibiotic resistance gene as a selectable marker for plant cell transformation", *Nature* 304:184–187 (Jul. 14, 1983).

Bevan, "Binary *Agrobacterium* vectors for plant transformation", *Nucleic Acids Research* 12(22) :8711–8721 (1984).

Birk et al., "Separation of a tribolium–protease inhibitor from soybeans on a calcium phosphate column", *Biochim. Biophys. Acta* 67:326–328 (1963).

Brown, "The morphology of the grass embryo", *Phytomorphology* 10:215–223 (Oct. 1960).

Brown et al., "RFLP analysis of *Zea mays* callus cultures and their regenerated plants", *Theor. Appl. Genet.* 81:227–232 (1991).

Bruneau, "In vitro regeneration from immature embryo callus in maize: quantitative aspects and transmission through crosses", *Agronomie* 5(7) :591–596 (1985), Summary Only in English.

Callis et al., "Introns increase gene expression in cultured maize cells ", *Genes and Dev.* 1:1183–1200 (1987).

Carswell et al., "O–acetyl–salicylic acid promotes colony formation from protoplasts of an elite maize inbred", *Plant Cell Reports* 8:282–284 (1989).

Chang, "Plant regeneration in vitro from leaf tissues derived from cultured immature embryos of *Zea mays*", *Plant Cell Reports* 2:183–185 (1983).

Chih–ching, "The $N_6$ medium and its applications to another culture of cereal crops", *Proc. Symp. on Plant Tissue Culture*, hulton (Ed.), Peking, pp. 43–50 (1978).

Chourey et al, "Callus formation from protoplasts of a maize cell culture", *Theor. Appl. Genet.* 59:341–344 (1981).

Covey et al., "Characterization of cauliflower mosaic virus DNA sequences which encode major polyadenylated transcripts", *Nucleic Acids Research* 9(24):6735–6747 (1981).

Dale, "Protoplast culture and plant regeneration of cereals and other recalcitrant crops", *In: Lecture Proceedings, Experientia Supplementum* 46, Potrykus et al. (Eds.), Birkhauser, Basel, pp. 31–41 (1983).

Datta et al., "Genetically engineered fertile indica–rice recovered from protoplasts", *Bio/Technology* 8:736–740 (1990).

Ding et al., "Identification of an effective vector constructed for maize transformation and study of PEG–mediated transformation method", *Science in China (Series B)* 35(10):1187–1195 (Oct., 1992).

Ditta et al., "Broad host range DNA cloning system for gram–negative bacteria: construction of a gene bank of *Rhizobium meliloti*", *Proc. Natl. Acad. Sci. USA* 77(12):7347–7351 (Dec. 1980).

Duncan et al., "The production of callus capable of plant regeneration from immature embryos of numerous *Zea mays* genotypes", *Planta* 165:322–332 (1985).

Falco et al., "Nucleotide sequence of the yeast ILV2 gene which encodes acetolactate synthase", *Nucleic Acids Research.* 13 (11) :4011–4027 (1985).

Feldmann and Marks, "Rapid and efficient regeneration of plants from explants of *Arabidopsis thaliana*", *Plant Science* 47:63–69 (1986).

Franck et al., "Nucleotide sequence of cauliflower mosaic virus DNA", *Cell* 21:285–294 (1980).

Fromm et al., "Expression of genes transferred into monocot and dicot plant cells by electroporation", *Proc. Natl. Acad. Sci. USA* 82:5824–5828 (1985).

Fromm et al., "Inheritance and expression of chimeric genes in the progeny of transgenic maize plants", *Bio/Technology* 8:833–839 (1990).

Fromm et al., "Stable transformation of maize after gene transfer by electroporation", *Nature* 319:791–793 (Feb. 27, 1986).

Gallie et al., "The 5'-leader sequence of tobacco mosaic virus RNA enhances the expression of foreign gene transcripts in vitro and in vivo", *Nucleic Acids Research* 15(8):3257–3273 (1987).

Geiser et al., "The hypervariable region in the genes coding for entomopathogenic crystal proteins of *Bacillus thuringiensis*: nucleotide sequence of the *kurhd1* gene of subsp. *kurstaki* HD1, *Gene* 48:109–118 (1986).

Gordon-Kamm et al., "Transformation of maize cells and regeneration of fertile transgenic plants", *The Plant Cell* 2:603–618 (Jul. 1990).

Graves and Goldman, "The transformation of *Zea mays* seedlings with *Agrobacterium tumefaciens*", *Plant Molecular Biology* 7:43–50 (1986).

Green and Phillips, "Plant regeneration from tissue cultures of maize", *Crop Sc.* 15:417–421 (May–Jun. 1975).

Green, "Prospects for crop improvement in the field of cell culture", *HortScience* 12(2):131–134 (Apr. 1977).

Green and Armstrong, "Somatic cell genetic systems in corn", *Advances in Gene Technology: Molec. Genet. of Plants and Animals*, Downey et al. (Eds.), Academic Press, pp. 147–157 (1983).

Green et al., "Tissue Culture of Maize (Zea mays): Initiation, Maintainance, and Organic Growth Factors38, *Crop Science* 14:54–58 (1974).

Gritz and Davies, "Plasmid–encoded hygromycin B resistance: the sequence of hygromycin B phosphotransferase gene and its expression in *Escherichia coli* and *Saccharomyces cerevisiae*", *Gene* 25:179–188 (1983).

Hammond et al., "Molecular cloning and analysis of a gene coding for the Bowman–Birk protease inhibitor in soybean", *J. Biol. Chem.* 259(15):9883–9890 (Aug. 10, 1984).

Harms and Potrykus, "Fractionation of plant protoplast types by iso–osmotic density gradient centrifugation", *Theor. Appl. Genet.* 53:57–63 (1978).

Hilder et al., "A novel mechanism of insect resistance engineered into tobacco", *Nature* 330:160–163 (Nov. 12, 1987).

Hohn et al., "Cauliflower mosaic virus on its way to becoming a useful plant vector", *Current Topics in Microbiology and Immunology* 96:193–236 (1982).

Hollingshead and Vapnek, "Nucleotide sequence analysis of a gene encoding a streptomycin/spectinomycin adenyltransferase", *Plasmid* 13:17–30 (1985).

Hood et al., "The hypervirulence of *Agrobacterium tumefaciens* A281 is encoded in a region of pTiBo542 outside of T–DNA", *J. Bacteriol.* 168(3):1291–1301 (Dec. 1986).

Hood et al., "Restriction endonuclease map of pTi Bo542, a potential Ti plasmid vector for genetic engineering of plants", *Bio/Technology* 2:702–709 (Aug. 1984).

Imbrie–Milligan and Hodges, "Microcallus growth from maize protoplasts prepared from embryogenic callus", *Planta* 168:395–401 (1986).

Imbrie–Milligan et al., "Microcallus growth from maize protoplasts", *Chemical Abstracts* 107:3682, Abstract No. 3685r (1987).

Jacoby et al., "Recombination between plasmids of incompatibility groups P-1 and P-2", *J. Bacteriol.* 127(3):1278–1285 (Sep. 1976).

Jayos–Rios, "Effects of different phytohormonal treatments on the organogenesis of callus tissues of *Zea Mays*", *Annales des Sciences Naturelles*, Botanique, Paris 13 (7):55–62 (1985).

Jorgensen et al., "A restriction enzyme cleavage map of Tn5 and location of a region encoding neomycin resistance", *Molec. Gen. Genet.* 177:65–72 (1979).

Kamo and Hodges, "Establishment and characterization of long–term embryogenic maize callus and cell suspension cultures", *Plant Science* 45:111–117 (1986).

Kamo et al., "Regeneration of *Zea mays* L. from embryogenic callus", *Botanical Gazette* 146(3):327–334 (1985).

Kim et al., "Lodging Disease, and Insect Resistant, and High Yielding Maize Hybrid 'Suweon 21'", Res. Rep. of Rual Dev. (Suweon) 20 (Crop), pp. 163–168 (1979) (Abstract in English).

Klausner, "Microbial insect control using bugs to kill bugs", *Bio/Technology* 2:409–419 (May 1984).

Kreis et al., "Structure and evolution of seed storage proteins and their genes with particular reference to those of wheat, barley and rye", *Oxford Surveys of Plant Molecular & Cell Biology* 2:253–317 (1985).

Krens et al., "In vitro transformation of plant protoplasts with Ti–plasmid DNA", *Nature* 296:73–74 (Mar. 4, 1982).

Lee et al., "Isolation, culture and morphogenesis from wheat protoplasts, and study of expression of DNA constructs by direct gene transfer", *Plant Cell, Tissue and Organ Culture* 12:223–226 (1988).

Lipke et al., "Effect of soybean inhibitors on growth of *Tribolium confusum*", *Agricultural and Food Chemistry* 2:410–414 (1954).

Lloyd et al., "Transformation of *Arabidopsis thaliana* with *Agrobacterium tumefaciens*", *Science* 234:464–466 (Oct. 24, 1980).

Lörz et al., "Gene transfer to cereal cells mediated by protoplast transformation", *Mol. Gen. Genet.* 199:178–182 (1985).

Lowe et al., "Plant regeneration via organogenesis and embryogenesis in the maize inbred line B73", *Plant Science* 41:125–132 (1985).

Lu et al., "Isolation and Culture of Protoplasts of Panicum maximum Jacq. (Guinea Grass): Somatic Embryogenesis and Plantlet Formation," *Z. phlanzenphys. Bd.* 104:311–318 (1981).

Lu et al., "Improved efficiency of somatic embryogenesis and plant regeneration in tissue cultures of maize (*Zea mays*)", *Theor. Appl. Genet.* 66:285–289 (1983).

Lu et al., "Somatic embryogenesis in *Zea mays*", *Theor. Appl. Genet.* 62:109–112 (1982).

Ludwig et al., "High frequency callus formation from maize protoplasts", *Theor. Appl. Genet.* 71:344–350 (1985).

Lurquin, "Transfer of plasmid DNA to plant protoplasts. I. Conditions mimicking virus or viral nucleic acid infection", *Archives Interationales de Physiologie et de Biochemie* 87 (4):824–825 (1979).

Lyznik et al., "Stable co–transformation of maize 21 protoplasts with gusA and neo genes", *Plant Molecular Biology* 13:151–161 (1989).

Lyznik et al., "Stable transformation of maize: the impact of feeder cells on protoplast growth and transformation efficiency", *Plant Cell Reports* 8:292–295 (1989).

Mackey et al., "Transgenic Maize", in: *Transgenic Plants, Academic Press*, vol. 2:21–33 (1993).

Matzke and Chilton, "Site–specific insertion of genes into T–DNA of the Agrobacterium tumor–inducing plasmid: an approach to genetic engineering of higher plant cells", *J. Mol. Appl. Genet.* 1:39–49 (1981).

Miller et al., "Bacterial, viral, and fungal insecticides", *Science* 219:715–721 (Feb. 11, 1983).

Mitchell and Petolino, "Haploid suspension and protoplast culture from isolated microspores of maize", *Progress in Plant Cellular and Molec. Biol.*, Proceedings of the VIIth Intl. Cong. on Plant Tissue and Cell Culture, Nijkamp et al. eds., Kluwer Academic Publ., pp. 264–269 (1990).

Morelli et al., "A short conserved sequence is involved in the ligh–inducibility of a gene encoding ribulose 1,5–bisphosphate carboxylase small subunit of pea", *Nature* 315:200–204 (May 16, 1985).

Mórocz et al., "Plant regeneration from haploid and diploid *Zea mays* protoplast cultures", *Abstracts VIIth International Congress on Plant Tissue and Cell Culture*, Amsterdam, Abstract No. A1–102, Jun. 24–29, 1990.

Mrórocz et al., "An improved system to obtain fertile regenerants via maize protoplasts isolated from a highly embryogenic suspension culture", *Theor. Appl. Genet.* 80:721–726 (1990).

Negrutiu et al., "Hybrid genes in the analysis of transformation conditions", *Plant Mol. Biology* 8:363–373 (1987).

Ohta, "High–efficiency genetic transformation of maize by a mixture of pollen and exogenous DNA", *Proc. Natl. Acad. Sci. USA* 83:715–719 (Feb. 1986).

Omirulleh et al., "Activity of chimeric promoter with the doubled CaMV 35S enhancer element in protoplast–derived cells and transgenic plants in maize", *Plant Molecular Biology* 21:415–428 (1993).

Oka et al., "Nucleotide sequence at the insertion sites of a kanamycin transposon", *Nature* 276:845–847 (Dec. 21/28, 1978).

Oka et al., "Nucleotide sequence of the kanamycin resistance transposon Tn903", *J. Mol. Biol.* 147:217–226 (1981).

Pareddy and Petolino, "Somatic embryogenesis and plant regeneration from immature inflorescences of several elite inbreds of maize", *Plant Science* 67:211–219 (1990).

Paszkowski et al., "Direct gene transfer to plants", *EMBO Journal* 3(12):2217–2722 (1984).

Payne et al., "Isolation of the genomic clone for pathogenesis–related protein 1a from *Nicotiana tabacum cv.* Xanthi–nc", *Plant Molecular Biology* 11:89–94 (1988).

Petersen et al., "Effect of nurse cultures on the production of macro–calli and fertile plants from maize embryogenic suspension culture protoplasts", *Plant Cell Reports* 10:591–594 (1992).

Polaina, "Cloning of the ILV2, ILV3 and ILV5 genes of *Saccharomyces cerevisiae*", *Carlsberg Res. Commun.* 49:577–584 (1984).

Potrykus et al., "Callus formation from stem protoplasts of corn (*Zea mays*)", *Mol. Gen. Genet.* 156:347–350 (1977).

Potrykus et al., "Callus formation from cell culture protoplasts of corn (*Zea mays*)", *Theor. Appl. Genet.* 54:209–214 (1979).

Potrykus et al., "Problems in culturing cereal protoplasts", *Cell Genetics in Higher Plants*, Proceedings of an International Training Course, Dudits et al. (Eds.), Szeged, Hungary, pp. 129–140 (Jul. 5–17, 1976).

Potrykus et al., "Direct gene transfer to cells of a graminaceous monocot", *Mol. Gen. Genet.* 199:183–188 (1985).

Potrykus I., "Gene transfer to plants: Assessment of published approaches and results", *Annu. Rev. Plant Physiol. Plant Mol. Biol.* 42:205–225 (1991).

Prioli and Söndahl, "Plant regeneration and recovery of fertile plants from protoplasts of maize (*Zea mays*)," *Bio/Technology* 7:589–594 (Jun. 1989).

Radojević, "Tissue culture of maize *Zea mays* <<Cudu>>. I. Somatic embryogenesis in the callus tissue", *J. Plant Physiol.* 119:435–441 (1985).

Randolf, "Developmental morphology of the caryopsis in maize", *J. Agric. Research* 53(12):881–916 (Dec. 15, 1936).

Rapela, "Organogenesis and somatic embryogenesis in tissue cultures of Argentine maize (*Zea mays*)", *J. Plant Physiol.* 121:119–122 (1985).

Rhodes et al., "Factors affecting tissue culture initiation from maize tassels", *Plant Sci.* 46:225–232 (1986).

Rhodes et al., "Genetically transformed maize plants from protoplasts", *Science* 240:204–207 (1988).

Rhodes et al., "Plant regeneration from protoplasts isolated from embryogenic maize cell cultures", *Bio/Technology* 6:56–60 (1988).

Rothstein et al., "Promoter cassettes, antibiotic–resistance genes, and vectors for plant transformation", *Gene* 53:153–161 (1987).

Ryan, "Proteolytic enzymes and their inhibitors in plants", *Ann. Rev. Plant Physiol.* 24:173–196 (1973).

Sánchez de Jiménez et al., "Effect of 2,4–D analogues on the induction and maintenance of callus in maize tissue culture", *Ann. Appl. Biol.* 98:347–353 (1981).

Sanford et al., "Attempted pollen–mediated plant transformation employing genomic donor DNA", *Theor. Appl. Genet.* 69:571–574 (1985).

Saxena and Rashid, "Differentiation of bud–cells on the protonema of the moss *Anoectangium thomsonii*. Effect of aspirin and salicylic acid", *Z. pflanzenphysiol. Bd.* 99:187–189 (1980).

Saxena and Rashid, "Development of gametophores from isolated protoplasts of the moss *Anoectangium thomsonii*. Mitt.", *Protoplasma* 103:401–406 (1980).

Schenk and Hildebrandt, "Medium and techniques for induction and growth of monocotyledonous and dicotyledonous plant cell cultures", *Canadian Journal of Botany* 50:199–204 (1972).

Sciaky et al., "Fingerprints of Agrobacterium Ti plasmids", *Plasmid* 1:238–253 (1978).

Sekar et al., "Molecular cloning and characterization of the insecticidal crystal protein gene of *Bacillus thuringiensis* var. *tenebrionis*", *Proc. Natl. Acad. Sci. USA* 84: 7036–7040 (Oct. 1987).

Shaw and Kamen, "A conserved AU sequence from the 3' untranslated region of GM–CSF mRNA mediates selective mRNA degradation", *Cell* 46:659–667 (Aug. 29, 1986).

Sheikholeslam and Weeks, "Acetosyringone promotes high efficiency transformation of *Arabidopsis thaliana* explants by *Agrobacterium tumefaciens*", *Plant Molec. Biol.* 8:291–298 (1987).

Shillito et al., "Regeneration of fertile plants from protoplasts of elite inbred maize", *Bio/Technology* 7:581–587 (Jun. 1989).

Shillito et al., "High efficiency direct gene transfer to plants", *Bio/Technology* 3:1099–1103 (Dec. 1985).

Shinshi et al., "Regulation of a plant pathogenesis–related enzyme: inhibition of chitinase and chitinase mRNA accumulation in cultured tobacco tissues by auxin and cytokinin", *Proc. Natl. Acad. Sci. USA* 84:89–93 (1987).

Shneyour et al., "A simple feeder-layer technique for the plating of plant cells and protoplasts at low density", *Plant Science Lett.* 33:293–302 (1984).

Sleat et al., "Studies on the mechanism of translational enhancement by the 5'-leader sequence of tobacco mosaic virus RNA", *Eur. J. Biochem.* 175:75–86 (1988).

Smith et al., "Feeder layer support of low density populations of Zea mays L. suspension cells", *Plant Science Lett.* 36:67–72 (1984).

Sun et al., "Regeneration of haploid and dihaploid plants from protoplasts of supersweet (sh2sh2) corn", *Plant Cell Reports* 8:313–316 (1989).

Suprasanna et al., "Plantlet regeneration from glume calli of maize (Zea mays)", *Theor. Appl. Genet.* 72:120–122 (1986).

Thompson et al., "Characterization of the herbicide-resistance gene bar from Streptomyces hygroscopicus", *EMBO Journal* 6:2519–2523 (1987).

Tomes and Smith, "The effect of parental genotype on initiation of embryogenic callus from elite maize (Zea mays) germplasm", *Theor. Appl. Genet.* 70:505–509 (1985).

Tomé and Santos, "Aspects of totipotency in calli cultures of Zea mays: maintenance and variability of totipotent structures", *Inv. Agrar.: Prod. Prot. Veg.* 2(2):111–120 (1987).

Tomé et al., "Methods of obtaining maize totipotent tissues. II. Atrophic tissue culture", *Plant Science Letters* 33:317–325 (1984).

Treissman, "Transient accumulation of c–fos RNA following serum stimulation requires a conserved 5' element and c–Fos 3' sequences", *Cell* 42:889–902 (Oct. 1985).

Vaeck et al., "Transgenic plants protected from insect attack", *Nature* 328:33–37 (Jul. 2, 1987).

Vasil et al., "Plant Regeneration from Protoplasts of Napier Grass (Pennisetum purpureum Schum.)", *Z. pflanzenphys. Bd.* 111:233–239 (1983).

Vasil et al., "Proliferation and plant regeneration from the nodal region of Zea mays (maize, gramineae) embryos", *Amer. J. Bot.* 70(6):951–954 (1983).

Vasil, V. and Vasil, I. K., "Formation of callus and somatic embryos from protoplasts of a commercial hybrid of maize (Zea mays)", *Theor. Appl. Genet.* 73:793–798 (1987).

Vasil, V. and Vasil, I. K., "Isolation and culture of cereal protoplasts", *Theor. Appl. Genet.* 56:97–99 (1980).

Vasil, V. and Vasil, I. K., "Plant regeneration from friable embryogenic callus and cell suspension cultures of Zea mays", *J. Plant Physiol.* 124:399–408 (1986).

Wang, "Callus induction and plant regeneration from maize mature embryos", *Plant Cell Reports* 6:360–362 (1987).

Wong et al., "Transcriptional and translational start sites for the Bacillus thuringiensis crystal protein gene", *J. Biol. Chem.* 258(3):1960–1967 (Feb. 10, 1983).

Wullems et al., "The expression of tumour markers in intraspecific somatic hybrids of normal and crown gall cells from Nicotiana tabacum", *Theor. App. Genet.* 56:203–208 (1980).

Yadov et al., "Short direct repeats flank the T–DNA on a nopaline Ti plasmid", *Proc. Natl. Acad. Sci. USA* 79:6322–6326 (Oct. 1982).

Yamada and Sakaguchi, "Polyethylene glycol–induced uptake of bacteria into yeast protoplasts", *Agricultural and Biological Chemistry* 45 (10):2301–2369 (1981).

Zoller and Smith, "Oligonucleotide–directed mutagenesis: a simple method using two oligonucleotide primers and a single-stranded DNA template", *DNA* 3(6):479–488 (1984).

Fries L., "Induction of plantlets in axenically cultivated rhizoids of Fucus spiralis," *Can. J. Bot.* 62:1616–1620 (1983).

Declaration of Stephen V. Evola, signed Sep. 3, 1992.

```
  1 GTTAACACCC TGGGTCAAAA ATTGATATTT AGTAAAATTA GTTGCACTTT
 51 GTGCATTTTT TCATAAGATG AGTCATATGT TTTAAATTGT AGTAATGAAA
101 AACAGTATTA TATCATAATG AATTGGTATC TTAATAAAAG AGATGGAGGT
151 AACTTATGGA TAACAATCCG AACATCAATG AATGCATTCC TTATAATTGT
201 TTAAGTAACC CTGAAGTAGA AGTATTAGGT GGAGAAAGAA TAGAAACTGG
251 TTACACCCCA ATCGATATTT CCTTGTCGCT AACGCAATTT CTTTTGAGTG
301 AATTTGTTCC CGGTGCTGGA TTTGTGTTAG GACTAGTTGA TATAATATGG
351 GGAATTTTTG GTCCCTCTCA ATGGGACGCA TTTCTTGTAC AAATTGAACA
401 GTTAATTAAC CAAAGAATAG AAGAATTCGC TAGGAACCAA GCCATTTCTA
451 GATTAGAAGG ACTAAGCAAT CTTTATCAAA TTTACGCAGA ATCTTTTAGA
501 GAGTGGGAAG CAGATCCTAC TAATCCAGCA TTAAGAGAAG AGATGCGTAT
551 TCAATTCAAT GACATGAACA GTGCCCTTAC AACCGCTATT CCTCTTTTTG
601 CAGTTCAAAA TTATCAAGTT CCTCTTTTAT CAGTATATGT TCAAGCTGCA
651 AATTTACATT TATCAGTTTT GAGAGATGTT TCAGTGTTTG GACAAAGGTG
701 GGGATTTGAT GCCGCGACTA TCAATAGTCG TTATAATGAT TTAACTAGGC
751 TTATTGGCAA CTATACAGAT CATGCTGTAC GCTGGTACAA TACGGGATTA
801 GAGCGTGTAT GGGGACCGGA TTCTAGAGAT TGGATAAGAT ATAATCAATT
851 TAGAAGAGAA TTAACACTAA CTGTATTAGA TATCGTTTCT CTATTTCCGA
901 ACTATGATAG TAGAACGTAT CCAATTCGAA CAGTTTCCCA ATTAACAAGA
```

FIG.13A

```
 951 GAAATTTATA CAAACCCAGT ATTAGAAAAT TTTGATGGTA GTTTTCGAGG

1001 CTCGGCTCAG GGCATAGAAG GAAGTATTAG GAGTCCACAT TTGATGGATA

1051 TACTTAACAG TATAACCATC TATACGGATG CTCATAGAGG AGAATATTAT

1101 TGGTCAGGGC ATCAAATAAT GGCTTCTCCT GTAGGGTTTT CGGGGCCAGA

1151 ATTCACTTTT CCGCTATATG GAACTATGGG AAATGCAGCT CCACAACAAC

1201 GTATTGTTGC TCAACTAGGT CAGGGCGTGT ATAGAACATT ATCGTCCACT

1251 TTATATAGAA GACCTTTTAA TATAGGGATA AATAATCAAC AACTATCTGT

1301 TCTTGACGGG ACAGAATTTG CTTATGGAAC CTCCTCAAAT TTGCCATCCG

1351 CTGTATACAG AAAAAGCGGA ACGGTAGATT CGCTGGATGA AATACCGCCA

1401 CAGAATAACA ACGTGCCACC TAGGCAAGGA TTTAGTCATC GATTAAGCCA

1451 TGTTTCAATG TTTCGTTCAG GCTTTAGTAA TAGTAGTGTA AGTATAATAA

1501 GAGCTCCTAT GTTCTCTTGG ATACATCGTA GTGCTGAATT TAATAATATA

1551 ATTCCTTCAT CACAAATTAC ACAAATACCT TTAACAAAAT CTACTAATCT

1601 TGGCTCTGGA ACTTCTGTCG TTAAAGGACC AGGATTTACA GGAGGAGATA

1651 TTCTTCGAAG AACTTCACCT GGCCAGATTT CAACCTTAAG AGTAAATATT

1701 ACTGCACCAT TATCACAAAG ATATCGGGTA AGAATTCGCT ACGCTTCTAC

1751 CACAAATTTA CAATTCCATA CATCAATTGA CGGAAGACCT ATTAATCAGG

1801 GGAATTTTTC AGCAACTATG AGTAGTGGGA GTAATTTACA GTCCGGAAGC

1851 TTTAGGACTG TAGGTTTTAC TACTCCGTTT AACTTTTCAA ATGGATCAAG

1901 TGTATTTACG TTAAGTGCTC ATGTCTTCAA TTCAGGCAAT GAAGTTTATA
```

FIG.13B

```
1951  TAGATCGAAT TGAATTTGTT CCGGCAGAAG TAACCTTTGA GGCAGAATAT

2001  GATTTAGAAA GAGCACAAAA GGCGGTGAAT GAGCTGTTTA CTTCTTCCAA

2051  TCAAATCGGG TTAAAAACAG ATGTGACGGA TTATCATATT GATCAAGTAT

2101  CCAATTTAGT TGAGTGTTTA TCTGATGAAT TTTGTCTGGA TGAAAAAAAA

2151  GAATTGTCCG AGAAAGTCAA ACATGCGAAG CGACTTAGTG ATGAGCGGAA

2201  TTTACTTCAA GATCCAAACT TTAGAGGGAT CAATAGACAA CTAGACCGTG

2251  GCTGGAGAGG AAGTACGGAT ATTACCATCC AAGGAGGCGA TGACGTATTC

2301  AAAGAGAATT ACGTTACGCT ATTGGGTACC TTTGATGAGT GCTATCCAAC

2351  GTATTTATAT CAAAAAATAG ATGAGTCGAA ATTAAAAGCC TATACCCGTT

2401  ACCAATTAAG AGGGTATATC GAAGATAGTC AAGACTTAGA AATCTATTTA

2451  ATTCGCTACA ATGCCAAACA CGAAACAGTA ATGTGCCAG GTACGGGTTC

2501  CTTATGGCCG CTTTCAGCCC CAAGTCCAAT CGGAAAATGT GCCCATCATT

2551  CCCATCATTT CTCCTTGGAC ATTGATGTTG GATGTACAGA CTTAAATGAG

2601  GACTTAGGTG TATGGGTGAT ATTCAAGATT AAGACGCAAG ATGGCCATGC

2651  AAGACTAGGA AATCTAGAAT TTCTCGAAGA GAAACCATTA GTAGGAGAAG

2701  CACTAGCTCG TGTGAAAAGA GCGGAGAAAA AATGGAGAGA CAAACGTGAA

2751  AAATTGGAAT GGGAAACAAA TATTGTTTAT AAAGAGGCAA AAGAATCTGT

2801  AGATGCTTTA TTTGTAAACT CTCAATATGA TAGATTACAA GCGGATACCA

2851  ACATCGCGAT GATTCATGCG GCAGATAAAC GCGTTCATAG CATTCGAGAA

2901  GCTTATCTGC CTGAGCTGTC TGTGATTCCG GGTGTCAATG CGGCTATTTT
```

FIG.13C

2951 TGAAGAATTA GAAGGGCGTA TTTTCACTGC ATTCTCCCTA TATGATGCGA

3001 GAAATGTCAT TAAAAATGGT GATTTTAATA ATGGCTTATC CTGCTGGAAC

3051 GTGAAAGGGC ATGTAGATGT AGAAGAACAA AACAACCACC GTTCGGTCCT

3101 TGTTGTTCCG GAATGGGAAG CAGAAGTGTC ACAAGAAGTT CGTGTCTGTC

3151 CGGGTCGTGG CTATATCCTT CGTGTCACAG CGTACAAGGA GGGATATGGA

3201 GAAGGTTGCG TAACCATTCA TGAGATCGAG AACAATACAG ACGAACTGAA

3251 GTTTAGCAAC TGTGTAGAAG AGGAAGTATA TCCAAACAAC ACGGTAACGT

3301 GTAATGATTA TACTGCGACT CAAGAAGAAT ATGAGGGTAC GTACACTTCT

3351 CGTAATCGAG GATATGACGG AGCCTATGAA AGCAATTCTT CTGTACCAGC

3401 TGATTATGCA TCAGCCTATG AAGAAAAAGC ATATACAGAT GGACGAAGAG

3451 ACAATCCTTG TGAATCTAAC AGAGGATATG GGATTACAC ACCACTACCA

3501 GCTGGCTATG TGACAAAAGA ATTAGAGTAC TTCCCAGAAA CCGATAAGGT

3551 ATGGATTGAG ATCGGAGAAA CGGAAGGAAC ATTCATCGTG GACAGCGTGG

3601 AATTACTTCT TATGGAGGAA TAATATATGC TTTATAATGT AAGGTGTGCA

3651 AATAAAGAAT GATTACTGAC TTGTATTGAC AGATAAATAA GGAAATTTTT

3701 ATATGAATAA AAAACGGGCA TCACTCTTAA AAGAATGATG TCCGTTTTTT

3751 GTATGATTTA ACGAGTGATA TTTAAATGTT TTTTTTGCGA AGGCTTTACT

3801 TAACGGGGTA CCGCCACATG CCCATCAACT TAAGAATTTG CACTACCCCC

3851 AAGTGTCAAA AAACGTTATT CTTTCTAAAA AGCTAGCTAG AAAGGATGAC

3901 ATTTTTTATG AATCTTTCAA TTCAAGATGA ATTACAACTA TTTTCTGAAG

FIG.13D

3951 AGCTGTATCG TCATTTAACC CCTTCTCTTT TGGAAGAACT CGCTAAAGAA

4001 TTACGTTTTG TAAAAAGAAA ACGAAAGTTT TCAGGAAATG AATTAGCTAC

4051 CATATGTATC TGGGGCAGTC AACGTACAGC GAGTGATTCT CTCGTTCGAC

4101 TATGCAGTCA ATTACACGCC GCCACAGCAC TCTTATGAGT CCAGAAGGAC

4151 TCAATAAACG CTTTGATAAA AAAGCGGTTG AATTTTTGAA ATATATTTTT

4201 TCTGCATTAT GGAAAAGTAA ACTTTGTAAA ACATCAGCCA TTTCAAGTGC

4251 AGCACTCACG TATTTTCAAC GAATCCGTAT TTTAGATGCG ACGATTTTCC

4301 AAGTACCGAA ACATTTAGCA CATGTATATC CTGGGTCAGG TGGTTGTGCA

4351 CAAACTGCAG

FIG.13E

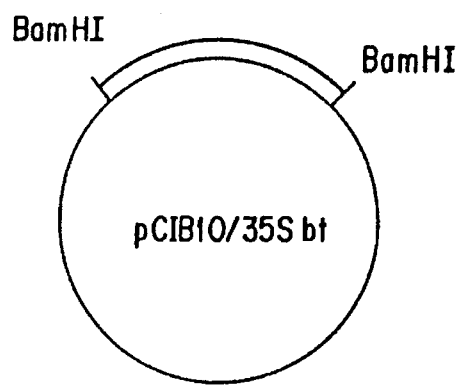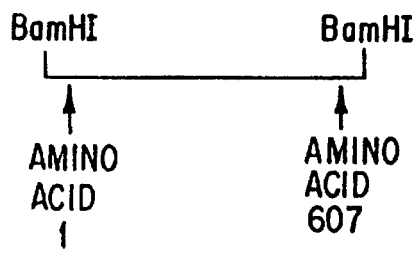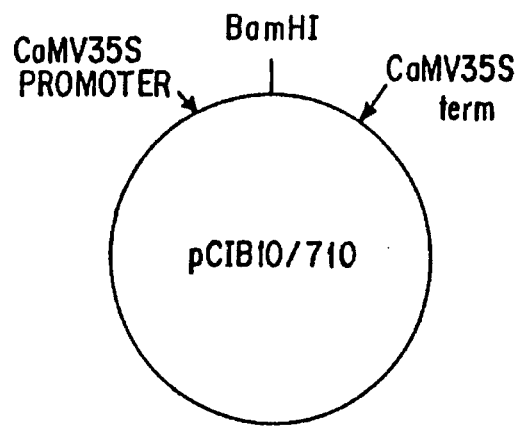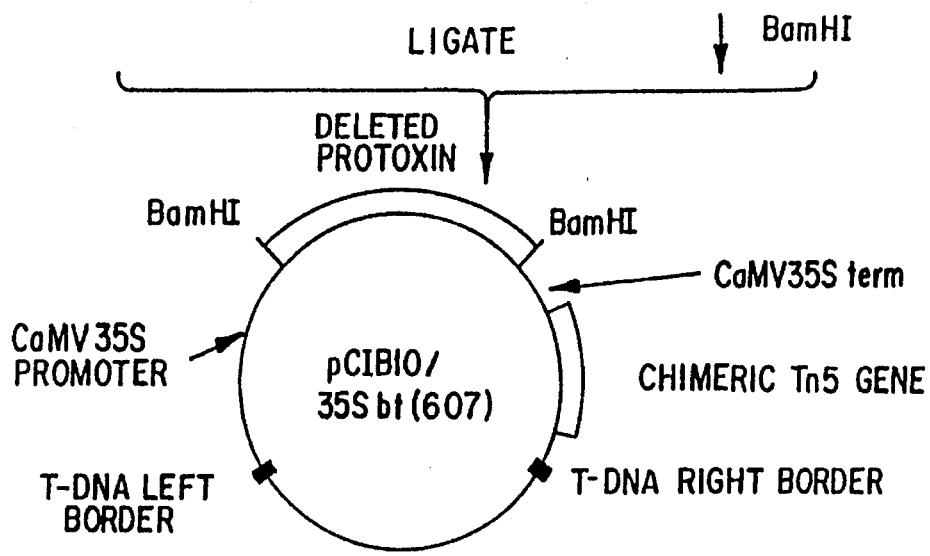
FIG. 17

METHODS FOR PROTECTING ZEA MAYS PLANTS AGAINST PEST DAMAGE

This application is a divisional of U.S. patent application Ser. No. 08/269,677, filed Jul. 1 1994; which is a continuation of U.S. patent application Ser. No. 08/024,875, filed Mar. 1, 1993, which issued as U.S Pat. No. 5,350,689 on Sep. 27, 1994; which is a continuation of U.S. patent application Ser. No. 07/276,210, filed Nov. 23, 1988, abandoned; which is a continuation-in-part of U.S. patent application Ser. No. 07/178,170, filed Apr. 6, 1988, abandoned; which is a continuation-in-part of U.S. patent applications Ser. No. 07/056,552, filed May 29, 1987, abandoned, and Ser. No. 07/056,506, filed May 29, 1987, abandoned; of which Ser. No. 07/056,506 is a continuation-in-part of U.S. patent application Ser. No. 07/053,241, filed May 22, 1987, abandoned; which is a continuation-in-part of U.S. patent application Ser. No. 07/052,440, filed May 20, 1987, abandoned.

FIELD OF THE INVENTION

The present invention relates to corn (*Zea mays*) plants that are regenerated from protoplasts or from protoplast-derived cells and to generally applicable methods for regeneration of these plants. It also relates to the embryogenic cell cultures (suspension cultures or callus cultures) and calli that constitute the source for *Zea mays* protoplasts which can be regenerated into plants. It further relates to the methods of producing the embryogenic cell cultures mentioned above, and of the embryogenic calli. It further relates to genetically altered *Zea mays* plants, preferably transgenic *Zea mays* plants regenerated from genetically modified protoplasts. An additional embodiment of the present invention is a method for increasing division of, or colony formation from plant protoplasts. The present invention is further directed to a chimeric gene that expresses in corn (*Zea mays*) cells insecticides having substantially the insect toxicity properties of the crystal protean produced by *Bacillus thuringiensis*.

BACKGROUND OF THE INVENTION

(PART A) REGENERATION OF ZEA MAYS PLANTS FROM PROTOPLASTS

Descriptions of regeneration of *Zea mays* from callus mainly date from the mid 1970's" [for example: Green and Phillips, *Crop Sc.*, 15 (1975) 417–421,; Harms et al. *Z. Pflanzenzuechtg.*, 77 (1976) 347–351; European patent applications EP-0,160,390, Lowe and Smith (1985); EP-0,176,162, Cheng (1985); and EP-0,177,738, Close (1985)]. Attempts have been made to obtain division and subsequent plant regeneration from protoplasts of *Zea mays* over a period of more than 12 years [Potrykus et al., In: *Cell Genetics in Higher Plants*, Dudits et al., (eds), Akademiai Kiado, Budapest (1976) 129–140, and references therein; Harms, "Maize and Cereal Protoplasts-Facts and Perspectives," *Maize for Biological Research*, W. F. Sheridan, ed. (1982); Dale, in: Protoplasts (1983); Potrykus et al (eds.) *Lecture Proceedings, Experientia Supplementum* 46, Potrykus et al., eds, Birkhauser, Basel (1983) 31–41, and references therein]. However, protoplasts of *Zea mays* have always given rise only to cultures which have not been capable of regenerating fertile plants [Potrykus et al., *Mol. Gen. Genet.* 156 (1977) 347–350; Potrykus et al., *Theor. Appl. Genet.*, 54 (1979) 209–214; Choury and Zurawski, *Theor. Appl. Genet.*, 59 (1981) 341–344; Vasil, In: *Proc. 5th Int. Cong. Plant Tissue and Cell Culture*, Fujiwara (ed), Tokyo, (1982) 101–104; Imbrie-Milligan and Hodges, Planta, 168, (1986) 395–401; Vasil and Vasil, *Theor. Appl. Genet.*, 73 (1987) 793–798]. However, none of these references provides a description of a procedure for producing protoplasts capable of regenerating fertile plants have appeared.

The ability to produce such protoplasts would allow the genetic manipulation of this important crop by, for example, transformation or fusion, or the use of protoplasts as the starting material for selection of valuable new phenotypes.

Although there has been great interest in genetic transformation of *Zea mays*, there has been no description to date of a successful in vitro method which can lead to a regenerated, transformed plant, although there have been descriptions of transformation of *Zea mays* protoplasts that have led to the recovery of non-regenerable callus [Fromm et al., *Nature*, 319, (1986) 791–793]. One method to produce transgenic *Zea mays* plants would be to find a way in which to stably transform protoplasts capable of regeneration to whole fertile plants. However no description of a method to produce *Zea mays* protoplasts capable of undergoing differentiation to whole fertile plants has appeared.

This and other objectives have been achieved in accordance with the present invention by discovering a method for producing *Zea mays* protoplasts that can divide to form callus colonies. The protoplasts can be transformed, and the calli are capable of regenerating fertile *Zea mays* plants. The process for producing *Zea mays* protoplasts capable of dividing and forming callus, which can then be induced to regenerate into whole fertile plants requires a special type of callus. Such callus and methods for producing and identifying it will be described, and are considered part of the invention.

The special type of callus is used to initiate cell suspensions, which are also considered part of the invention. These cell suspensions, upon subculture, give rise to suspensions which can be used to isolate protoplasts. These protoplasts are capable of dividing and forming callus, which can then be induced to regenerate plants. Cell division or callus formation is promoted by the presence of certain agents, such as O-loweralkanoyl-salicylic acid (O-acetyl-salicylic acid and its homologs), plant growth regulators or DMSO, or by combinations of these agents.

Plant regeneration from protoplast-derived *Zea mays* cells in culture is essential for the application of somatic hybridization, for the production of improved *Zea mays* varieties through somaclonal variation, and for the use of genetic engineering in producing new *Zea mays* plants, plant varieties, cultivars or inbreds with new phenotypic traits.

(PART B) INSECTICIDAL CORN (ZEA MAYS) PLANTS

*Bacillus thuringiensis* (hereinafter Bt) is a species of bacteria that produces a crystal protein, also referred to as delta-endotoxin. This crystal protein is, technically, a protoxin that is converted into a toxin upon being ingested by larvae of lepidopteran, coleopteran and dipteran insects.

The crystal protein from Bt is a potentially important insecticide having no known harmful effects on humans, other mammals, birds, fish or on insects other than the larvae of lepidopteran, coleopteran and dipteran insects. The activity of the Bt toxin is extremly high, so that only nanogram amounts are required to kill susceptible insect larvae. Other advantages of the use of the crystal protein from Bt as an insecticide include its broad spectrum of activity against lepidopteran, coleopteran and dipteran insect larvae, and the apparent difficulty of such larvae to develop resistance against the crystal protein, even where the crystal protein is used on a large scale. Said larvae are a major problem in agriculture and forestry, and especially in corn cultivation.

The crystal protein is effective as an insecticide when it is applied to plants subject to lepidopteran, coleopteran or dipteran larvae infestation.

So far, the Bt crystal protein (protoxin) was isolated from the Bacillus and applied to the plants by standard methods such as by dusting or spraying. Preparations containing the Bt. crystal protein are used commercially as biological insecticides. For example: Bactospeine, distributed by Biochem Products Ltd., Dipel distributed by Abbot Laboratories; and Thurcide, distributed by Sandoz AG. The fact that Bt produces the crystal protein only during sporulation represents a significant disadvantage in connection with the manufacture and use of this biological insecticide. Such growth phase limitation, particularly in an industrial process, can result in inconvenience and exessive time requirements during manufacture. In addition, costs associated with said manufacture made it difficult for such a biological insecticide to compete effectively with other commercially available products based on chemicals, such as, for example, pyrethroid derivatives.

A further disadvantage with respect to the use of the Bt toxin is, for example, the fact that the protein usually remains on the surface of the treated plants, where it is effective only against surface-feeding larvae, and where it is inactivated by prolonged exposure to ultraviolet radiation. This inactivation may be at least one cause of the general lack of persistence of the crystal protein in the environment. Accordingly, frequent and expensive application of the crystal protein is necessary.

These and other disadvantages can be overcome by incorporating and expressing a gene coding for a Bt crystal protein or for a protein having substantially the insect toxicity properties of a Bt crystal protein in plants. The present invention describes how these disadvantages can be overcome by incorporating and expressing a gene coding for a Bt crystal protein or for a protein having substantially the insect toxicity properties of a Bt crystal protein in corn protoplasts and regenerating fertile transgenic corn plants from the transformed protoplasts and culturing these insect resistant corn plants.

By taking advantage of genetic engineering, a gene responsible for the production of a useful polypeptide can be transferred from a donor cell, in which the gene naturally occurs, to a host cell, in which the gene does not naturally occur; Cohen and Boyer, U.S. Pat. Nos. 4,237,224 and 4,468,464. There are, in fact, few inherent limits to such transfers. Genes can be transferred between viruses, bacteria, plants and animals. In some cases, the transferred gene is functional, or can be made to be functional, in the host cell. When the host cell is a plant cell, whole plants can sometimes be regenerated from the cell.

Genes typically contain regions of DNA sequences including a promoter and a transcribed region. The transcribed region normally contains a 5' untranslated region, a coding sequence, and a 3' untranslated region.

The promoter contains the DNA sequence necessary for the initiation of transcription, during which the transcribed region is converted into mRNA. In eukaryotic cells, the promoter is believed to include a region recognized by RNA polymerase and a region which positions the RNA polymerase on the DNA for the initiation of transcription. This latter region is referred to as the TATA box, which usually occurs about 30 nucleotides upstream from the site of transcription initiation.

Following the promoter region is a sequence that is transcribed into mRNA but is not translated into polypeptide. This sequence constitutes the so-called 5' untranslated region and is believed to contain sequences that are responsible for the initiation of translation, such as a ribosome binding site.

The coding region is the sequence that is just downstream from the 5' untranslated region in the DNA or the corresponding RNA. It is the coding region that is translated into polypeptides in accordance with the genetic code. Bt, for example, has a gene with a coding sequence that translates into the amino acid sequence of the insecticidal protoxin crystal protein.

The coding region is followed downstream by a sequence that is transcribed into mRNA, but is not translated into polypeptide. This sequence is called the 3' untranslated region and is believed to contain a signal that leads to the termination of transcription and, in eukaryotic mRNA, a signal that causes polyadenylation of the transcribed mRNA strand. Polyadenylation of the mRNA is believed to have processing and transportation functions Natural genes can be transferred in their entirety from a donor cell to a host cell. It is often preferable however, to construct a gene containing the desired coding region with a promoter and, optionally, 5' and 3' untranslated regions that do not, in nature, exist in the same gene as the coding region. Such constructs are known as chimeric genes.

Genetic engineering methods have been described for improved ways of producing the crystal protein. For example, Schnepf et al., U.S. Pat. Nos. 4,448,885 and 4,467,036, describe plasmids for producing crystal protein in bacterial strains other than Bt These methods permit production of the crystal protein, but do not overcome the disadvantages of using the crystal protein as a commercial insecticide.

Suggestions have been made to clone Bt toxin genes directly into plants in order to permit the plants to protect themselves; [Klausher, A., *Biotechnology,* 2 (1984) 409–413]. Adang et al., European Patent Application EP-0, 142,924 (Agrigenetics) and DeGreve, H. M. J., et al., EP-0,193,259 (Plant Genetic Systems N.V.) allege a method for cloning toxin genes from Bt in tobacco. In none of these publications the transformation of monocotyledonous plants is exemplified.

A need exists for developing new methods for producing the crystal protein of Bt in cells of corn plants and for new methods of controlling insect larvae which feed on corn plants containing a Bt crystal protein or a similar polypeptide having substantially the insect toxicity properties (insecticidal activity) of a Bt crystal protein. "Controlling" should be understood as referring either to killing the larvae, or at least reducing their feeding. Further need exists for a method for protecting corn plants against damage caused by pests or pathogens comprising the production of an amount of a pesticidal or antipathogenic protein in the plant cell and plant respectively, which amount is sufficiently effective for killing or controlling the pest or the pathogen. Further need exists preferably for a method for protecting corn plants against insect damage comprising the production of an insecticidal effective amount of a Bt crystal protein or a protein having substantially the insect toxicity properties of a Bt crystal protein in the plant cell. Further need exists for a method for protecting corn plants from damage by chemical agents, such as, for example herbicides, in order for such chemicals can be safely applied to corn plants.

SUMMARY OF THE INVENTION

These and other objectives have been achieved in accordance with the present invention which provides a method for producing corn (*Zea mays*) protoplasts that can form cell and callus colonies. The protoplasts can, if desired, be transformed, and the resultant cells and calli are capable of being regenerated into transgenic *Zea mays* plants. The process for producing protoplasts capable of dividing and forming callus, which then can be regenerated into plants, requires as a starting material a novel embryogenic cell culture (suspension cultures or callus cultures). Such embryogenic cell cultures and methods for producing and identifying them will be described, and are considered part of the invention. Embryogenic callus from which the suspensions are derived can also be used as a starting material for protoplasts. Such callus and suspensions, embryos and methods for producing and identifying them will be described, and are also considered part of the present invention.

These embryogenic suspension cultures are capable of being regenerated into whole fertile corn plants and represent a preferred subject of the present invention.

These embryogenic cultures are the source of protoplasts capable of being transformed with exogenous DNA, and of dividing and forming callus, which then can be regenerated into plants, including whole, fertile *Zea mays* plants that can grow in soil.

This invention further provides chimeric genes capable of expressing in corn cells a polypeptide having substantially the insect toxicity properties of Bt crystal protein (hereinafter, chimeric Bt toxin gene).

Additional embodiments of the present invention include the chimeric Bt toxin gene in vectors, bacteria, plant cells in culture, and plant cells in living plants, as well as methods for producing a toxin having substantially the insect toxicity properties of Bt crystal protein in corn cells and methods for controlling or killing insects by feeding them corn cells containing a gene that expresses such a toxin.

This invention further describes methods for protecting *Zea mays* from damage by fungal pathogens by introducing and expressing in corn cells and plants a gene encoding a polypeptide having chitinase activity.

This invention further describes methods for introducing and expressing in corn cells and plants a gene encoding a polypeptide which renders the cells and plants tolerant to herbicidal chemicals.

One could not predict from the prior art at the time this invention was made, that corn (*Zea mays*) plants, particularly fertile corn plants could be regenerated from protoplasts, from protoplast-derived cells or protoplast-derived calli. Even less predictable was that *Zea mays* protoplasts containing stably incorporated exogenous DNA could also be regenerated into transgenic plants, particularly into fertile transgenic *Zea mays* plants.

OBJECTS OF THE INVENTION

This invention is directed to embryogenic cell cultures (suspension cultures or callus cultures) derived from *Zea mays* plants from which protoplasts can be isolated, wherein the protoplasts regenerate cell walls, divide and form callus capable of being regenerated into plants, including fertile *Zea mays* plants.

This invention also relates to *Zea mays* protoplasts and the resulting protoplast-derived plant cells (after regeneration of the cell walls) that can be regenerated into plants which are preferably fertile, preferably to such protoplasts derived from cell cultures or from embryogenic cell suspensions.

This invention also relates to embryogenic cell suspension cultures which can be regenerated into fertile corn plants.

This invention also relates to *Zea mays* plant cells, calli, embryogenic suspensions, embryos, plantlets and plants derived from protoplasts, from transformed or otherwise genetically altered protoplasts.

Furthermore, this invention relates to propagules and the progeny of regenerated *Zea mays* plants which are derived from embryogenic cell suspension cultures or cultured protoplasts. Propagules include any material that can be sexually or asexually propagated or propagated in-vivo or in-vitro. Among this propagating material protoplasts, cells, calli, tissues or seeds are preferred. The progeny of said regenerated *Zea mays* plants includes mutants and variants thereof. Mutants and variants include, for example, those plants obtained from cell fusion or mutant selection.

This invention preferably relates to regenerated (protoplast-derived) transgenic *Zea mays* plants and the propagules and progeny thereof, having stably incorporated exogenous DNA, preferably exogenous DNA expressible in *Zea mays*, more preferably a chimeric gene that provides the transformed plant with a valuable property. Valuable properties are described subsequently.

Propagules of said transgenic *Zea mays* plants include any material that can be sexually or asexually propagated or propagated in-vivo or in-vitro. Among this propagating material protoplasts, cells, calli, tissues or seeds obtained from said transgenic *Zea mays* plants are preferred. The progeny of transgenic *Zea mays* plants includes mutants and variants thereof. Mutants and variants include, for example, those plants obtained from cell fusion or mutant selection.

This invention also relates to a method of producing *Zea mays* protoplasts and *Zea mays* plant cells that can be regenerated into plants, particularly into fertile plants, moreover, to a method of producing *Zea mays* calli derived from said protoplasts or protoplast-derived cells and being capable of regeneration into plants, preferably into fertile plants. In addition, it relates to a method of regenerating *Zea mays* plants and transgenic *Zea mays* plants, from these cells (callus or suspension culture cells.

These methods are described in detail hereinafter.

It is a further object of the present invention to provide a method for producing in *Zea mays* cells a Bt crystal protein or a protein that has substantially the insect toxicity properties of a Bt crystal protein. Especially preferred is a method for producing in *Zea mays* a polypeptide having substantially the insect toxicity properties of a *Bacillus thuringensis* crystal protein, which method comprises:

(a) introducing into *Zea mays* cells a gene coding for a polypeptide having substantially the insect toxicity properties of a Bt crystal protein wherein the promoter, 5' untranslated region, and optionally, the 3' untranslated region of the gene are derived from plant or plant virus gene and (b) expressing the polypeptide.

It is a further object of the present invention to provide a method for protecting *Zea mays* plants against damage caused by a pathogen which attacks *Zea mays* plants, which method comprises producing in the plant cell an antipathogenically effective amount or an amount sufficient to control the pathogen of a protein having antipathogenic or pathogen-controlling activity.

It is a further object of the present invention to provide a method for protecting *Zea mays* plants against pest damage comprising the production in the plant cell of a pesticidally effective amount or an amount sufficient to control the pest of a protein having pesticidal or pest-controlling activity. Especially preferred is a method wherein the pest is an insect.

It is a further object of the present invention to provide a method of controlling insect larvae, preferably lepidopteran, coleopteran and dipteran larvae by feeding them corn plant cells containing chimeric genes which express an insecticidal amount of a Bt crystal toxin or a toxin having substantially the insect toxicity properties of Btαβ crystal protein.

It is a further object of the present invention to provide a method for protecting corn plants against insect damage comprising the production of a controlling or insecticidal effective amount of a Bt crystal protein or a protein having substantially the insect toxicity properties of a Bt crystal protein in the plant cell. The insecticidal corn plant cells include those from whole plants and parts of plants as well as cultured corn cells.

It is a further object of the present invention to provide a method wherein the protein is produced in an amount sufficient to render the plant unattractive to the insect so that they stop feeding on the plant.

It is an additional object of the present invention to provide the genes and other DNA segments as well as the cells and plants associated with the above methods.

These and further objects will become available from the following detailed description.

BRIEF DESCRIPTION OF THE FIGURES

FIG. 7h shows the construction of pCIB10a.

FIG. 13 shows the nucleotide sequence of the endotoxin gene from *Bacillus thuringiensis* var. kurstaki HD1. A preferred sequence of nucleotides that codes for a crystal protein is that shown as nucleotides 156 to 3623 in the sequence or a shorter sequence that codes for an insecticidal fragment of such a crystal protein; Geiser et al., *Gene*, 48 (1986) 109–118.

Lanes 1–4: 0.5, 1, 2, and 5 copy(ies) per genome reconstructions of pCIB712 cut with restriction endonuclease EcoRI.

Lanes 5–25: DNA from *Zea mays* callus cultures recovered after transformation of protoplasts with pCIB712, cut with restriction endonuclease EcoRI.

The DNA in Lane 10 clearly shows the presence of foreign DNA integrated into the genome of *Zea mays* cells as evidenced by the darkening of the film. The arrow points to the 975 bp fragment which is expected from EcoRI digestion of the integrated APH IV gene of pCIB712 which confers hygromycin resistance to the transgenic cells.

Figure 15:
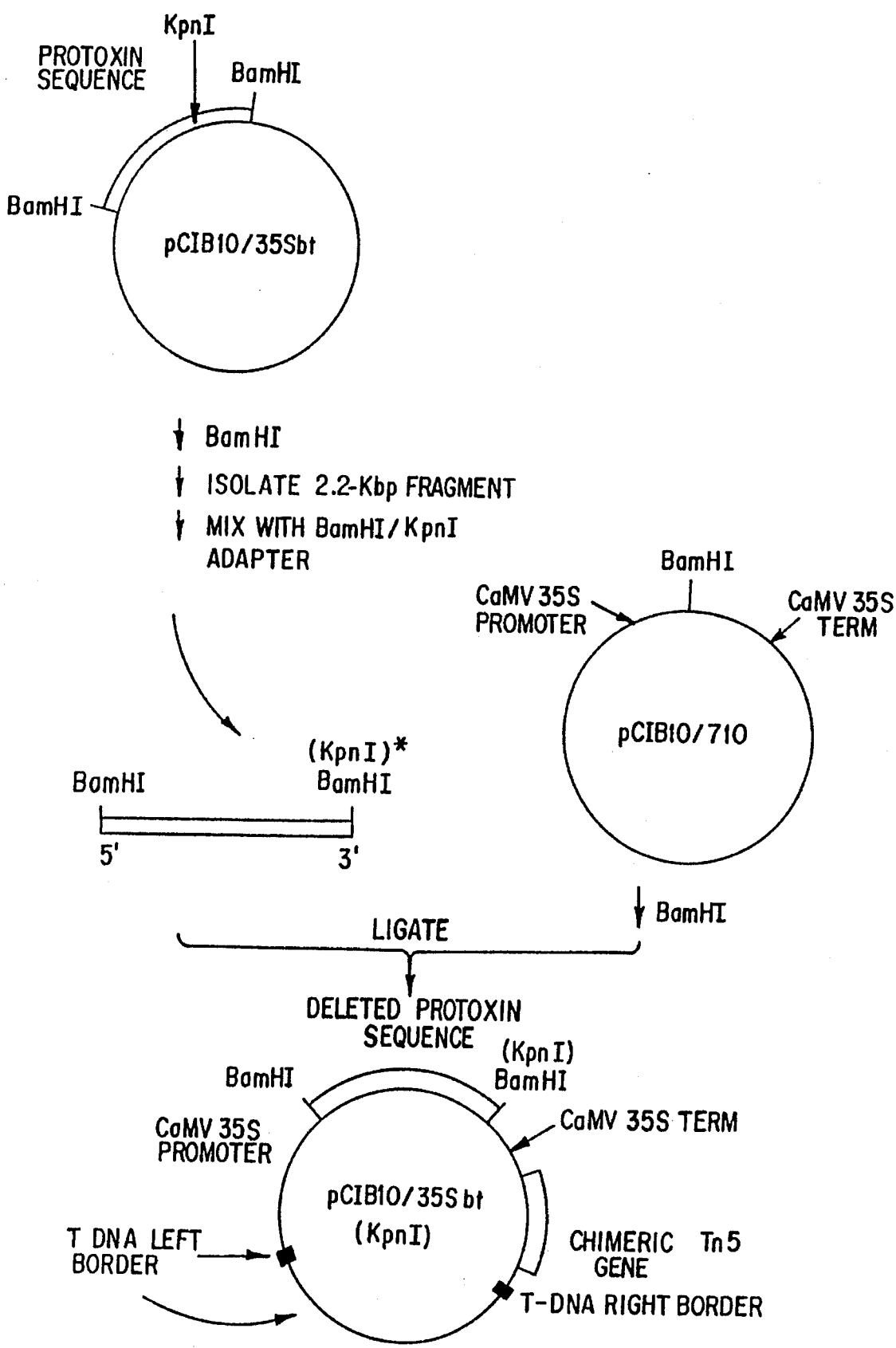
Figure 16:
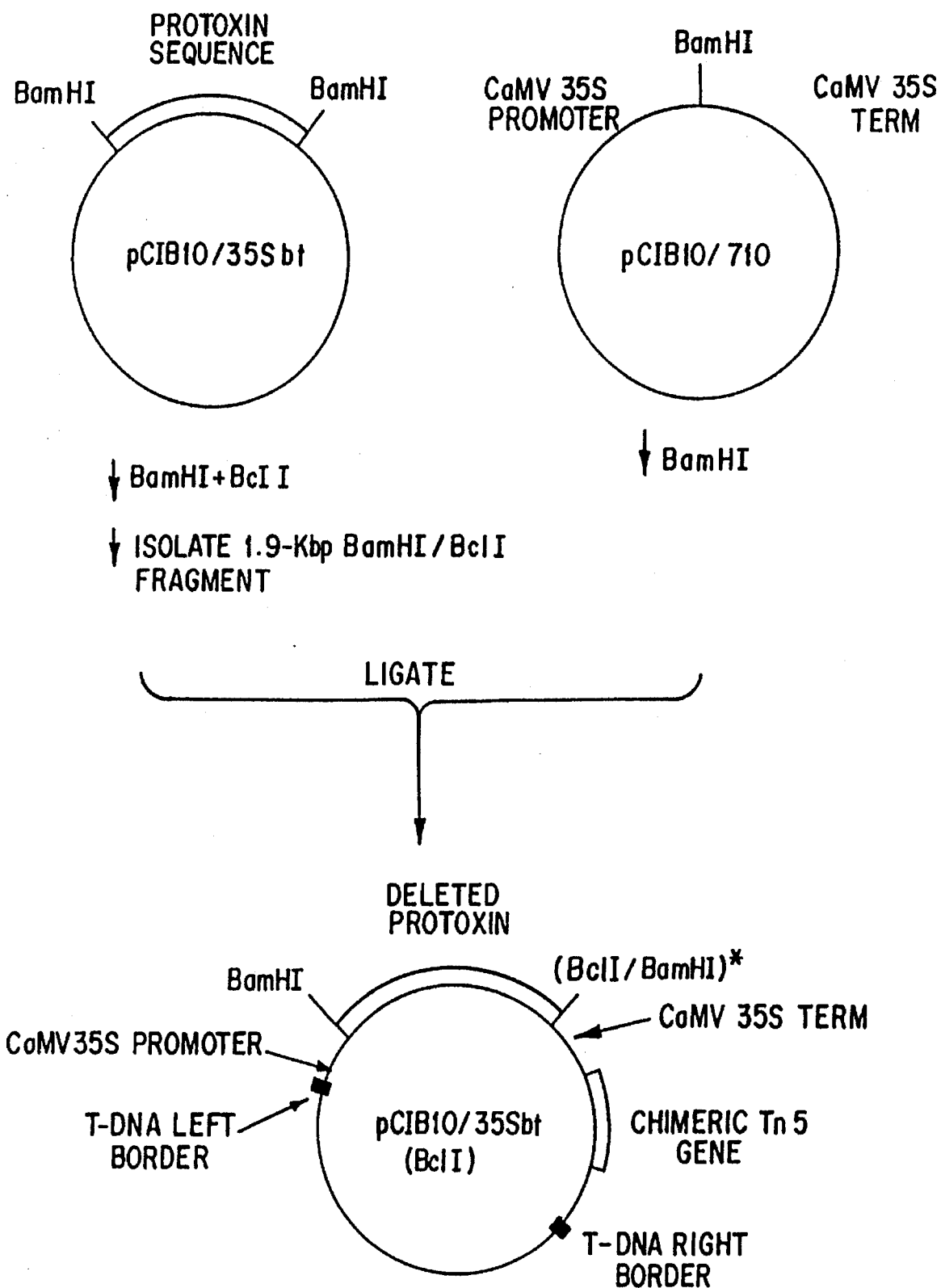

FIG. 15 shows the construction of pCIB10/35SBt(KpnI).
FIG. 16 shows the construction of pCIB10/35SBt(BclI).
FIG. 17 shows the construction of pCIB10/35SBt(607).

Figure 18:
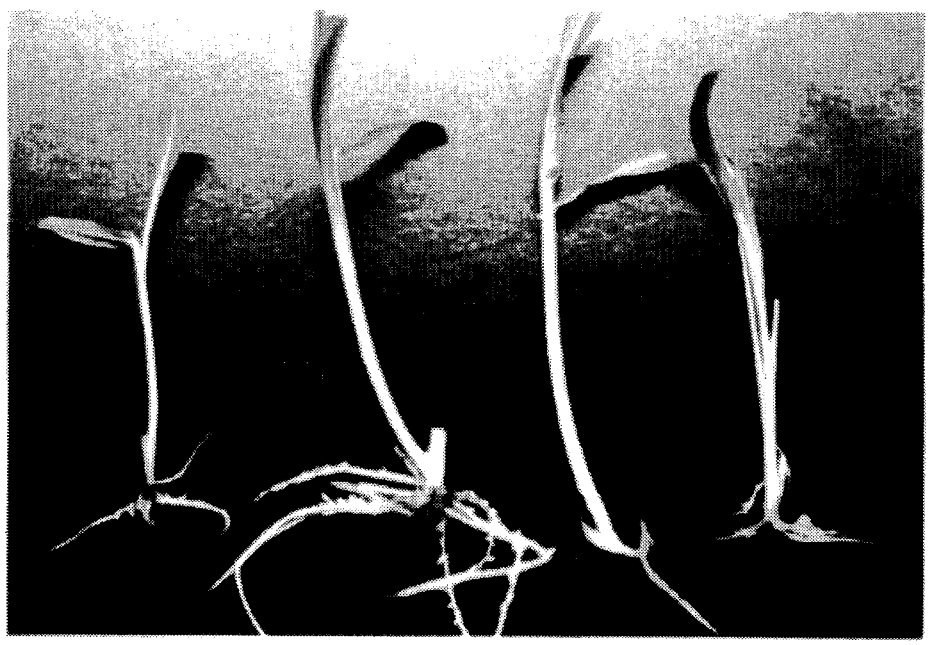

FIG. 18 shows *Zea mays* plants regenerated from protoplast-derived callus ready for potting in soil mixture.

Figure 19:

FIG. 19 shows *Zea mays* plants regenerated from protoplast-derived callus growing in soil mixture.

Figure 20:
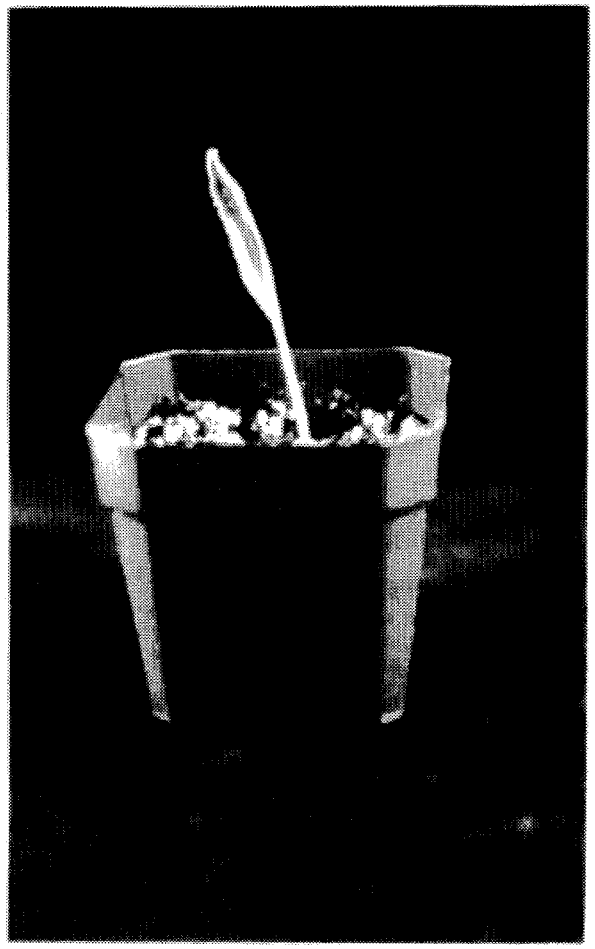

FIG. 20 shows a seedling from seed produced on a *Zea mays* plant derived from protoplasts.

DEFINITIONS

*Zea mays*/corn: Throughout the present specification or claims these terms refer to any plant or part of a plant (protoplasts, cells, tissues, organs, organelles, embryos, calli, propagules, etc.) belonging to the species of *Zea mays*. The terms as used here include races, cultivars, varieties, inbred lines and hybrids of *Zea mays*. The present invention includes but is not limited to corn inbred lines like, for example, Funk 5N984, Funk 5N986, Funk 2717, Funk 211D, Funk 2N217A, B73, A632, CM105, B37, B84, B14, Mo17, R168, MS71, A188, FA91, A641 and W117. Preferred are all elite genotypes (varieties, cultivars, inbred lines, hybrids, etc.), including the elite inbred lines Funk 5N984, Funk 5N986, Funk 2717, Funk 211D and Funk 2N217A, most preferably the elite inbred line Funk 2717.

BMS: "Black Mexican Sweet Corn". An old, small eared, sweet corn variety with dark blue coloration of the kernel pericarp, giving the kernels a "black" appearance.

Plant cell: The structural and physiological unit of plants, consisting of a protoplast and the cell wall.

The term "plant cell" refers to any cell which is either part of or derived from a plant. Some examples of cells encompassed by the present invention include differentiated cells that are part of a living plant; differentiated cells in culture; undifferentiated cells in culture; the cells of undifferentiated tissue such as callus or tumors; seeds; embryos; propagules and pollen.

Plant Tissue: A group of plant cells organized into a structural and functional unit. Any tissue of a plant in planta or in culture. This term includes, but is not limited to, whole plants, plant cells, plant organs, plant seeds, protoplasts, cell culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Plant Organ: A distinct and visibly structured and differentiated part of a plant such as root, stem, leaf, flower bud, or embryo. A plant organ may consist of different types of plant cells or plant tissues.

Protoplast: Isolated plant cell without a cell wall.

Transgenic Plant: A plant having stably incorporated exogenous DNA in its genetic material. The term includes exogenous DNA which may be introduced into the protoplasts in various forms, including, for example, naked DNA in circular, linear or supercoiled form, DNA contained in nucleosomes or chromosomes or nuclei or parts thereof, DNA complexed or associated with other molecules, DNA enclosed in liposomes, spheroplasts, cells or protoplasts. Various different methods of introducing the exogenous DNA into protoplasts are known in the art and can be used to produce the transgenic protoplasts, transgenic cells or transgenic plants of the present invention.

Culture: A proliferating mass of cells in an undifferentiated or partially differentiated state. The term "cell culture" includes callus cultures consisting of cell masses growing on solidified culture medium and suspension culture cells growing in a dispersed state in an agitated liquid culture medium.

Embryo: A minute early developmental stage of a plant, either derived from a zygote (then called sexual embryo) or from an embryogenic somatic cell (then called somatic embryo), with stages of recognizable morphology, structure and cellular organization comprising cellular to globular to cotyledonary stages. [Corn embryo development is, for example, described in Randolph, L. F., *J. Agric. Research*, 53 (1936) 881–916; grass embryo development in general is, for example, described in Brown, W. V., [*Phytomorphology*, 10 (1960) 215–223.]

Plantlet: A multicellular structure made up of a shoot and root in the form of a small plant.

Chimeric Sequence or chimeric Gene: A DNA sequence containing at least two heterologous parts, e.g., parts derived from, or having substantial sequence homology to, pre-existing DNA sequences which are not associated in their pre-existing states. The pre-existing DNA sequences may be of natural or synthetic origin.

Coding DNA Sequence: A DNA sequence which, when transcribed and translated, results in the formation of a cellular polypeptide.

Gene: A discrete chromosomal region comprising a regulatory DNA sequences responsible for the control of expression, i.e. transcription and translation, and of a coding sequence which is transcribed and translated to give a distinct polypeptide.

Derived from: In the context of this application genes, pats of genes, or other DNA sequences "derived from" other DNA sources embraces genes, parts of genes or other DNA sequences, identical to or substantially homologous to the DNA source material.

Phenotypic Trait: An observable property resulting from the expression of one or more genes.

Pre-existing DNA Sequence: A DNA sequence that exists prior to its use, in toto or in part, in a product or method according to the present invention. While such pre-existence typically reflects a natural origin, pre-existing sequences may be of synthetic or other origin.

Substantial Sequence Homology: Substantial functional and/or structural equivalence between sequences of nucleotides or amino acids. Functional and/or structural differences between sequences having substantial sequence homology will be de minimus.

Dicamba: 3,6-dichloro-2-methoxy benzoic acid.

MES: 2-[N-morpholino]ethane sulfonic acid.

2,4-D: 2,4-dichlorophenoxyacetic acid.

Picloram: 4-amino-3,6,6-trichloropicolinic acid.

Tris-HCl: alpha, alpha, alpha-tris(hydroxymethyl)methylamine hydrochloride.

EDTA: 1-ethylendiamine N,N,,N',N'-tetraacetic acid

PEG: polyethylene glycol

Agarose: Preparation and purification of agarose are described, for example by Guiseley and Renn, ["The Agarose Monograph", Marine Colloids Division FMC Corp. (1975)]. Agarose is one of the constituents of agar. Commercially available agar normally consists of a mixture of neutral agarose and ionic agaropectin with a large number of side groups. Commercial agarose is normally obtained from agar by conventional methods. Usually a certain number of side chains remains intact and determines the physicochemical properties of the agarose, such as gel formation and melting temperature. Low-melting agarose, especially SeaPlaque® agarose, is a preferred solidifying agent within the process described hereinafter.

SH medium: Medium of Schenk, R. U., et al., *Can. J. Bot.* 50 (1972) 199–204; without growth regulators. (SH medium can be liquid or solidified with 0.8% (w/v) agar or with 0.5% (w/v) GelRite®). The medium is normally sterilized by methods known in the art, for example, by heat or sterilized by autoclaving it at 121° C. and 15 lb/in$^2$ [1.2 kg/cm$^2$] pressure for about 15 to 20 minutes.

MS Medium: Murashige, T., and Skoog, F., *Physiol. Plant.*, 15 (1962) 473.

B5 Medium: Gamborg, O. et al., *Exp. Cell Res.*, 50 (1968) 151.

N6 Medium: Chu et al., *Scientia Sinica*, 18 (1975) 659. Composition given in Table 1 below.

KM Medium: Kao, K. N., et al., *Planta*, 126 (1975) 105–110. This medium may be liquid or solidified with agar, agarose or GelRite® and may equally well be prepared and used without ascorbic acid, vitamin D, and vitamin A. The medium components except solidifying agent are normally sterilized by filtration through a 0.2 μm filter. (Composition given in Table 1 below.)

TABLE 1

Composition of media used.
Macroelementa and microelementa of the media
are as given in the literature.

| MEDIUM: | KM[b,c,d] | N6 |
|---|---|---|
| Vitamins used in the culture media[e]: mg/liter | | |
| Biotin | 0.01 | |
| Pyridoxine HCl | 1.00 | 0.5 |
| Thiamine HCl | 10.00 | 0.1 |
| Nicotinamide | 1.00 | |
| Nicotinic acid | 0.10 | 0.5 |
| Folic acid | 0.40 | |
| D-Ca-Pantothenate | | 1.00 |
| p-Aminobenzoic acid | | 0.02 |
| Choline chloride | | 1.00 |
| Riboflavin | 0.20 | |
| Vitamin B12 | 0.02 | |
| Glycine | 0.10 | 2.0 |
| Sugars and sugar alcohols: g/liter | | |
| Sucrose | 0.25 | 30.0 |
| Glucose | 68.40 | |
| Mannitol | 0.25 | |
| Sorbitol | 0.25 | |
| Cellobiose | 0.25 | |
| Fructose | 0.25 | |
| Mannose | 0.25 | |
| Rhamnose | 0.25 | |
| Ribose | 0.25 | |
| Xylose | 0.25 | |
| m-Inositol | 0.10 | |
| Final pH | 5.8 | 5.6 |

Footnotes to Table 1:
[a]macroelements are usually made up as a 10x concentrated stock solution, and microelements as a 1000x concentrated stock solution.
[b]Citric, fumaric and malic acid (each 40 mg/liter final concentration) and sodium pyruvate (20 mg/liter final concentration) are prepared as a 100x concentrated stock solution, adjusted to pH 6.5 with $NH_4OH$, and added to this medium.
[c]Adenine (0.1 mg/liter final concentration), and guanine, thymine, uracil, hypoxanthine and cytosine (each 0.03 mg/liter final concentration) are prepared as a 1000x concentrated stock solution, adjusted to pH 6.5 as above and added to this medium.
[d]The following amino acids are added to this medium using a 10x stock solution (pH 6.5 with $NH_4OH$) to yield the given final concentrations: Glutamine (5.6 mg/liter), alanine, glutamic acid (each 0.6 mg/liter), cysteine (0.2 mg/liter), asparagine, aspartic acid, cystine, histidine, isoleucine, leucine, lysine, methionine, phenylalanine, proline, serine, threonine, tryptophan, tyrosine and valine (each 0.1 mg/liter).
[e]Vitamin stock solution is normally prepared 100x concentrated.

BAP: 6-benzyl-amino purine

OMS medium: The medium consisting of the salts of Murashige and Skoog [Physiol Plantarum, 15:473–497, 1962], with 3% w/v sucrose, and solidified with 0.24% w/v Gelrite®.

KMX medium: The medium consisting of the components of KM medium (Table 1) but with 2 mg/liter of 2,4-D, no glucose, 3% w/v sucrose, and solidified with 0.65% w/v purified agar ["Agar purified" Difco Laboratories, Detroit, Mich., U.S.A., catalogue number 0560-01]

Cellulase RS: Cellulase RS, Yakult Honsha Co. Ltd., 1.1.19 Higashi-Shinbashi, Minato-ku, Tokyo 105, Japan.

Pectolyase Y-23: Seishin Pharmaceutical Co. Ltd., 4-13 Koami-cho, Nihonbashi, Tokyo, Japan.

Nalgene® filter: Nalge Co., Division of Sybron Corp. Rochester, N.Y., 14602, U.S.A.

BglII: Restriction enzyme BglII; New England Biolabs, 32 Tozer Road, Beverly, Mass., 01915, USA, or any other commercial supplier.

BamHI: Restriction enzyme BamHI; New England Biolabs, 32 Tozer Road, Beverly, Mass., 01915, U.S.A., or any other commercial supplier.

Hygromycin B: Cytotoxin: Hygromycin B, purified; Cat No. 400050 Calbiochem Behring Diagnostica, La Jolla, Calif. 92037, USA, Lot No. 702296.

GelRite®: GelRite Gellan Gum, Scott Laboratories Inc., Fiskersville, R. I. 02823.

PRIME TIME random primer kit or IBI Random primer kit: International Biotechnologies Inc., PO. Box 1565, New Haven, Conn. 07606, U.S.A. (Catalog No. 77800; lot No. F630-01).

GA7® container: Small sterile container (about 7×7×10 cm) made of translucent plastic with translucent lid; used to grow plantlets, shoot cultures, etc.. Supplier: Magenta Corp., 3800 N.Milwaukee Avenue, Chicago, Ill., 60641, U.S.A. Can be replaced by any similar sterile translucent container (e.g. glass or plastic).

| Conversion of micro Einstein into lux: | |
|---|---|
| µE | lux |
| 0.1–200 | 8–16 700 |
| 0.1–100 | 8–8 350 |
| 30–90 | 2 500–7 500 |
| 10–40 | 830–3 330 |
| 30–80 | 2 500–6 670 |

Depositions of plasmids in microorganisms or of plant cells:

In connection with the present invention the following listed plasmids (in microorganisms) and plant cells were deposited in accordance with the requirements of the Budapest Treaty:

(1) *Zea mays* suspension cell culture 6-2717 CG of hybrid Funk 2717 is on deposit with American Type Culture Collection (ATCC), Rockville, USA, and has the ATCC accession number 40326 [date of deposit: May 20, 1987].

(2) Plasmid pCIB712 [in *E. coli* strain MC1061] is on deposit with ATCC and has the ATCC accession number 67407 [date of deposit: May 18, 1987].

(3) Plasmid pSCH1 [in *E. coli* strain K12] is on deposit with the Deutsche Sammlung yon Mikroorganismen (DMS) in Goettingen, Federal Republic of Germany, and has the DSM accession number 4129 [date of deposit: May 29, 1987].

(4) Plasmid pCIB10/35SBt [in *E. coli* strain MC1061] is on deposit with ATCC and has the ATCC accession number 67329 [date of deposit: Feb. 27, 1987].

(5) Plasmid pE16/8-c4 [in *E. coli* strain HB101] is on deposit with ATCC and has the ATCC accession number 67420 [date of deposit: May 29, 1987].

(6) Plasmid pCIB10/19SBt [in *E. coli* strain HB 101] is on deposit with ATCC and has the ATCC accession number 67330 [date of deposit: Feb. 27, 1987].

DETAILED DESCRIPTION OF THE INVENTION

(PART A) REGENERATION OF CORN *ZEA MAYS* PLANTS FROM PROTOPLASTS

The callus used in this invention can originate from any tissue of *Zea mays* plants. The tissue is preferably immature tissue such as immature tassel, immature embryos, the basal portion of young leaves, and in principle any other tissue of *Zea mays* capable of forming callus. An especially useful tissue is the scutellum of immature *Zea mays* embryos.

In principle, all *Zea mays* genotypes (varieties, cultivars, inbred lines, hybrids, etc.) are useful in the present invention. Most valuable are genotypes of commercial interest. Preferred are all elite genotypes, especially all inbred lines, more preferred are elite inbred lines. Suitable inbred lines are, for example, Funk 2717, Funk 211D, Funk 2N217A, B73, A632, CM105, B37, B84, B14, Mo17, R168, MS71, A188, FA91, A641 and W117. Funk 5N984 and Funk 5N986 are further examples of useful *Zea mays* genotypes. Espesially preferred are the elite inbred lines Funk 2717, Funk 211D, Funk 5N984 or Funk 2N217A, and most preferred is the elite genotype Funk 2717.

In the description below, a method for producing embryogenic suspensions of Funk 2717, from which protoplasts can be isolated, and which are capable of regenerating fertile plants will be described. It should be understood that other corn genotypes may be used in the described method with, at most, routine modifications known to those skilled in the art.

Step (a) Callus formation.

*Zea mays* plants of genotype Funk 2717 are grown to flowering and pollinated. Immature embryos are removed from the kernels and placed on an initiation medium. The embryos are typically between 1 and 4 mm in length, preferably between 1.5 and 3 mm, and most preferably between 2 and 2.5 mm. The initiation medium may be liquid, or solidified. Any initiation medium capable of inducing callus may be used. Some suitable examples include, but are not limited to those based on MS medium [Murashige, T., and Skoog, F., *Physiol. Plant.* 15, (1962) 473] N6 medium [Chu et al., *Scientia Sinica* 18 (1975) 659], B5 medium [Gamborg, O., et al., *Exp. Cell Res.*, 50 (1968) 151], SH medium or KM medium, with appropriate concentrations of sugars and plant growth regulators. Other suitable combinations are described in '*Plant Culture Media*' George, E. F., et al. (eds), Exegetics Ltd., Edington, Westbury, Wiltshire, England (1987).

The callus is removed from the cultured immature embryos and placed on maintenance medium. Any maintenance medium capable of sustaining callus proliferation may be used. Some suitable examples include but are not limited to those based on MS medium, N6 medium, B5 medium or KM medium, with appropriate concentrations of sugars and plant growth regulators. The material is subcultured to fresh maintenance medium at appropriate intervals, for example, every 1 to 120 days, preferably 3 to 21 days, and most preferably 5 to 14 days. Initiation and maintenance may be carried out in the light or dark, preferably in the dark. The temperature may be between 0° C. and 50° C., preferably between 20° C. and 32° C., most preferably between 25° C. and 28° C.

Figure 1:
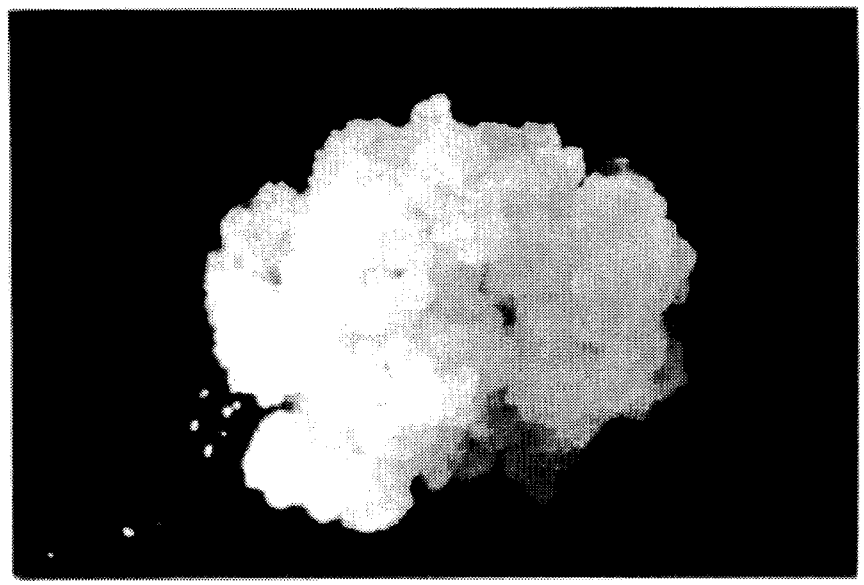
FIG. 1 shows callus that is suitable for use in initiating embryogenic suspensions of *Zea mays*. (Magnification approximately 7×). (Step a).

Subculturing is continued under the same conditions until the callus is a special type of callus. This special type of callus suitable for use in initiating suspensions in accordance with the invention is relatively non-mucilagenous, and is granular and friable. FIG. 1 shows callus that is suitable for use in initiating embryogenic suspensions in accordance with the invention. The suitable callus is subcultured at appropriate intervals, for example, every 1 to 120 days, preferably, 3 to 21 days, most preferably 5 to 14 days. Said special type of callus that is capable of regenerating fertile *Zea mays* plants and from which protoplasts capable of being regenerated into fertile plants can be isolated represents one of the preferred embodiments of the present invention.

Hence, the present invention relates to *Zea mays* callus which can produce suspension cultures from which plants, preferably fertile plants can be regenerated, and from which protoplasts capable of regenerating plants, preferably fertile plants, can be regenerated.

The present invention also relates to a method for producing a callus culture of *Zea mays* from which protoplasts can be isolated wherein the protoplasts are capable of being regenerated into fertile plants, which method comprises the steps of:

(a1) obtaining callus that is relatively non-mucilaginous, and is granular and friable on a callus-inducing or callus-maintaining medium, and (a2) growing the callus of step (a1) on a callus maintaining medium.

Step (b) through (d) suspension cultures.

The special type of callus from step (a) is placed in a liquid medium to form a suspension of cells and cell aggregates. Some suitable examples of liquid media include but are not limited to those based on MS medium, N6 medium, B5 medium and KM medium, with appropriate concentrations of sugars and plant growth regulators. Preferably the medium is N6 or KM medium.

Figure 2:
FIGS. 2 and 3 show densely cytoplasmic, dividing cells that are retained in the cultures of step b through d. (Magnification approximately 20×).
Figure 3:
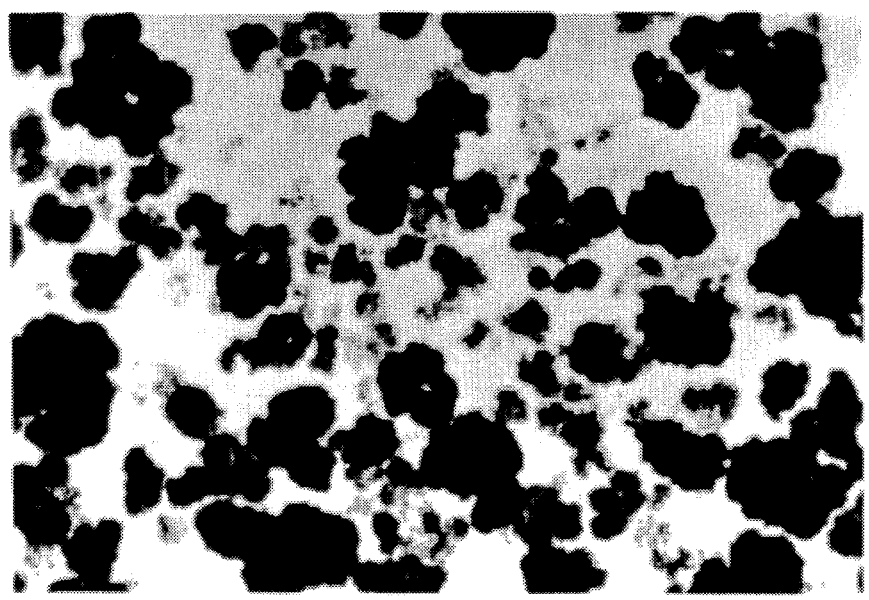

The cultures are subcultured with a frequency sufficient to maintain the cells and cell aggregates in a viable and proliferating state, for example, every 1 to 120 days, preferably, 3 to 21 days, most preferably 5 to 10 days. Cultures which contain aggregates of densely cytoplasmic, dividing cells are retained. Those with a high proportion of Expanded cells are discarded. The proportion of the cells which are densely cytoplasmic may increase with time; See FIGS. 2 and 3. The desired type of suspension culture is one containing preferably a proportion of at least 50%, and more preferably at least 70% of the cells in aggregates of dense, cytoplasmic dividing cells. The desired type of suspension culture is obtained after a suitable period of time, usually after about 7 days, preferably after about 30 days. The temperature and light conditions are the same as those for step (a). The suspension culture has been deposited in the ATCC, Rockville, Md., U.S.A., and has accession number 40326 [date of deposit: May 20, 1987].

Hence, the present invention provides a method for producing suspension cultures of *Zea mays* cells and cell aggregates from which protoplasts can be isolated, wherein the protoplasts are capable of regenerating fertile plants, comprising the steps of:

(a) obtaining callus that is relatively non-mucilaginous, and is granular and friable on a callus-inducing or callus-maintaining medium, (b) transferring the callus to a liquid medium to form a suspension of cells or cell aggregates, (c) subculturing the suspension (i) for a period of time (preferably for period of about 7 days) sufficient to obtain, in a viable, dividing stage protoplasts capable of being regenerated into fertile plants, and (ii) with a frequency sufficient to maintain any cells and cell aggregates in a viable state, and (d) selecting and retaining those cultures from the product of step (c) that contain aggregates of dense, cytoplasmic, dividing cells.

Step (e1) Producing protoplasts.

Protoplast isolation is carried out by incubating the callus or suspension culture cells and cell aggregates (obtained in accordance with steps (a) through (d) above) with an enzyme preparation which removes cell walls. Suitable enzyme preparations are known in the art. A particularly suitable enzyme preparation is, for example, a preparation containing 4% w/v RS cellulase (Yakult Pharmaceutical Ind. Co. Ltd., Shingikan Cho, Nishinomiya, Japan) with 1% w/v Rhozyme (Roban and Haas, Philadelphia, Pa., U.S.A.) in KMC salt solution (8.65 g/liter KCl; 12.5 g/liter $CaCl_2.2H_2O$; 16.47 g/liter $MgSO_4.7H_2O$; 5 g/liter MES; pH 5.6) is suitable. The digestion is carried out between 0° C. and 50° C., preferably between 10° C. and 35° C., most preferably between 26° C. and 32° C. The digestion is continued until protoplasts are released. The time required for digestion is typically between 30 minutes and 5 days, preferably between 1 hour and 1 day, most preferably between 3 and 5 hours.

Hence, the present invention is further directed to a method for producing *Zea mays* protoplasts capable of regenerating fertile plants, which method comprises the steps of:

(a) obtaining callus that is relatively non-mucilaginous, and is granular and friable on a callus-inducing or callus-maintaining medium, (b) transferring the callus to a liquid medium to-form a suspension of cells or cell aggregates, (c) subculturing the suspension (i) for a period of time (preferably for period of about 7 days) sufficient to obtain, in a viable, dividing stage protoplasts capable of being regenerated into fertile plants, and (ii) with a frequency sufficient to maintain any cells and cell aggregates in a viable state, and (d) selecting and retaining those cultures from the product of step (c) that contain aggregates of dense, cytoplasmic, dividing cells.

(e1) removing the cell walls with suitable enzymes, and isolating the resultant protoplasts.

The protoplasts released are collected and cleaned by standard methods such as filtration and centrifugation.

These protoplasts and the protoplast-derived cells (after regeneration of the cell wall) capable of regenerating fertile *Zea mays* plants are preferred subjects of the present invention.

Step (e2) Treating the protoplasts with exogenous DNA.

The protoplasts may be treated with exogenous DNA so as to produce cells that contain all or part of the exogenous DNA stably incorporated into their genetic material. Exogenous DNA is any DNA added to a protoplast. The exogenous DNA may contain a promoter active in *Zea mays*, or may utilize a promoter already present in the *Zea mays* genome. The exogenous DNA may be a chimeric gene, or a portion thereof. Treatment of the protoplasts with exogenous DNA can be carried out in accordance with the methods described in the following publications: [Paszkowski, J., et al. *The EMBO Journal* 3, No.12 (1984) 2717–2722; European Patent Application EP-0,164,575, (Paszkowski, J.,et al.); Shillito, R. D., et al., *Bio/Technology*, 3 (1985) 1099–1103; Potrykus, I., et al., *Mol. Gen. Genet.*, 199 (1985) 183–188; Loerz, H., et al., *Mol. Gen. Genet.*, 199 (1985) 178–182; Fromm, M. E., et al., *Nature*, 319 (1986) 791–793; British Patent Application GB-2,140,822 (Mettler, I. J.); and Negrutiu, I., et al., *Plant Mol. Biology*, 8 (1987) 363–373]. These publications are incorporated by reference.

The exogenous DNA may be added in any form such as, for example, naked linear or circular DNA, DNA encapsulated in liposomes, DNA in sphaeroplasts, DNA in other plant protoplasts, DNA complexed with salts, DNA in the form of nucleosomes, chromosomes or nuclei, or parts thereof, etc. Uptake of foreign DNA may be stimulated by any suitable method known in the art including the methods described in the references quoted above.

Primarily, the chimeric genes contemplated in this invention are those which provide the transformed plant protoplasts, protoplast-derived tissues and finally the protoplast-derived plants with new phenotypic traits (valuable properties), such as increased resistance to pests (e.g., Arthropods including insects and mites, nematodes etc.); increased resistance to pathogens (e.g. to phytopathogenic fungi, bacteria, viruses, etc.); increased resistance to chemicals [e.g. to herbicides (such as triazines, carbamates, ureas, dinitroanilides, sulfonylureas, imidazolinones, triazolo-pyrimidines, bialaphos, glyphosate, etc.), insecticides or other biocides]; increased resistance to cytotoxins (e.g. to hygromycin, kanamycin, chloramphenicol, etc.); increased resistance to adverse environmental (edaphic or atmospheric) influences (e.g. to heat, cold, wind, soil conditions, moisture, drought, etc.); with increased formation of desirable substances [for example, in the leaves, seeds, tubers, roots, stalks, etc.. Desirable substances produced by a genetically altered plant include proteins, starches, sugars, amino acids, alkaloids, flavors, colors, fats, etc.]; decreased formation of undesirable substances (e.g. toxins, protease inhibitors, undesirable flavors, undesirable proteins, fats, carbohydrates or secondary metabolites, etc.); or modified morphological or developmental phenotypic traits (e.g. altered height, growth habit, form, color, robustness, flowering time etc.).

Resistance to cytotoxins may be conferred by a gene expressing in the plant cells an enzyme that detoxifies the cytotoxin, for example, neomycin phosphotransferase type II or aminoglycoside phosphotransferase type IV for detoxification of kanamycin, hygromycin and other aminoglycoside antibiotics, or a glutathione-S-transferase or cytochrome P-450 or other catabolic enzyme known to detoxify triazine, sulfonylurea or other herbicides. Resistance to cytotoxins may also be conferred by a gene that expresses in a plant a form of a "target enzyme" (site of the action of the cytotoxin) which is resistant to the cytotoxin, for example, a form of acetohydroxyacid synthase which is insensitive to inhibition by sulfonylureas or imidazolinones, or other herbicide acting at this metabolic step, or a form of 5-enolpyruvylshikimate-3-phosphate (EPSP) synthase that is insensitive to inhibition by glyphosate. It can be advantageous to express these altered target enzymes in a form that allows their transport in the plant cell into the correct cellular compartment, i.e. the chloroplast in the above examples.

In certain cases it is advantageous to target the gene products into the mitochondria, the vacuoles, into endoplasmatic vesicles, or other cell parts or even into the intercellular (apoplastic) spaces.

Resistance to certain classes of fungi may be conferred by the introduction of a gene that expresses chitinase in the plant tissues. Many plant pathogenic fungi contain chitin as an integral part of hyphal and spore structure, including basidiomycetes (smuts and rusts) and ascomycetes and imperfect fungi (including Alternaria and Bipolaris, Exerohilum turcicum, Colletotricum, Gleocercospora and Cercospora). Chitinase can inhibit the growth of mycelia of certain pathogens in vitro. A plant leaf or root expressing chitinase is protected against many types of fungal attack.

Resistance to pests may be conferred by a gene encoding a pesticidal polypeptide.

Resistance to Arthropods may, for example, be conferred by a gene encoding a polypeptide that is toxic to larval or imaginal stages, or makes the plant unattractive to the larvae so that they reduce their feeding. A suitable gene in this context is the crystalline protein of Bt. A second class of protein which will confer insect resistance is protease inhibitors. Protease inhibitors are common constituents of plant storage structures [Ryan, C., *Ann. Rev. Plant Physiol.* 24 (1973) 173–196]. The inhibition of insect development has been attributed to the presence of trypsin inhibitors in the meal [Lipke, H., Fraenkel, G. S. and Liener, I. E., *J. Agr. Food Chem.* 2 (1954) 410–414]. Purified Bowman-Birk protease inhibitor isolated from soybean has been shown to inhibit gut proteases of *Tenebrio* larvae [Birk, Y., Gertler, A., and Khalef, S., *Biochem. Biophys. Acta* 67 (1963) 326–328]. The gene encoding cowpea trypsin inhibitor is described by Hilder et al., [*Nature,* 330 (1987) 160–163].

A gene encoding a protease inhibitor may be placed under the control of a plant promoter, preferably a constitutive promoter such as the Cauliflower mosaic virus (CaMV) 35S promoter, in a suitable vector such as the pCIB 710 vector described below.

The gene, for example the coding sequence for the soybean Bowman-Birk protease inhibitor, may be obtained using cDNA cloning methods described by Hammond et al., [*J. Biol. Chem.* 259 (1984) 9883–9890]. The appropriate clone can be identified either by immunoprecipitation of hybrid selected mRNA as described by Hammond et al. or by probing at low stringency with a synthetic oligonucleotide containing 50 or more bases from the 5' end of the coding sequence predicted from the amino acid sequence [amino acid sequences are compiled in Fasman, G., *Handbook of Biochemistry and Molecular Biology,* 2 (1976) 611–620]. For example, for cloning the gene for soybean Kunitz trypsin inhibitor the following oligonucleotide is used as the probe:

AA Asp Phe Val Leu Asp Asn Glu Gly Asn Pro Leu Glu Asn Gly probe 5'-GAC TTC GTT CTG GAC AAC GAA GGT AAC CCG CTG GAA AAC GGT Gly Thr Tyr Tyr Ile Leu Ser Asp Ile Thr Ala Phe Gly Gly GGT ACC TAC TAC ATC CTG TCC GAC ATC ACC GCT TTC GGT GGT-3'

The cloned DNA fragment may be sequenced using, for example, the Maxam and Gilbert [*Methods Enzymol.* 65 (1980) 499–560] method and the translational start site identified. If the cloned DNA fragment is longer than the coding sequence, the additional 5' and 3' sequences are resected with Bal 31. If the cloned DNA fragment is shorter than the coding sequence, the cloned DNA is used as the primer for primer extension with mRNA [Maniatis et al., *Molecular Cloning: A Laboratory Manual,* (1982), Cold Spring Harbor, N.Y.] and the extended DNA recloned.

Appropriate linkers are added to the DNA encoding the protein and the fragment inserted into the chosen vector (cassette), for example pCIB 710, so that the gene is under the control of the desired promoter (CaMV 35S in pCIB 710).

An alternative method of obtaining a gene for protease inhibitors with less than 100 amino acids, such as the lima bean trypsin inhibitor, is to synthesize it. The coding sequence is predicted by back-translation and restriction sites appropriate for the desired vector included at each end. The synthetic gene is prepared by synthesizing overlapping oligonucleotides of 30 to 60 bases. These fragments are kinased, ligated [Maniatis et al, supra] and cloned into the appropriate vector.

A clone whose insert is in the correct orientation may be identified by sequencing. Plasmid DNA is isolated and used for incorporation into maize protoplasts.

Hence, the present invention also provides a method wherein the method as described under step (a) through (g) further comprises the step of:

(e2) treating the protoplasts of step (e1) capable of being regenerated into fertile plants, with exogenous DNA so as to produce cells that contain all or part of the exogenous DNA stably incorporated into their genetic material.

*Zea mays* protoplasts or protoplast-derived cells (after regeneration of the cell wall) cells capable of regenerating fertile plants, and especially *Zea mays* protoplasts and cells having stably incorporated exogenous DNA, preferably exogenous DNA expressible in *Zea mays*, are further preferred subjects of the present invention.

Especially preferred are *Zea mays* protoplasts or protoplast-derived cells (after regeneration of the cell wall) cells wherein the exogenous DNA, normally a chimeric gene, provides the transformed plant with a valuable property, such as increased resistance to pests (e.g., Arthropods including insects and mites, nematodes etc.); increased resistance to pathogens (e.g. to phytopathogenic fungi, bacteria, viruses, etc.); increased resistance to chemicals [e.g. to herbicides (such as triazines, carbamates, ureas, dinitroanilides, sulfonylureas, imidazolinones, triazolo-pyrimidines, bialaphos, glyphosate, etc.), insecticides or other biocides]; increased resistance to cytotoxins (e.g. to hygromycin, kanamycin, chloramphenicol, etc.); increased resistance to adverse environmental (edaphic or atmospheric) influences (e.g. to heat, cold, wind, soil conditions, moisture, drought, etc.); with increased formation of desirable substances [for example, in the leaves, seeds, tubers, roots, stalks, etc.. Desirable substances produced by a genetically altered plant include proteins, starches, sugars, amino acids, alkaloids, flavors, colors, fats, etc.]; decreased formation of undesirable substances (e.g. toxins, protease inhibitors, undesirable flavors, undesirable proteins, fats, carbohydrates or secondary metabolites, etc. ); or modified morphological or developmental phenotypic traits (e.g. altered height, growth habit, form, color, robustness, flowering time etc.) .

Especially preferred within the transgenic *Zea mays* protoplasts or protoplast-derived cells are those protoplasts or cells wherein the stably incorporated exogenous DNA is a chimeric gene that codes for a polypeptide having substantially the insect toxicity properties (insecticidal activity) of a Bt crystal protein.

Step (f) Plating the protoplasts.

The protoplasts are plated for culture either with or without treatment with DNA in a liquid or solidified culture medium. Some examples of suitable culture media include but are not limited to those based on KM medium, N6 medium, B5 medium and MS medium, with appropriate concentrations of sugars and plant growth regulators. The preferred medium is KM medium containing a solidifying agent. The preferred solidifying agent is agarose, especially SeaPlaque® agarose [European patent application EP-0, 129,668, Shillito, R. D., et al., (1984)]. Where used, the concentration of SeaPlaque® agarose may be between 0.1% and 2.5% w/v, preferably between 0.6% and 1.5% w/v. The optimum concentration of other solidifying agents may vary, but can be easily determined.

The medium in which the protoplasts are usually cultured in the presence of suitable plant growth regulators (such as auxins and/or cytokinins, etc.) to assist the protoplasts to divide and form colonies. Suitable plant growth regulators include but are not limited to 2,4-dichlorophenoxyacetic acid (2,4-D), 3,6-di-chloro-2-methoxybenzoic acid (dicamba) , 4-amino-3,6,6-trichloro-picolinic acid(picloram) , and para-chlorophenoxyacetic acid (pCPA). The amount of the growth regulator is a growth regulatingly effective non-toxic amount. The concentration of such plant growth regulators is usually in the range of 0.01 to 100 mg/liter, preferably 0.1 to 100 mg/liter, more preferably 0.1 to 10 mg/liter, most preferably 0.3 to 3 mg/liter.

Surprisingly, it has been found that O-loweralkanoyl-salicylic acids (O-acetyl-salicylic acid and its homologs) alone or in combination with plant growth regulators and/or DMSO promote division of, or colony formation from, plant protoplasts, preferably protoplasts of *Zea mays*. The term "loweralkanoyl" represents alkanoyl groups having 1–7, preferably 1–4, most preferably 2–3 carbon atoms.

Preferred O-loweralkanoyl-salicylic acids are 0-acetyl-salicylic acid and O-propionyl-salicylic acid, preferably O-acetyl-salicylic acid.

The amount of the O-loweralkanoyl-salicylic acid is an amount sufficient to promote cell division or colony formation. It is preferably a growth regulatingly effective non-toxic amount. Suitable concentrations of the O-loweralkanoyl-salicylic acid are in the range of 0.1 to 3000 mg/liter, preferably in the range of 10 to 300 mg/liter, more preferably 10 to 100 mg/liter, and most preferably about 100 mg/liter.

The amount of DMSO is an amount sufficient to promote cell division or colony formation. Suitable concentrations of DMSO are in the range of 0 to 3%, preferably 0.01 to 2%, more preferably 0.1 to 1%.

Hence, the present invention provides a method for increasing division of, or colony formation from plant protoplasts, preferably *Zea mays* protoplasts, comprising culturing the protoplasts in the presence of a growth regulatingly effective non-toxic amount of a O-loweralkanoyl-salicylic acid sufficient to promote cell division or colony formation.

In a preferred embodiment of the present invention said method further comprises the presence of 0.01 to 100 mg/liter, preferably 0.1 to 100 mg/liter, more preferably 0.1 to 10 mg/liter, most preferably 0.3 to 3 mg/liter of a plant growth regulator.

In a further preferred embodiment of the present invention said method further comprises the presence of an amount of DMSO sufficient to promote cell division or colony formation. Preferred amounts of DMSO are between 0 and 3%, preferably 0.01 and 2%, preferably between 0.1 and 1%.

This method for increasing division of, or colony formation from protoplasts is suitable for all plant protoplasts and not restricted to *Zea mays*. It is especially suitable for the Angiospermae, and Gymnospermae, for example, the following plant families; Solanaceae, Cruciferae, Compositae, Liliaceae, Vitaceae, Chenopodiaceae, Rutaceae, Bromeliaceae, Rubidiaceae, Theaceae, Musaceae or Gramineaceae and of the order Leguminoseae, in particular of the family Papilionaceae. Preferred plants are representatives of the Solanaceae, Cruciferae and Gramineae.

The medium in which the protoplasts are cultured may contain medium which has previously been conditioned by the growth of suitable cells, for example, *Zea mays* or *Dactylis glomerata*.

The protoplasts may be cultured in the solid or the liquid medium without subculture for a period of up to 12 weeks, preferably up to 6 weeks, most preferably in the range of 3 to 4 weeks. Alternatively, a solid medium can be placed in liquid medium, as described in European patent application EP-0,129,668, Shillito, R. D., et al., (1984), or treated in some other manner to assist division of, and/or colony formation from, the protoplasts. One suitable manner is culture in association with nurse cells as described by Shneyour et al. [*Plant Science Lett.*, 33 (1984) 293] and Smith et al. [*Plant Science Lett.*, 36 (1984) 67], and in example 8s.

The protoplasts are cultured in the light or, preferably, in the dark at a temperature between 0° C. and 50° C., preferably between 20° C. and 32° C., most preferably between 25° C. and 28° C. The light intensity is typically between 0.1 and 200 µE/m²sec (micro Einsteins/m² second), preferably between 0.1 and 100 µE/m²sec, more preferably between 30 and 90 µE/m²sec, most preferably between 10 and 40 µE/m²sec.

Figure 4:
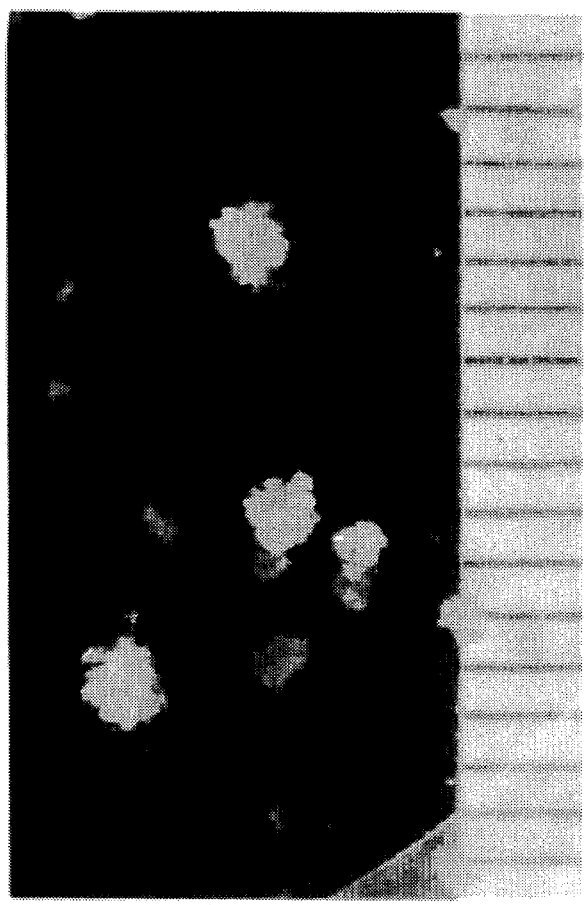
FIG. 4 shows calli developing from protoplasts cultured in solid medium. (Magnification approximately 7×).
Figure 5:
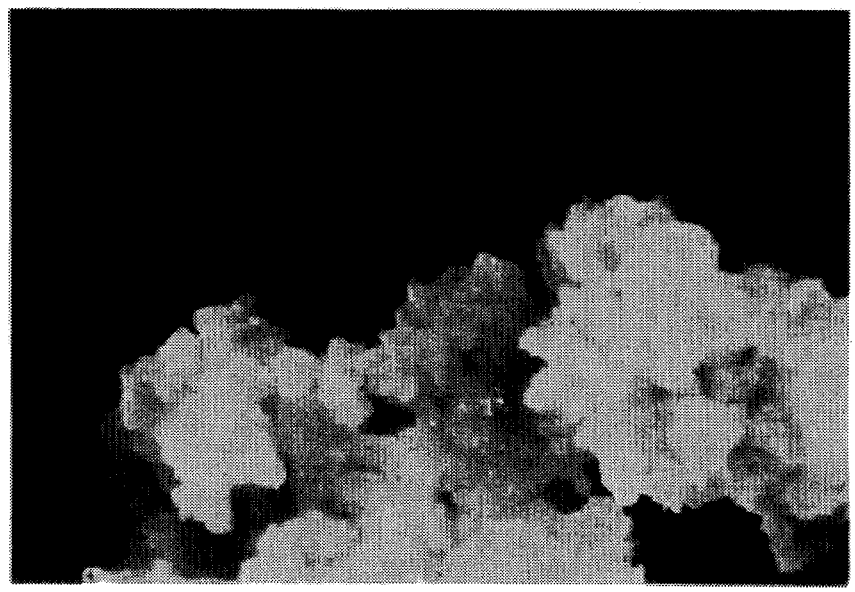
FIG. 5 shows callus derived from protoplasts according to step f. (Magnification approximately 7×).

FIG. 4 shows calli developing from protoplasts cultured in solid medium and FIG. 5 shows callus derived from protoplasts according to step (f). This callus can be subcultured on maintenance medium, as described for callus in step (a), and then subcultured onto regeneration medium according to step (g), or can be directly subcultured onto regeneration medium according to step (g).

Step (g) Regeneration of a plantlet.

Figure 6:
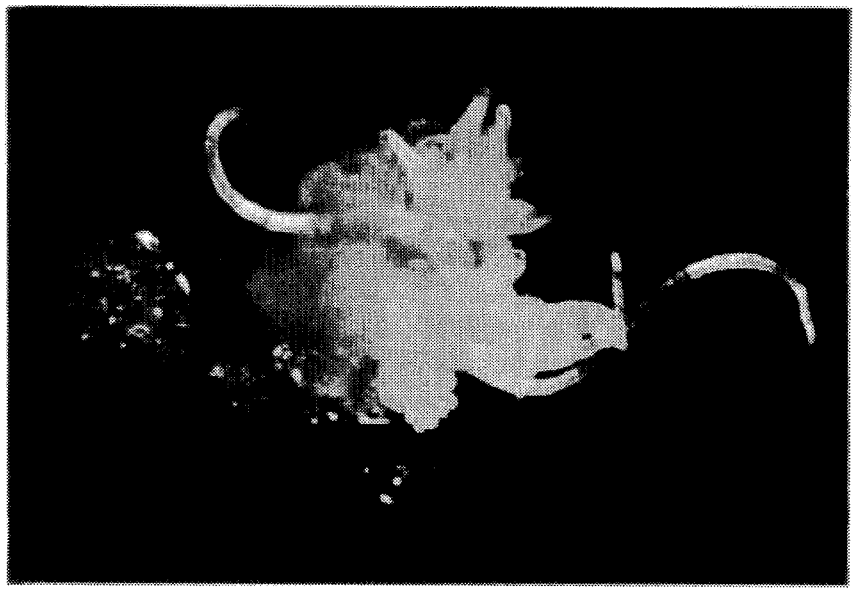
FIG. 6 shows further differentiation of the callus to form a plantlet according to step g. (Magnification approximately 7×).

Callus which forms from protoplasts according to step (f) is subcultured one or more times on suitable media so as to regenerate a fertile plant. Some examples of suitable culture media include but are not limited to those based on N6 medium, B5 medium, MS medium, or KM medium with appropriate concentrations of sugars, plant growth regulators, and optionally DMSO. A preferred medium is N6 or MS medium without growth regulators, or containing a cytokinin and/or other plant growth regulators stimulating the regeneration of plantlets and/or containing a O-loweralkanoyl-salicylic acid, optionally in further combination with DMSO, as described above in step (f). The callus appears to contain differentiated cells and cell aggregates (FIG. 6) after a suitable period of time, typically 1 week to 6 months, more typically 1 to 3 months. The callus differentiates further to form a plantlet after a suitable further period of time, typically 1 week to 6 months, more typically 1 to 3 months.

The callus is cultured at this stage in the light. The light intensity is typically between 0.1 and 100 µE/m²sec, preferably between 30 and 80 µE/m²sec.

Especially preferred is a method wherein the cells or the callus form embryos or proembryos before they regenerate plantlets.

Step (h) Obtaining a fertile plant from a plantlet.

Plantlets are transferred to a suitable medium, for example, N6 or MS medium without plant growth regulators. Alternatively, a growth regulator stimulating root or shoot growth may be added. The plantlets are cultured on this medium until they form roots. The time required for root formation is typically 1 to 6 weeks, more typically about 2 weeks. When the root and shoot have sufficiently grown, the plants are transferred to soil, and gently hardened off. A sufficient length for the roots at this stage is in the range of 1 to 10 cm, more typically 2 to 5 cm, and for the shoot is in the range of 1 to 15 cm, more typically 2 to 10 cm.

The plants are grown to flowering and sexual progeny or vegative propagules obtained in the usual way.

Transgenic corn plant cells containing exogenous DNA may be maintained in culture or may be regenerated into plants. Corn plant cells into which exogenous DNA may be introduced include any corn plant cell capable of accepting, replicating, and expressing foreign genes at a suitable level. Some suitable corn plant cells include, for example, cells isolated from the inbred lines Funk 5N984, Funk 5N986, Funk 2717, Funk 211D, Funk 2N217A, B73, A632, CM105, B37, B84, B14, Mo17, R168, MS71, A188, FA91, A641 and W117. Preferred are all elite genotypes. More preferred are all inbred lines. Most preferred are all elite inbred lines, especially the elite inbred lines Funk 5N984, Funk 5N986, Funk 2717, Funk 211D or Funk 2N217A, and most preferably Funk 2717.

The culture medium capable of sustaining a particular plant cell in culture may depend on the genotype of corn plant cell used. For example, some suitable media include, but are not limited to those based on MS [Murashige and Skoog (1962)]; N6 [Chu et al. (1975)]; B5 [Gamborg et al (1968)]; and KM (Kao and Michayluk (1975)] media with appropriate concentrations of sugars and plant growth regulators.

Thus, the present invention provides a method for regenerating Zea mays plants from protoplasts comprising the steps of:

(e1) producing protoplasts capable of being regenerated into fertile plants from the cells, and cell aggregates of step (d), (f) plating the protoplasts in a suitable medium in which the protoplasts divide and form cells, (g) subculturing the cells resulting from step (f) so as to regenerate plantlets, and (h) culturing the plantlets on a growing medium to obtain fertile plants.

Preferred is a method wherein the Zea mays protoplasts contain stably incorporated exogenous DNA, preferably exogenous DNA expressible in Zea mays plants. More preferred is a method wherein the Zea mays protoplasts are cultured in the presence of 0.01 to 100 mg/liter of a plant growth regulator (preferably 2,4-D, dicamba, picloram or pCPA, most preferably 2,4-D) and in the presence of an amount of a O-loweralkanoyl-salicylic acid (preferably O-acetyl-salicylic acid or O-propionyl-salicylic acid, most preferably O-acetyl-salicylic acid) sufficient to promote cell division or colony formation. Most preferred is a method comprising further the presence of an amount of DMSO sufficient to promote cell division or colony formation.

The present invention also provides a method for producing transgenic Zea mays protoplasts capable of being regenerated into fertile transgenic plants comprising treating Zea mays protoplasts capable of being regenerated into fertile plants with exogenous DNA so as to produce cells that contain all or part of the exogenous DNA incorporated in their genetic material.

Furthermore, the present invention is directed to Zea mays plants and propagules thereof regenerated from protoplasts or protoplast-derived cells and to the progeny thereof. Preferred are those regenerated plants, propagules and progeny thereof having stably incorporated exogenous DNA, preferably exogenous DNA expressible in Zea mays. Suitable exogenous DNAs are, for example, the chimeric genes described previously or subsequently. The term "propagules" includes any plant material capable of being sexually or asexually propagated, or being propagated in-vivo or in-vitro. Such propagules preferably consist of the protoplasts, cells, calli, tissues, embryos or seeds of the regenerated plants. The progeny of the regenerated plants and of the regenerated transgenic plants includes mutants and variants.

DETAILED DESCRIPTION (PART B) INSECTICIDAL CORN (ZEA MAYS) PLANTS

The present invention is directed to the production of a chimeric Bt toxin gene. The corn plant cells contemplated include cells from all genotypes (varieties, cultivars, inbred lines, hybrids, etc.) of corn plants into which foreign DNA can be introduced, replicated and expressed. Some examples of suitable corn plant genotypes include but are not restricted to inbred lines such as Funk 2717, Funk 211D, Funk 2N217A, B73, A632, CM105, B37, B84, B14, Mo17, R168, MS71, A188, FA91, A641 and W117. Funk 5N984 and Funk 5N986 are further examples of useful Zea mays genotypes. Preferably the genotype is an elite genotype, more preferably an elite inbred line selected from the group consisting of Funk 5N984, Funk 5N986, Funk 2717, Funk 211D or Funk 2N217A, and most preferably it is the elite inbred line Funk 2717.

The chimeric gene of this invention contains a promoter region that functions efficiently in corn plants and a coding region that codes for the crystal protein from Bt or for a polypeptide having substantially the insecticidal properties of the crystal protein from Bt. The coding sequence of the chimeric gene is not known to be associated with said promoter in natural genes.

The 5' and/or 3' untranslated regions may, independently, be associated in nature with either the promoter or the coding region, or with neither the promoter nor the coding region. Preferably, either the 5' or the 3' untranslated region is associated with the promoter in natural genes, and most preferably both the 5' and 3' regions are associated with the promoter in natural genes.

One could not predict, based on the state of the art at the time this invention was made, that corn cells would express an insecticidal polypeptide at any level, and especially at sufficient levels to impart insecticidal properties to the cells. In particular, a polypeptide as large and as insoluble as the polypeptide having the insect toxicity properties of Bt crystal protein was expected to be especially difficult to express in plant cells.

In order to be considered insecticidal, the plant cells must contain an insecticidal amount of toxin having substantially the insecticidal activity of the crystal protein from Bt. An insecticidal amount is an amount which, when present in plant cells, kills insect larvae or at least reduces their feeding substantially.

The Gene

The Transcription Control Sequences

The chimeric gene of this invention contains transcription control sequences comprising promoter and 5' and 3' untranslated sequences that are functional in corn plants. These sequences may, independently, be derived from any source, such as, virus, plant or bacterial genes.

The virus promoters and 5' and 3' untranslated sequences suitable for use are functional in corn plants and are obtained, for example, from plant viruses such as Cauliflower mosaic virus (CaMV). Cauliflower mosaic virus has been characterized and described by Hohn et al in *Current Topics in Microbiology and Immunology*, 96, (1982) 194–220 and appendices A to G. This description is incorporated herein by reference.

CaMV is an atypical plant virus in that it contains double-stranded DNA. At least two CaMV promoters are functional in plants, namely the 19S promoter, which results in transcription of gene VI of CaMV, and the promoter of the 35S transcript. The 19S promoter and the 35S promoter are the preferred plant virus promoters for use in the present invention.

CaMV 19S promoters and 5' untranslated regions may be obtained by means of a restriction map such as the map described in FIG. 4 on page 199 of the Hohn et al article mentioned above, or from the sequence that appears in Appendix C of the Hohn et al article.

In order to isolate the CaMV 19S promoter and, optionally, the adjacent 5' untranslated region, a restriction fragment of the CaMV genome containing the desired sequences is selected. A suitable restriction fragment that contains the 19S promoter and the 5' untranslated region is the fragment between the PstI site starting at position 5386 and the HindIII site starting at position 5850 of FIG. 4 and appendix C of the Hohn et al article.

By analogous methods, the 35S promoter from CaMV may be obtained, as is described in example 6 below.

Undesired nucleotides in the restriction fragment may optionally be removed by standard methods. Some suitable methods for deleting undesired nucleotides include the use of exonucleases [Maniatis et al, *Molecular Cloning*, Cold Spring Harbor Laboratory, (1982) 135–139] and oligonucle-otide-directed mutagenesis [Zoller and Smit, *Meth. Enzymol.*, 100 (1983) 468–500].

A similar procedure may be used to obtain a desirable 3' untranslated region. For example, a suitable CaMV 19S gene 3' untranslated sequence may be obtained by isolating the region between the EcoRV site at position 7342 and the BglII site at position 7643 of the CaMV genome as described in FIG. 4 and appendix C of the Hohn et al article.

Examples of plant gene promoters and 5' and 3' untranslated regions suitable for use in the present invention also include those of the gene coding for the small subunit of ribulose hisphosphate carboxylase and chlorophyll a/b-binding protein. These plant gene regions may be isolated from plant cells in ways comparable to those described above for isolating the corresponding regions from CaMV; see Morelli et al., *Nature*, 315 (1985) 200–204.

Suitable promoters and 5' and 3' untranslated regions from bacterial genes include those present in the T-DNA region of Agrobacterium plasmids. Some examples of suitable Agrobacterium plasmids include the Ti plasmid of *A. tumefaciens* and the Ri plasmid of *A. rhizogenes*. The Agrobacterium promoters and 5' and 3' untranslated regions useful in the present invention are, in particular, those present in the genes coding for octopine synthase and nopaline synthase. These sequences may be obtained by methods similar to those described above for isolating CaMV and plant promoters and untranslated sequences; see Bevan et al., *Nature* 304 (1983) 184–187.

The Coding Region

The coding region of the chimeric gene contains a nucleotide sequence that codes for a polypeptide having substantially the toxicity properties of a Bt delta-endotoxin crystal protein. A polypeptide, for the purpose of the present invention, has substantially the toxicity properties of Bt delta-endotoxin crystal protein if it is insecticidal to a similar range of insect larvae as is the crystal protein from a subspecies of Bt. Some suitable subspecies include, for example, Bt var. kurstaki; Bt var. berliner; Bt var. alesti; Bt var. tolworthi; Bt var. sotto; Bt var. dandrolimus; Bt var. tenebrionis; Bt var. san diego; and Bt. var. aizawai. The preferred subspecies is Bt var. kurstaki, and especially Bt var. kurstaki HD1.

The coding region may exist naturally in Bt. Alternatively, the coding region may contain a sequence that is different from the sequence that exists in Bt but is equivalent because of the degeneracy of the genetic code.

The coding sequence of the chimeric gene may also code for a polypeptide that differs from a naturally occurring crystal protein delta-endotoxin but that still has substantially the insect toxicity properties of the crystal protein. Such a coding sequence will usually be a variant of a natural coding region. A "variant" of a natural DNA sequence is a modified form of the natural sequence that performs the same function. The variant may be a mutation, or may be a synthetic DNA sequence, and is substantially homologous to the corresponding natural sequence. "Substantial sequence homology" should be understood as referring to either: a DNA fragment having a nucleotide sequence sufficiently similar to another DNA fragment to produce a protein having similar properties; or a polypeptide having an amino acid sequence sufficiently similar to another polypeptide to exhibit similar properties. Normally, a DNA sequence is substantially homologous to a second DNA sequence if at least 70%, preferably at least 80%, and most preferably at least 90% of the active portions of the DNA sequence are homologous. Two different nucleotides are considered to be homologous in a DNA sequence of a coding region for the purpose of determining substantial homology if the substitution of one for the other constitutes a silent mutation.

The invention thus includes any chimeric gene coding for a sequence of amino acids having the insecticidal properties satisfying the requirement disclosed and claimed. It is preferred that the nucleotide sequence is substantially homologous at least to that portion or to those portions of the natural sequence responsible for insecticidal activity.

The polypeptide expressed by the chimeric gene of this invention will generally also share at least some immunological properties with a natural Bt crystal protein, since it has at least some of the same antigenic determinants.

Accordingly, the polypeptide coded for by the chimeric gene of the present invention is preferably structurally related to the delta-endotoxin of the crystal protein produced by Bt. Bt produces a crystal protein with a subunit which is a protoxin having an Mr of about 130,000 to 140,000. This subunit can be cleaved by proteases or by alkali to form insecticidal fragments having an Mr as low as 50,000, and possibly even lower. Chimeric genes that code for such fragments of the protoxin or for even smaller portions thereof according to the present invention can be constructed as long as the fragment or portions of fragments have the requisite insecticidal activity. The protoxin, insecticidal fragments of the protoxin and insecticidal portions of these fragments can be fused to other molecules such as polypeptides.

Coding regions suitable for use in the present invention may be obtained from crystal protein toxin genes isolated from Bt, for example, see Whiteley et al., PCT application WO 86,01536 and U.S. Pat. Nos. 4,448,885 and 4,467,036. A preferred sequence of nucleotides that codes for a crystal protein is that shown as nucleotides 156 to 3623 in the sequence of the formula (I) or a shorter sequence that codes for an insecticidal fragment of such a crystal protein; Geiser et al., *Gene*, 48 (1986) 109–118 [see the nucleotide sequence of the formula (I) in FIG. 13].

Hence, the present invention is also directed to the gene having the nucleotide sequence of the formula (I), to genes having substantially sequence homology to the gene of the formula (I), and genes coding for a polypeptide having the sequence of the formula (II) or having substantially sequence homology to the sequence of the formula (II); and preferably to those of these genes which are expressible in plants, most preferably in *Zea mays*.

The coding region defined by nucleotides 156 to 3623 of the sequence (I) encodes the polypeptide of the sequence of the formula (II).

SEQUENCE OF THE FORMULA (II)

20
Met Asp Asn Asn Pro Asn Ile Asn Glu Cys Ile Pro Tyr Asn Cys Leu Ser Asn Pro Glu

40
Val Glu Val Leu Gly Gly Glu Arg Ile Glu Thr Gly Tyr Thr Pro Ile Asp Ile Ser Leu

60
Ser Leu Thr Gln Phe Leu Leu Ser Glu Phe Val Pro Gly Ala Gly Phe Val Leu Gly Leu

80
Val Asp Ile Ile Trp Gly Ile Phe Gly Pro Ser Gln Trp Asp Ala Phe Pro Val Gln Ile

100
Glu Gln Leu Ile Asn Gln Arg Ile Glu Glu Phe Ala Arg Asn Gln Ala Ile Ser Arg Leu

120
Glu Gly Leu Ser Asn Leu Tyr Gln Ile Tyr Ala Glu Ser Phe Arg Glu Trp Glu Ala Asp

140
Pro Thr Asn Pro Ala Leu Arg Glu Glu Met Arg Ile Gln Phe Asn Asp Met Ash Ser Ala

160
Leu Thr Thr Ala Ile Pro Leu Phe Ala Val Gln Asn Tyr Gln Val Pro Leu Leu Ser Val

180
Tyr Val Gln Ala Ala Asn Leu His Leu Ser Val Leu Arg Asp Val Ser Val Phe Gly Gln

200
Arg Trp Gly Phe Asp Ala Ala Thr Ile Asn Ser Arg Tyr Asn Asp Leu Thr Arg Leu Ile

220
Gly Asn Tyr Thr Asp His Ala Val Arg Trp Tyr Asn Thr Gly Leu Glu Arg Val Trp Gly
Pro Asp Ser Arg Asp Trp Ile Arg Tyr Asn Gln Phe Arg Arg Glu Leu Thr Leu Thr Val

260
Leu Asp Ile Val Ser Leu Phe Pro Asn Tyr Asp Ser Arg Thr Tyr Pro Ile Arg Thr Val

280
Ser Gln Leu Thr Arg Glu Ile Tyr Thr Asn Pro Val Leu Glu Asn Phe Asp Gly Ser Phe

300
Arg Gly Ser Ala Gln Gly Ile Glu Gly Ser Ile Arg Ser Pro His Leu Met Asp Ile Leu

320
Asn Ser Ile Thr Ile Tyr Thr Asp Ala His Arg Gly Glu Tyr Tyr Trp Ser Gly His Gln

340
Ile Met Ala Ser Pro Val Gly Phe Ser Gly Pro Glu Phe Thr Phe Pro Leu Tyr Gly Thr

360
Met Gly Asn Ala Ala Pro Gln Gln Arg Ile Val Ala Gln Leu Gly Gln Gly Val Tyr Arg

380
Thr Leu Ser Ser Thr Leu Tyr Arg Arg Pro Phe Asn Ile Gly Ile Asn Asn Gln Gln Leu

400
Ser Val Leu Asp Gly Thr Glu Phe Ala Tyr Gly Thr Ser Ser Asn Leu Pro Ser Ala Val

420
Tyr Arg Lys Ser Gly Thr Val Asp Ser Leu Asp Glu Ile Pro Pro Gln Asn Asn Asn Val

440
Pro Pro Arg Gln Gly Phe Ser HIS Arg Leu Ser His Val Ser Met Phe Arg Ser Gly Phe
Ser Asn Ser Ser Val Ser Ile Ile Arg Ala Pro Met Phe Ser Trp Ile His Arg Ser Ala

480
Glu Phe Asn Asn Ile Ile Pro Ser Ser Gln Ile Thr Gln Ile Pro Leu Thr Lys Ser Thr

500
Asn Leu Gly Ser Gly Thr Ser Val Val Lys Gly Pro Gly Phe Thr Gly Gly Asp Ile Leu

520
Arg Arg Thr Ser Pro Gly Gln Ile Ser Thr Leu Arg Val Asn Ile Thr Ala Pro Leu Ser

540
Gln Arg Tyr Arg Val Arg Ile Arg Tyr Ala Ser Thr Thr Asn Leu Gln Phe His Thr Ser

560
Ile Asp Gly Arg Pro Ile Asn Gln Gly Asn Phe Ser Ala Thr Met Ser Ser Gly Ser Asn

580
Leu Gln Ser Gly Ser Phe Arg Thr Val Gly Phe Thr Thr Pro Phe Asn Phe Ser Asn Gly

600
Ser Ser Val Phe Thr Leu Ser Ala His Val Phe Asn Ser Gly Asn Glu Val Tyr Ile Asp

620

Arg Ile Glu Phe Val Pro Ala Glu Val Thr Phe Glu Ala Glu Tyr Asp Leu Glu Arg Ala

640

Gln Lys Ala Val Asn Glu Leu Phe Thr Ser Ser Asn Gln Ile Gly Leu Lys Thr Asp Val

660

Thr Asp Tyr His Ile Asp Gln Val Ser Asn Leu Val Glu Cys Leu Ser Asp Glu Phe Cys

680

Leu Asp Glu Lys Lys Glu Leu Ser Glu Lys Val Lys His Ala Lys Arg Leu Ser Asp Glu

700

Arg Asn Leu Leu Gln Asp Pro Asn Phe Arg Gly Ile Ash Arg Glu Leu Asp Arg Gly Trp

720

Arg Gly Ser Thr Asp Ile Thr Ile Gln Gly Gly Asp Asp Val Phe Lys Glu Asn Tyr Val

740

Thr Leu Leu Gly Thr Phe Asp Glu Cys Tyr Pro Thr Tyr Leu Tyr Gln Lys Ile Asp Glu

760

Ser Lys Leu Lys Ala Tyr Thr Arg Tyr Gln Leu Arg Gly Tyr Ile Glu Asp Ser Gln Asp

780

Leu Glu Ile Tyr Leu Ile Arg Tyr Asn Ala Lys His Glu Thr Val Asn Val Pro Gly Thr

800

Gly Ser Leu Trp Pro Leu Ser Ala Pro Ser Pro Ile Gly Lys Cys Ala His His Ser His

820

His Phe Ser Leu Asp Ile Asp Val Gly Cys Thr Asp Leu Asn Glu Asp Leu Gly Val Trp

840

Val Ile Phe Lys Ile Lys Thr Gln Asp Gly His Ala Arg Leu Gly Asn Leu Glu Phe Leu

860

Glu Glu Lys Pro Leu Val Gly Glu Ala Leu Ala Arg Val Lys Arg Ala Glu Lys Lys Trp

880

Arg Asp Lys Arg Glu Lys Leu Glu Trp Glu Thr Asn Ile Val Tyr Lys Glu Ala Lys Glu

900

Ser Val Asp Ala Leu Phe Val Asn Ser Gln Tyr Asp Arg Leu Gln Ala Asp Thr Asn Ile

920

Ala Met Ile His Ala Ala Asp Lys Arg Val His Ser Ile Arg Glu Ala Tyr Leu Pro Glu

940

Leu Ser Val Ile Pro Gly Val Asn Ala Ala Ile Phe Glu Glu Leu Glu Gly Arg Ile Phe

960

Thr Ala Phe Ser Leu Tyr Asp Ala Arg Asn Val Ile Lys Asn Gly Asp Phe Asn Asn Gly

980

Leu Ser Cys Trp Asn Val Lys Gly His Val Asp Val Glu Glu Gln Asn Ash His Arg Ser

1000

Val Leu Val Val Pro Glu Trp Glu Ala Glu Val Ser Gln Glu Val Arg Val Cys Pro Gly

1020

Arg Gly Tyr Lie Leu Arg Val Thr Ala Tyr Lys Glu Gly Tyr Gly Glu Gly Cys Val Thr

1040

Ile His Glu Ile Glu Asn Asn Thr Asp Glu Leu Lys Phe Ser Asn Cys Val Glu Glu Glu

1060

Val Tyr Pro Asn Asn Thr Val Thr Cys Asn Asp Tyr Thr Ala Thr Gln Glu Glu Tyr Glu

1080

Gly Thr Tyr Thr Ser Arg Asn Arg Gly Tyr Asp Gly Ala Tyr Glu Set Asn Ser Ser Val

1100

Pro Ala Asp Tyr Ala Ser Ala Tyr Glu Glu Lys Ala Tyr Thr Asp Gly Arg Arg Asp Asn

1120

Pro Cys Glu Ser Asn Arg Gly Tyr Gly Asp Tyr Thr Pro Leu Pro Ala Gly Tyr Val Thr

1140

Lys Glu Leu Glu Tyr Phe Pro Glu Thr Asp Lys Val Trp Ile Glu Ile Gly Glu Thr Glu

1166

Gly Thr Phe Asn Val Asp Ser Val Glu Leu Leu Leu Met Glu Glu End

Hence, the present invention is further directed to the polypeptide having the sequence of the formula (II) or to insecticidal parts of this polypeptide.

Furthermore, it has been shown that some Bt strains are toxic to other than lepidopteran insects. Specifically the Bt var. tenebrionis is toxic to coleopteran insects. The toxicity of Bt strain san diego toward coleopteran insects and the sequence of the associated toxin gene is discussed by Herrnstadt and Soares in EP-O,202,739 and EP-O,213,818.

Vectors

In order to introduce the chimeric gene of the present invention into plant cells, the gene is first inserted into a vector. If the gene is not available in an amount sufficient for transformation, the vector may be amplified by replication in a host cell. The most convenient host cells for amplification are bacterial or yeast cells. When a sufficient amount of the chimeric gene is available, it is introduced into corn protoplasts according to the present invention. The introduction of the gene into corn plants may be by means of the same vector used for replication, or by means of a different vector.

Some examples of bacterial host cell suitable for replicating the chimeric gene include those of the genus Escherishia such as *E. coli* and Agrobacterium such as *A. tumefaciens* or *A. rhizogenes*. Methods of cloning heterologous genes in bacteria are described by Cohen et al, U.S. Pat. Nos. 4,237,224 and 4,468,464.

The replication of genes coding for the crystal protein of Bt in *E. Coli* is described in Wong et al., *J. Biol. Chem.* 258 (1983) 1960–1967.

Some examples of yeast host cells suitable for replicating the genes of this invention include those of the genus Saccharomyces.

Any vector into which the chimeric gene can be inserted and which replicates in a suitable host cell, such as in bacteria or yeast, may be used to amplify the genes of this invention. The vector may, for example, be derived from a phage or a plasmid. Some examples of vectors derived from phages useful in the invention include those derived from M13 and from lambda. Some suitable vectors derived from M13 include M13mp18 and M13mp19. Some suitable vectors derived from lambda include lambda-gt11, lambda-gt7 and lambda Charon 4.

Some vectors derived from plasmids especially suitable for replication in bacteria include pBR322 [Bolivar et al., *Gene* 2 (1977) 95–113]; pUC18 and pUC19 [Narrander et al., *Gene*, 26 (1983) 101–104]; and Ti plasmids [Bevan et al. *Nature* 304 (1983) 184–187]. The preferred vectors for amplifying the genes in bacteria are pBR322, pUC18 and pUC19.

Construction of Vectors for Replication

In order to construct a chimeric gene suitable for replication in bacteria, a promoter sequence, a 5' untranslated sequence, a coding sequence and a 3' untranslated sequence are inserted into or are assembled in the proper order in a suitable vector, such as a vector described above. In order to be suitable, the vector must be able to replicate in the host cell.

The promoter, 5' untranslated region, coding region and 3' untranslated region, which comprise the chimeric gene of the invention, may first be combined in one unit outside the vector, and then inserted into the vector. Alternatively, portions of the chimeric gene may be inserted into the vector separately. The vector preferably also contains a gene that confers a trait on the host cell permitting the selection of cells containing the vector. A preferred trait is antibiotic resistance. Some examples of useful antibiotics include ampicillin, tetracycline, hygromycin, G418 and neomycin.

Insertion or assembly of the gene in the vector is accomplished by standard methods such as the use of recombinant DNA [Maniatis, et al., (1982)] and homologous recombination [Hinnen et al., *Proc. Natl. Acad. Sci.* 75 (1978) 1929–1933].

Using known recombinant DNA methods, the vector is cut, the desired DNA sequence is inserted between the cut pieces of the vector, and the ends of the desired DNA sequence are ligated to the corresponding ends of the vector.

The vector is most conveniently cut by means of suitable restriction endonucleases. Some suitable restriction endonucleases include those which form blunt ends, such as SmaI, HpaI and EcoRV, and those which form cohesive ends, such as EcoRI, SacI and BamHI.

The desired DNA sequence normally exists as part of a larger DNA molecule such as a chromosome, plasmid, transposon or phage. The desired DNA sequence is excised from its source, and optionally modified so that the ends can be joined to the ends of the cut vector. If the ends of the desired DNA sequence and of the cut vector are blunt ends, they are joined by blunt end ligases such as T4 DNA ligase.

The ends of the desired DNA sequence may also be joined to the ends of the cut vector in the form of cohesive ends, in which case a cohesive end ligase, which may also be T4 DNA ligase is used. Other suitable cohesive end ligases include, for example, *E. coli* DNA ligase.

Cohesive ends are most conveniently formed by cutting the desired DNA sequence and the vector with the same restriction endonuclease. In such a case, the desired DNA sequence and the cut vector have cohesive ends that are complementary to each other.

The cohesive ends may also be constructed by adding complementary homopolymer tails to the ends of the desired DNA sequence and to the cut vector using terminal deoxynucleotidyl transferase, or by adding a synthetic oligonucleotide sequence recognized by a particular restriction endonuclease, known as a linker, and cleaving the sequence with the endonuclease; see, for example, Maniatis et al., (1982).

Construction of Vectors for Transformation of Plants

In addition to the chimeric gene coding for a Bt toxin or a Bt-like toxin, the vectors preferably further comprise a DNA sequence that permits the selection or screening of corn plant cells containing the vector in the presence of cells that do not contain the vector. Such selectable or screenable markers may naturally be present in the vector into which the chimeric gene of this invention is introduced, or may be introduced into the vector either before or after the chimeric gene is introduced. Alternatively, the selectable or screenable marker gene or a portion thereof may first be joined to the desired chimeric gene or any portion thereof and the recombined genes or gene segments may be introduced as a unit into the vector. The selectable or screenable marker may itself be chimeric.

A preferred selectable marker is a gene coding for antibiotic resistance. The gene must be capable of expression in the cells to be transformed. The cells can be cultured in a medium containing the antibiotic, and those cells containing the vector, which have an enhanced ability to survive in the medium, are selected. Genes that confer resistance to corn toxins such as hygromycin or G418 may be useful as a selectable marker.

Some examples of genes that confer antibiotic resistance include, for example, neomycin phosphotransferase [kanamycin and G418 resistance, Velten et al. *EMBO J.* 3 (1984) 2723–2730]; hygromycin phosphotransferase [hygromycin resistance, van den Elzen et al., *Plant Molec. Biol.*, 5 (1985) 299–302].

Preferred vectors for transforming corn plants comprise a CaMV 35S promoter functionally joined to a Bt toxin coding region and a CaMV 35S promoter functionally joined to a selectable marker gene such as G418 resistance and hygromycin resistance. Examples of such vectors are pCIB710/ 35S (G418 resistance) and pIRV (hygromycin resistance) as described below.

The present invention also includes fertile corn plants, the cells of which contain the chimeric gene that expresses a BT crystal toxin or a polypeptide having substantially the insect toxicity properties of Bt crystal toxin.

Insecticides

The plant cells of this invention contain the chimeric gene and may be used to produce the polypeptide having substantially the insect toxicity properties of a Bt crystal protein. The plant cells per se may constitute the insecticide. Plant cells used directly as insecticides may be cultured plant cells, or may be components of a living plant.

The toxin may also be isolated from the plant cells by known methods, for example, by extraction or chromatography. The extract may be the total plant cell extract, a partially purified extract, or a pure preparation of the polypeptide. Any such extract or chromatographic isolate may be used in the same way as crystal protein from Bt; see, for example, Deacon, *Aspects of Microbiology*, 7 (1983) Cole et al., ed, American Society for Microbiology and Miller et al., *Science* 219 (1983) 715.

The insecticidal cells of the present invention are toxic to lepidopteran insects that attack corn cells and plants, such as the corn earworm (*Heliothis zea*) and the European corn borer (*Ostrinia nubilalis*). Furthermore, cells of corn bearing the crystal toxin gene of Bt var. tenebrionis are toxic to coleopteran insect pests. Important insect pests belonging to the order Coleoptera are, for example, the Colorado potato beetle, boll weevil, and corn root worm.

Hence, the present invention provides a method for producing in *Zea mays* a polypeptide having substantially the insect toxicity properties of a *Bacillus thuringensis* crystal protein, which method comprises:

(a) introducing into *Zea mays* cells a gene coding for a polypeptide having substantially the insect toxicity properties of a Bt crystal protein wherein the promoter, 5' untranslated region, and optionally, the 3' untranslated region of the gene are derived from plant or plant virus gene, and (b) expressing the polypeptide.

The present invention also provides a method of controlling insect larvae comprising feeding the larvae an insecticidal amount of transgenic *Zea mays* cells containing a gene coding for a *Bacillus thuringiensis* crystal toxin or a polypeptide having substantially the insect toxicity properties of a *Bacillus thuringiensis* crystal protein.

The present invention also includes a method for killing or controlling Lepidopteran larvae comprising feeding the larvae an insecticidal amount of transgenic corn plant cells that contain the chimeric gene of the invention. The plant cells may be cultured plant cells, or may be components of living plants. Furthermore, the present invention also includes a method for killing Coleopteran larvae by feeding them an insecticidal amount of cells containing the chimeric gene having the coding sequence of the Bt var. tenebrionis crystal toxin or insecticidal parts thereof.

The present invention further includes corn seeds of plants genetically engineered in accordance with this invention as long as the seeds contain the inserted chimeric gene and the desirable trait resulting therefrom. Progeny of plants produced by the method of this invention, including sexual and vegetative progeny, are further embodiments. Sexual progeny may result from selfing or cross pollination.

UTILITY

The method of the present invention permits protoplasts of *Zea mays* to be regenerated into fertile plants. This possibility enables one to introduce exogenous DNA (for example, a gene coding for a Bt crystal protein) stably into the genome of such plants, and to alter their phenotype. In addition, the protoplasts can be fused with protoplasts from the same or another species, in order to produce novel combinations of nuclear DNA, or novel combinations of nuclear and organelle DNA. This latter possiblity permits one, for example, to construct new male sterile plants for breeding purposes. Moreover, the protoplasts can be used as a source of clonal material, on which mutagenesis and/or selection for a desired phenotype can be carried out. Examples of desired phenotypes are for example, increased resistance to phytotoxic chemicals, to pathogens, to pests, to adverse environmental conditions, modified morphological or developmental properties, and altered contents of metabolic substances.

EXAMPLES

Example 1a

Preparation of a special type of callus of *Zea mays*, genotype Funk 2717.

*Zea mays* plants of genotype Funk 2717 are grown to flowering in the greenhouse, and pollinated with pollen from the same genotype. Immature cobs containing embryos 1.5 to 2.5 mm in length are removed from the plants and sterilized in 10% Clorox® solution for 20 minutes. Embryos are removed from the kernels and placed with the embryo axis downwards on Murashige and Skoog medium [*Physiol. Plant*, 15 (1962) 473–497] containing 0.1 mg/liter 2,4-D, 6% w/v sucrose and 25 mM L-proline solidified with 0.24% w/v Gelrite® (initiation medium). After two weeks' culture in the dark at 27° C., the callus developing on the scutellum is removed from the embryo and placed on B5 medium (0.5 mg/liter 2,4-D) solidified with Gelrite®. The material is subcultured every 2 weeks to fresh medium. After about 8 weeks from placing the embryos on the initiation medium, the special type of callus is identified by its characteristic morphology. This callus is subcultured further on the same medium. After a further period of 2 months, the callus is transferred to, and serially subcultured on, N6 medium containing 2 mg/liter 2,4-D and solidified with Gelrite®.

Example 1b

Preparation of a special type of callus of *Zea mays*, genotype Funk 5N984.

*Zea mays* plants of genotype Funk 5N984 are grown to flowering in the greenhouse, and pollinated with pollen from the same genotype. Immature cobs containing embryos 1.5 to 2.5 mm in length are removed from the plants and sterilized in 15% Clorox® solution for 15 minutes. Embryos are removed from the kernels and placed with the embryo axis downwards on the medium of Schenk and Hildebrandt [*Can. J. Bot.*, 50 (1972) 199–204] containing 1.0 mg/liter 2,4-D, 2% w/v sucrose, 100 mg/liter casein hydrolysate, 100 mg/liter myo-inositol and 25 mM L-proline solidified with 0.8% w/v Phytagar® (initiation medium). After two weeks' culture in the dark at 27° C., a preferred callus is recognized by the presence of well formed globular, somatic embryos developing on the scutellum of certain explants. These calli are removed and placed either on B5 medium (0.5 mg/liter 2,4-D plus 2% w/v sucrose, 100 mg/liter casein hydrolysate, 100 mg/liter myo-inositol and 25 mM L-proline) or Schenk and Hildebrandt medium (as described above). The material is subcultured every 2 weeks to fresh medium. After a minimum of 8 weeks from placing the embryos on the initiation medium, the special type of callus is identified by its characteristic morphology. The special type of callus may be subcultured further on the same medium but, preferably, is transferred to, and serially subcultured on, N6 medium containing 2 mg/liter 2,4-D and solidified with 0.24% w/v Gelrite®. Embryogenic suspension cultures can be established from these callus cultures by the method outlined in examples 2a and 2b.

Example 2a

Preparation of a suspension of *Zea mays* genotype Funk 2717 or Funk 5N984.

The callus described in examples 1a or 1b remains in culture for a total of at least 6 months. The type of callus chosen for subculture is relatively non-mucilaginous, and is granular and very friable such that it separates into individual cell aggregates on placing into liquid medium. Cultures containing aggregates with large, expanded cells are not retained.

Approximately 500 mg aliquots of the special callus of *Zea mays* described in step (a) above, of the elite genotype Funk 2717, are placed into 30 ml of N6 medium containing 2 mg/liter 2,4-D in 125 ml delong flasks. After 1 week of culture at 26° C. in the dark on a gyratory shaker, (130 rpm, 2.5 cm throw) the medium is replaced with fresh medium. The suspensions are subcultured in this way again after another week.

At this time, the cultures are inspected, and those which do not show large numbers of expanded cells are retained. Suspension cultures containing aggregates with large, expanded cells are discarded. The preferred tissue consists of densely cytoplasmic dividing cell aggregates which have a characteristically smoother surface than most of the cell aggregates. The cultures retained have at least 50% of the cells represented in these small aggregates. This is the desired morphology. These suspensions also have a rapid growth rate, with a doubling time of less than 1 week. The suspension cultures are subcultured weekly by transferring 0.5 ml packed cell volume (PCV: settled cell volume in a pipette) into 25 ml of fresh medium. After 4 to 6 weeks of subculture in this fashion, the cultures increase 2 to 3 fold per weekly subculture. Cultures in which >75% of the cells are of the desired morphology are retained for further subculture. The cultures are maintained by always choosing for subculture the flask whose contents exhibit the best morphology. Periodic filtration through 630 micrometer pore size stainless steel sieves (every 2 weeks) are used in some cases to increase the dispersion of the cultures, but is not necessary.

*Zea mays* suspension culture 6-2717-CG (Funk 2717) (a hybrid Funk 2717) is on deposit with ATCC, accession number 40326. This deposition was made in accordance with the Budapest Treaty [date of deposit: May 20, 1987].

Example 2b

Preparation of a suspension of *Zea mays* genotype Funk 5N984.

The callus described in example 1b remains in culture for a total of at least 6 months. The type of callus chosen for subculture is relatively non-mucilaginous, and is granular and very friable, such that it separates into individual cell aggregates on placing it into liquid medium. Cultures containing aggregates with large, expanded cells are not retained.

Approximately 500 mg aliquots of the special callus of *Zea mays* of the elite genotype Funk 5N984 are placed into 30 ml of KMX medium containing 2 mg/liter 2,4-D in 125 ml delong flasks. The suspensions are then subcultured and selected as described for suspensions of elite genotype Funk 2717 in example 2a above.

Example 3

Preparation of protoplasts from suspension cultures of *Zea mays*.

1 to 1.5 ml PCV of the suspension culture cells prepared as in example 2 are incubated in 10 to 15 ml of a mixture consisting of 4% w/v RS cellulase with 1% w/v Rhozyme in KMC (8.65 g/liter KCl, 16.47 g/liter $MgCl_2.6H_2O$ and 12.5 g/liter $CaCl_2.2H_2O$, 5 g/liter MES pH 5.6.) salt solution. Digestion is carried out at 30° C. on a rocking table, for a period of 3 to 4 hours. The preparation is monitored under an inverted microscope for protoplast release.

The protoplasts which are released are collected as follows: The preparation is filtered through a 100 μm mesh sieve, followed by a 50 μm mesh sieve. The protoplasts are washed through the sieves with a volume of KMC salt solution equal to the original volume of enzyme solution. 10 ml of the protoplast preparation is placed in each of several plastic disposable centrifuge tubes, and 1.5 to 2 ml of 0.6M sucrose solution (buffered to pH 5.6 with 0.1% w/v morpholino-ethane sulfonic acid [MES] and KOH) layered underneath. The tube is centrifuged at 60 to 100 g for 10 minutes, and the protoplasts banding at the interface collected and placed in a fresh tube.

The protoplast preparation is resuspended in 10 ml of fresh KMC salt solution, and centrifuged for 5 minutes at 60 to 100 g. The supernatant is removed and discarded,, and the protoplasts resuspended gently in the drop remaining, and then 10 ml of a 13/14 strength KMC solution added gradually. After centrifuging again for 5 minutes., the supernatant is again removed and the protoplasts resuspended in a 6/7 strength KMC solution. An aliquot is taken for counting, and the protoplasts sedimented again by centrifugation. The protoplasts are resuspended at $10^7$ per ml in KM medium (table 1), or in mannitol solution having the same osmolality as the KM medium and containing 6 mM $MgCl_2$, or any other suitable medium for use in transformation as described in the following examples. This protoplast suspension is used for culture as described in Example 8a, or where performed, for transformation of the protoplasts as described in Examples 8 and 9.

Example 4

General Recombinant DNA Techniques

Since many of the recombinant DNA techniques used in this invention are routine for those skilled in the art, a brief description of these commonly used techniques is included here rather than at each instance where they appear below. Except where noted, all of these routine procedures are described in the reference by Maniatis et al., (1982).

A. Restriction endonuclease digestions.

Typically, DNA is present in the reaction mixture at approximately 50–500 ug/ml in the buffer solution recommended by the manufacturer, New England Biolabs, Beverly, Mass., 2–5 units of restriction endonucleases are added for each ug of DNA, and the reaction mixture incubated at the temperature recommended by the manufacturer for one to three hours. The reaction is terminated by heating to 65°

C. for ten minutes or by extraction with phenol, followed by precipitation of the DNA with ethanol. This technique is also described on pages 104–106 of the Maniatis et al reference.

B. Treatment of DNA with polymerase to create flush ends.

DNA fragments are added to a reaction mixture at 50–500 ug/ml in the buffer recommended by the manufacturer, New England Biolabs. The reaction mixture contains all four deoxynucleotide triphosphates at a concentration of 0.2 mM. The reaction is incubated at 15° C. for 30 minutes, and then terminated by heating to 65° C. for ten minutes. For fragments produced by digestion with restriction endonucleases that create 5'-protruding ends, such as EcoRI and BamHI, the large fragment, or Klenow fragment, of DNA polymerase is used. For fragments produced by endonucleases that produce 3'-protruding ends, such as PstI and SacI, T4 DNA polymerase is used. Use of these two enzymes is described on pages 113–121 of the Maniatis et al reference.

C. Agarose gel electrophoresis and purification of DNA fragments from gels.

Agarose gel electrophoresis is performed in a horizontal apparatus as described on pages 150–163 of Maniatis et al reference. The buffer used is the Tris-borate buffer described therein. DNA fragments are visualized by staining with 0.5 ug/ml ethidium bromide, which is either present in the gel and tank buffer during electrophoresis or added following electrophoresis. DNA is visualized by illumination with short-wavelength or long-wavelength ultraviolet light. When the fragments are to be isolated from the gel, the agarose used is the low gelling-temperature variety, obtained from Sigma Chemical, St. Louis, Mo. After electrophoresis, the desired fragment is excised, placed in a plastic tube, heated to 65° C. for approximately 15 minutes, then extracted with phenol three times and precipitated with ethanol twice. This procedure is slightly modified from that described in the Maniatis et al reference at page 170.

D. Addition of synthetic linker fragments to DNA ends.

When it is desired to add a new restriction endonuclease site to the end of a DNA molecule, that molecule is first treated with DNA polymerase to create flush ends, if necessary, as described in the section above. Approximately 0.1 to 1.0 μg of this fragment is added to approximately 100 ng of phosphorylated linker DNA, obtained from New England Biolabs, in a volume of 20 to 30 μl containing 2 μl of T4 DNA ligase, from New England Biolabs, and 1 mM ATP in the buffer recommended by the manufacturer. After incubation overnight at 15° C., the reaction is terminated by heating the mixture at 65° C. for ten minutes. The reaction mixture is then diluted to approximately 100 μl in a buffer suitable for the restriction endonuclease that cleaves at the synthetic linker sequence, and approximately 50 to 200 units of this endonuclease are added. The mixture is incubated at the appropriate temperature for 2 to 6 hours, then the fragment is subjected to agarose gel electrophoresis and the fragment purified as described above. The resulting fragment will now have ends with termini produced by digestion with the restriction endonuclease. These termini are usually cohesive, so that the resulting fragment is now easily ligated to other fragments having the same cohesive termini.

E. Removal of 5'-terminal phosphates from DNA fragments.

During plasmid cloning steps, treatment of the vector plasmid with phosphatase reduces recircularization of the vector (discussed on page 13 of Maniatis et al reference). After digestion of the DNA with the appropriate restriction endonuclease, one unit of calf intestine alkaline phosphatase, obtained from Boehringer-Mannheim, Indianapolis, Ind., is added. The DNA is incubated at 37° C. for one hour, then extracted twice with phenol and precipitated with ethanol.

F. Ligation of DNA fragments.

When fragments having complementary cohesive termini are to be joined, approximately 100 ng of each fragment are incubated in a reaction mixture of 20 to 40 μl containing approximately 0.2 units of T4 DNA ligase from New England Biolabs in the buffer recommended by the manufacturer. The incubation is conducted for 1 to 20 hours at 15° C. When DNA fragments having flush ends are to be joined, they are incubated as above, except the amount of T4 DNA ligase is increased to 2 to 4 units.

G. Transformation of DNA into E. coli.

E. coli strain HB101 is used for most experiments. DNA is introduced into E. coli using the calcium chloride procedure described by Maniatis et al on pages 250–251.

H. Screening E. coli for plasmids.

Following transformation, the resulting colonies of E. coli are screened for the presence of the desired plasmid by a quick plasmid isolation procedure. Two convenient procedures are described on pages 366–369 of Maniatis et al., (1982) reference.

I. Large scale isolation of plasmid DNA.

Procedures for isolating large amounts of plasmids in E. coli are found on pages 88–94 of the Maniatis et al (1982) reference.

J. Cloning into M13 phage vectors.

In the following description, it is understood that the double-stranded replicative form of the phage M13 derivatives is used for routine procedures such as restriction endonuclease digestions, ligations, etc.

Example 5

Construction of Chimeric gene in plasmid pBR322.

In order to fuse the CaMV gene VI promoter and protoxin coding sequences, a derivative of phage vector mp19 [Yanisch-Perron et al., (1985)] is constructed. First, a DNA fragment containing approximately 155 nucleotides 5' to the protoxin coding region and the adjacent approximately 1346 nucleotides of coding sequence are inserted into mp19. Phage mp19 ds rf (double-stranded replicative form) DNA is digested with restriction endonucleases SacI and SmaI and the approximately 7.2-kbp vector fragment is purified after electrophoresis through low-gelling temperature agarose by standard procedures. Plasmid pKU25/4, containing approximately 10 kbp (kilobase pairs) of *Bacillus thuringiensis* DNA, including the protoxin gene, is obtained from Dr. J. Nuesch, CIBA-GEIGY Ltd., Basle, Switzerland. The nucleotide sequence of the protoxin gene present in plasmid pKU25/4 is shown in sequence (I). Plasmid pKU25/4 DNA is digested with endonucleases HpaI and SacI, and a 1503 bp fragment (containing nucleotides 2 to 1505 in sequence (I)) is purified as above. (This fragment contains approximately 155 bp of bacterial promoter sequences and approximately 1346 bp of the start of the protoxin coding sequence.) Approximately 100 ng of each fragment is then mixed, T4 DNA ligase added, and incubated at 15° C. overnight. The resulting mixture is transformed into *E. coli* strain HB101, mixed with indicator bacteria *E. coli* JM 101 and plated as described [Messing, J., *Meth. Enzymol.* 101 (1983) 20]. One phage called mp19/bt is used for further construction below.

Next, a fragment of DNA containing the CaMV gene VI promoter, and some of the coding sequences for gene VI, is inserted into mp19/bt. Phage mp19/bt ds rf DNA is digested with BamHI, treated with the large fragment of DNA polymerase to create flush ends and recleaved with endonuclease PstI. The larger vector fragment is purified by electrophoresis as described above. Plasmid pABD1 is described in Paszkowski et al., *Embo J.* 3 (1984) 2717–2722. Plasmid pABD1 DNA is digested with PstI and HindIII. The fragment approximately 465 bp long containing the CaMV gene VI promoter and approximately 75 bp of gene VI coding sequence is purified. The two fragments are ligated and plated as described above. One of the resulting recombinant phages, called mp19/btca is used in the following experiment:

Phage mp19/btca contains CaMV gene VI promoter sequences, a portion of the gene VI coding sequence, approximately 155 bp of *Bacillus thuringiensis* DNA upstream of the protoxin coding sequence, and approximately 1346 bp of the protoxin coding sequence. To fuse the CaMV promoter sequences precisely to the protoxin coding sequences, the intervening DNA is deleted using oligonucleotide-directed mutagenesis of mp19/btca DNA. A DNA oligonucleotide with the sequence (5') TTCGGATTGTTATCCATGGTTGGAGGTCTGA (3') is synthesized by routine procedures using an Applied Biosystems DNA Synthesizer. This oligonucleotide is complementary to those sequences in phage mp19/btca DNA at the 3' end of the CaMV promoter [nucleotides 5762 to 5778 in Hohn, (1982)] and the beginning of the protoxin coding sequence (nucleotides 156 to 172) in formula I above. The general procedure for the mutagenesis is that described in Zoller and Smith (1983). Approximately 5 µg of single-stranded phage mp19/btca DNA is mixed with 0.3 µg of phosphorylated oligonucleotide in a volume of 40 µl. The mixture is heated to 65° C. for 5 minutes, cooled to 50° C., and slowly cooled to 4° C. Next, buffer, nucleotide triphosphates, ATP, $T_4$ DNA ligase and large fragment of DNA polymerase are added and incubated overnight at 15° C. as described [see Zoller and Smith (1983)]. After agarose gel electrophoresis, circular double-stranded DNA is purified and transfected into *E. coli* strain JM101. The resulting plaques are screened for sequences that hybridize with 32P-labelled oligonucleotide, and phage are analyzed by DNA restriction endonuclease analysis. Among the resulting phage clones will be ones which have correctly deleted the unwanted sequences between the CaMV gene VI promoter and the protoxin coding sequence. This phage is called mp19/btca/del.

Next, a plasmid is constructed in which the 3' coding region of the protoxin gene is fused to CaMV transcription termination signals. First, plasmid pABD1 DNA is digested with endonucleases BamHI and BglII and a 0.5 kbp fragment containing the CaMV transcription terminator sequences is isolated. Next, plasmid pUC19, Yanisch-Perron et al., *Gene* 33 (1985) 103–119 is digested with BamHI, mixed with the 0.5 kbp fragment and incubated with $T_4$ DNA ligase. After transformation of the DNA into *E. coli* strain HB101, one of the resulting clones, called plasmid p702, is obtained.

Next, plasmid p702 DNA is cleaved with endonucleases SacI and SmaI, and the larger, approximately 3.2 kbp fragment is isolated by gel electrophoresis. Plasmid PKU25/4 DNA is digested with endonucleases AhaIII and SacI, and the 2.3-kbp fragment (nucleotides 1502 to 3773 in formula I above) containing the 3' portion of the protoxin coding sequence (nt 1504 to 3773 of the sequence shown in formula I is isolated after gel electrophoresis. These two DNA fragments are mixed, incubated with $T_4$ DNA ligase and transformed into *E. coli* strain HB101. The resulting plasmid is p702/bt.

Finally, portions of phage mp19/btca/del ds rf DNA and plasmid p702/bt are joined to create a plasmid containing the protoxin coding sequence flanked by CaMV promoter and terminator sequences. Phage mp19/btca/del DNA is digested with endonucleases SacI and SphI, and a fragment of approximately 1.75 kbp is purified following agarose gel electrophoresis. Similarly, plasmid p702/bt DNA is digested with endonucleases SacI and SalI and a fragment of approximately 2.5 kbp is isolated. Finally, plasmid pBR322 DNA [Bolivar et al., (1977) is digested with SalI and SphI and the larger 4.2 kbp fragment isolated. All three DNA fragments are mixed and incubated with $T_4$ DNA ligase and transformed into *E. coli* strain HB101. The resulting plasmid, pBR322/bt14 is a derivative of pBR322 containing the CaMV gene VI promoter and translation start signals fused to the Bt crystal protein coding sequence, followed by CaMV transcription termination.

Example 6a

Construction of pTOX, containing a chimeric gene encoding the insecticidal toxin gene of *Bacillus thuringiensis* var *tenebrionis*

A gene encoding the insecticidal crystal protein gene of *Bacillus thuringiensis* var. *tenebrionis* has been characterized and sequenced [Sekar, V. et al., *Proc. Natl. Acad Sci USA*, 84 (1987) 7036–7040]. This coding sequence is isolated on a convenient restriction fragment, such as a HindIII fragment of approximately 3 kb in size, and inserted into an appropriate plant expression vector, such as the plasmid pCIB 770 [Rothstein, S. et al., *Gene*, 53 (1987) 153–161]. The plasmid pCIB 770 contains a chimeric kanamycin gene for expression in plants, as well as the promoter and terminator of the 35S RNA transcript of CaMV [cauliflower mosaic virus] separated by a unique BamH1 site. The restriction fragment bearing the toxin coding sequence is made compatible to the unique BamHI site of pCIB 770 by use of the appropriate molecular adapter and ligated together.

Example 6b

Construction of pSAN, containing a chimeric gene encoding the insecticidal toxin gene of *Bacillus thuringiensis* strain san diego A gene encoding the insecticidal protein of *Bacillus thuringiensis* strain *san diego* has been characterized and sequenced by Herrnstadt et al., EP-0-202-739 and EP-0-213-818. This coding sequence is isolated on a convenient restriction fragment and inserted into the appropriate plant expression vector, such as pCIB 770. The plasmid pCIB770 contains a chimeric kanamycin gene for expression in plants, as well as the promoter and terminator of the 35S RNA transcript of CaMV [cauliflower mosaic virus] separated by a unique BamH site. The restriction fragment bearing the toxin coding sequence is made compatible to the unique BamHI site of pCIB 770 by use of the appropriate molecular adapter and ligated together.

Example 7a

Construction of Plasmid pCIB 710.

The plasmid pLW111 (available from S. Howell, University of California, San Diego) consists of the three smaller EcoRI fragments of the BJI strain of cauliflower mosaic virus (CaMV) [Franck et al (1980) *Cell* 21: 285–294] cloned into pMB9. pLW111 is digested with BglII and a 1150 bp fragment [base pairs numbers 6494–7643, Hohn et al., *Current Topics in Microbiology and Immunology* 96 (1982) 193–236] isolated. This fragment is ligated into the BamHI site of pUC 19. This restriction fragment codes for both the promoter for the CaMV 35S RNA and the polyA addition signal (i.e. the terminator) for that transcript.

In vitro mutagenesis

A unique BamHI site is inserted between this promoter and terminator via in vitro mutagensis. A 36-base oligonucleotide is synthesized which is identical to the CaMV sequence in that region except that a BamHI restriction site is inserted at base pair No 7483 in the sequence.

The 1150 bp BglII fragment from above is cloned into M13mp19 and single-stranded phage DNA isolated.

This single-stranded DNA is annealed with the synthetic oligonucleotide, a new strand is synthesized using the oligonucleotide as a primer and the DNA transfected into strain JM101 [Zoller and Smith, *DNA*, 3 (1984) 479–488].

M13 phage having the BamHI site inserted are isolated as described in Zoller and Smith (supra).

Selection of desired mutant phage

The 36 base oligonucleotide is labeled by kinasing with 32-P-ATP.

A set of the transfected M13 phage plaques is localized on a nitrocellulose filter. This filter is hybridized with the labeled 36-mer. The filter is washed at increasing temperatures. Mutated phages are stable at higher wash temperature.

One of these phages stable at higher temperature is isolated and sequenced to confirm the presence of the BamHI site.

Final assembly of pCIB 710

Double-stranded DNA isolated from this phage is digested with HindIII and Eco RI. pUC19 is cleaved with HindIII and EcoRI. These two digested DNA's are ligated. Transformants are selected by ampicillin resistance. One transformant from this ligation is pCIB710.

The plasmid pCIB710 has no ATG start codons between this BamHI site which was inserted and the starting point of transcription.

Example 7b

Construction of pCIB712

The hygromycin resistance gene [Gritz, L. and Davies, J. *Gene*, 25 (1983) 179–188] is present on a ca. 1150 basepair BamHI fragment from the plasmid pLG90. The plasmid pLG90 is available from Dr. Linda Gritz, Applied Biotechnology, 80 Rogers St., Cambridge, Mass. 02142. This fragment was linkered with BglII linkers and then inserted into the unique BamHI site of pCIB 710, destroying the BamHI site and constructing the plasmid pCIB 712. The plasmid pCIB 712 has been deposited with ATCC, Rockville, Md., U.S.A., accession number 67407. This deposition was made in accordance with the Budapest Treaty [date of deposit: May 18, 1987].

The plasmid pCIB712 is linearized using an appropriate enzyme, for example SmaI.

Example 7c

Construction of pCIB10/35SBt

The plasmid pCIB710 is described above.

Construction of pCIB10 see FIGS. 7b to 7h).

15. A T-DNA fragment containing the left border from pTiT37 is isolated from pBR325 (EcoRI29) [Yadav et al., *Proc Natl. Acad. Sci. USA* 79 (1982) 6322–6326]. pBR325 (EcoRI29) is cut with EcoRI and the 1.1 kb fragment linkered with Hind III linkers (New England Biolabs).

16. The plasmid pBR322 [Bolivar et al., *Gene* 2 (1977) 95–103] is cut with HindIII.

17. The left border-containing fragment described in step 15 is ligated into the HindIII digest of pBR322.

18. The left border-containing plasmid constructed in step 17 is digested with ClaI and HindIII and the 1.1 kb HindIII/ClaI fragment isolated [Hepburn et al., *J. Mol. Appl. Genet.* 2 (1983) 315–329.]

19. The plasmid pUC18 [Norrander et al., *Gene* 26 (1983) 101–106] is cut with HindIII and EcoRI; the 60 bp polylinker is end-labeled using T4 polynucleotide Kinase and gamma-$^{32}$p-dATP and isolated from an acrylamide gel.

20. The plasmid pBR322 is cut with EcoRI and ClaI and the large fragment isolated.

21. The 60 bp HindIII/EcoRI polylinker and the 1.1 kb HindIII/ClaI fragment of EcoRI29 is ligated into pBR322 cut with ClaI and EcoRI, constructing pCIB5.

22. A chimeric gene conferring kanamycin resistance (nos-neo) is taken from Bin 6 [Beyan, *Nuc. Acid Res.* 12 (1984) 8711–8721] as a SalI/EcoRI fragment.

23. The plasmid pUC18 is cut with EcoRI and SalI.

24. The SalI/EcoRI fragment containing the chimeric gene of step 22 is ligated into the pUC18 cut with EcoRI and SalI.

25. The BamHI recognition site in the termination sequence of this chimeric gene is destroyed by cutting with BamHI, filling in using T4 DNA polymerase, and ligating.

26. The resulting plasmid is cut with SstII (Bethesda Research Laboratories) and HindIII.

27. A fragment containing the 5' part of the nos promoter and the right border of pTiT37 is isolated by cutting pBR325 (Hind23) with HindIII and SstII and isolating the 1.0 kb fragment.

28. This 1.0 kb HindIII/SstII fragment is ligated into pUC18 vector of step 26 constructing pCIB4.

29. pCIB5 containing a left T-DNA border is cut with AatII, rendered blunt-ended by treatment using T4 DNA polymerase, and then cut with EcoRI.

30. pCIB4 is cut with HindIII, rendered blunt by treatment using Klenow fragment of *E. coli* DNA polymerase I, and cut with EcoRI.

31. The vector of step 29 is ligated with the large fragment of step 30 constructing pCIB2, a ColE1 replicon containing left and right T-DNA borders flanking a chimeric Km$^r$ gene and a polylinker.

32. The plasmid pRZ102 [Jorgensen, et al., *Mol. Gen. Genet.* 177 (1979) 65–72] is digested with BamHI and filled in using Klenow.

33. An AluI partial digest of plasmid pAO3 [Oka, et al., *Nature* 276 (1978) 845–847 and Oka et al., *J. Mol. Biol.* 147 (1981) 217–226] is made.

34. The AluI digest is ligated into the restricted pRZ102, from step 32, selecting the desired transformants by resistance to kanamycin.

35. The resulting plasmid has the coding sequence of Tn903 present on a 1.05 kb BamHI fragment; this fragment is isolated after BamHI digestion and filling-in with Klenow.

36. The plasmid pRK252, a derivative of the broad host range plasmid pRK2, is available from Dr. Don Helinski of the University of California, San Diego. This plasmid lacks the BglII site present in the parent plasmid pRK290 [Ditta et al., *Proc. Nat. Acad. Sci. USA*, 77 (1980) 262–269]. pRK252, is digested with SmaI and SalI, filled in using Klenow, and the large fragment resulting from this digest isolated.

37. The TN903 containing fragment, isolated in step 35, is ligated into the large fragment from pRK252, constructing pRK252 Km.

38. The plasmid pRK252 Km is cut with EcoRI, blunt-ended using Klenow, and linkered with BglII linkers (New England Biolabs).

39. The plasmid pCIB2 is cut with EcoRV and is linkered with BglII linkers (New England Biolabs).

40. The BglII-linkered pCIB2 of step 39 is ligated into vector of step 38 constructing pCIB10.

Example 7d

Construction of pCIB10a

Example 7c can be repeated substituting the plasmid pRK290 for pRK252.

41. The plasmid pRZ102 [Jorgensen, et al., (1979), supra] is digested with BamHI and filled in using Klenow.

42. An AluI partial digest of plasmid pA03 [Oka, et al., (1978), supra] is made.

43. The AluI digest is ligated into the restricted pRZ102, from step 32, selecting the desired transformants by resistance to kanamycin.

44. The resulting plasmid has the coding sequence of Tn903 present on a 1.05 kb BamHI fragment; this fragment is isolated after BamHI digestion and filling-in with Klenow.

45. The plasmid pRK290, a derivative of the broad host range plasmid RK2, is available from Dr. Don Helinski of the University of California, San Diego. pRK290 is digested with SmaI and SalI, filled in using Klenow, and the large fragment resulting from this digest isolated.

46. The Tn903 containing fragment, isolated in step 35, is ligated into the large fragment from pRK290, constructing pRK290 Km.

47. The plasmid of step 46 is digested with BglII, filled in using Klenow and ligated, destroying its BglII site, to construct pRK290 Km.

48. The plasmid pRK290 Km is cut with EcoRI, blunt-ended using Klenow, and linkered with BglII linkers (New England. Biolabs).

49. The plasmid pCIB2 is cut with EcoRV and is linkered with BglII linkers (New England Biolabs).

50. The BglII-linkered pCIB2 of step 39 is ligated into vector of step 47 constructing pCIB10a.

Example 7e

Construction of a *Bacillus thuringiensis* protoxin chimeric gene with the CaMV 35S promoter
A. Construction of a CaMV 35S Promoter Cassette.

Plasmid pCIB 710 is constructed as shown in FIG. 10. This plasmid contains CaMV promoter and transcription termination sequences for the 35S RNA transcript [Covey, S. N., Lomonossoff, G. P. and Hull, R., *Nucleic Acids Research* 9 (1981) 6735–6747]. A 1149 bp BglII restriction fragment of CaMV DNA [bp 7643–6494 in Hohn et al., (1982) is isolated from plasmid pLV111 (obtained from Dr. S. Howell, University of California-San Diego; alternatively, the fragment can be isolated directly from CaMV DNA) by preparative agarose gel electrophoresis as described earlier and mixed with BamHI-cleaved plasmid pUC19 DNA, treated with $T_4$ DNA ligase, and transformed into *E. coli.* (Note the BamHI restriction site in the resulting plasmid has been destroyed by ligation of the BglII cohesive ends to the BamHI cohesive ends.) The resulting plasmid, called pUC19/35S, is then used in oligonucleotide-directed in-vitro mutagenesis to insert the BamHI recognition sequence GGATCC immediately following CaMV nucleotide 7483 in the Hohn reference. The resulting plasmid, pCIB710, contains the CaMV 35S promoter region and transcription termination region separated by a BamHI restriction site. DNA sequences inserted into this BamHI site will be expressed in plants by these CaMV transcription regulation sequences. (Also note that pCIB710 does not contain any ATG translation initiation codons between the start of transcription and the BamHI site.)

B. Insertion of the CaMV 35S Promoter/Terminator Cassette into pCIB10.

The following steps are outlined in FIG. 11. Plasmids pCIB10 and pCIB710 DNAs are digested with EcoRI and SalI, mixed and ligated. The resulting plasmid, pCIB10/710 has the CaMV35S promoter/terminator cassette inserted into the plant transformation vector pCIB10. The CaMV 35S sequences are between the T-DNA borders in pCIB10, and thus will be inserted into the plant genome in plant transformation experiments.

C. Insertion of the *Bacillus thuringiensis* protoxin gene into pCIB10/710.

The following steps are outlined in FIG. 12. As a source of the protoxin gene, plasmid pCIB10/19SBt is digested with BamHI and NcoI, and the 3.6 kb fragment containing the protoxin gene is isolated by preparative gel electrophoresis. The fragment is then mixed with synthetic NcoI-BamHI adapter with the sequence 5'-CATGGCCGGATCCGGC-3', then digested with BamHI. This step creates BamHI cohesive ends at both ends of the protoxin fragment. This fragment is then inserted into BamHI-cleaved pCIB10/710. The resulting plasmid, pCIB10/35SBt, shown in FIG. 12, contains the protoxin gene between the CaMV 35S promoter and transcription termination sequences.

Plasmid pCIB10/19SBt [in *E. coli* strain HB 101] is on deposit with ATCC and has the ATCC accession number 67330 [date of deposit: Feb. 27, 1987].

pCIB10/35SBt in strain MC1061 is on deposit with ATCC, Rockville, Md., USA, accession number 67329. This deposition was made in accordance with the requirements of the Budapest Treaty [date of deposit: Feb. 27, 1987].

Example 8

Transformation of *Zea mays* protoplasts by electroporation.

All steps except the heat shock are carried out at room temperature. The protoplasts are resuspended in the last step of example 3 in 0.5M mannitol containing 0.1% w/vMES and 6 mM $MgCl_2$. The resistance of this suspension is measured .in the chamber of a Dialog Electroporator® and adjusted to 1 to 1.2 kOhm using a 300 mM $MgCl_2$ solution. The protoplasts are heat shocked by immersing the tube containing the sample in a water bath at 45° C. for 5 minutes, followed by cooling to room temperature on ice. To aliquots of 0.25 ml of this suspension are added 4 μg of linearized pCIB712 plasmid containing the hygromycin resistance gene, and 20 μg of calf thymus carrier DNA.

To the protoplasts are added 0.125 ml of a 24% w/v polyethylene glycol (PEG) solution (MW of PEG 8000) in 0.5M mannitol containing 30 mM $MgCl_2$. The mixture is mixed well but gently, and incubated for 10 minutes. The sample is transferred to the chamber of the electroporator and pulsed 3 times at 10 second intervals at initial voltages of 1000, 1200, 1500, 1800, 2300 and 2800 V cm$^{-1}$ and an exponential decay time of the pulse of 10 microseconds (μsec).

The protoplasts are cultured as follows:

The samples are placed in 6 cm diameter petri dishes at room temperature. After a further 5 to 15 minutes, 3 ml of KM medium containing 1.2% w/v SeaPlaque® agarose, 1 mg/liter 2,4-D and 100 mg/liter 0-acetyl salicylic acid is added. The agarose and protoplasts are mixed well, and the medium allowed to gel.

Example 8b

Transformations of *Zea mays* protoplasts by electroporation.

Example 8a is repeated, with the modification that the resistance of the protoplast preparation is adjusted to 0.5 to 0.7 kOhm.

Example 8c

Transformation of *Zea mays* protoplasts by electroporation.

Example 8a is repeated, with the modification that the PEG used is PEG with a molecular weight of 4000.

Example 8d

Transformation of *Zea mays* protoplasts by electroporation.

Example 8c is repeated, with the modification that the resistance of the protoplast preparation is adjusted to 0.5 to 0.7 kOhm.

Example 8e

Transformation of *Zea mays* protoplasts by electroporation.

Example 8a is repeated with the modification that no PEG is added.

Example 8f

Transformation of *Zea mays* protoplasts by electroporation.

Example 8b is repeated with the modification that no PEG is added.

Example 8g

Transformation of *Zea mays* protoplasts by electroporation.

Example 8a is repeated with the modification that one half of volume of 12% w/v PEG is added.

Example 8h

Transformation of *Zea mays* protoplasts by electroporation.

Example 8b is repeated with the modification that one half volume of 12% w/v PEG is added.

Example 8i

Transformation of *Zea mays* protoplasts by electroporation.

Example 8c is repeated with the modification that one half volume of 12% w/v PEG is added.

Example 8j

Transformation *Zea mays* protoplasts by electroporation.

Example 8d is repeated with the modification that one half volume of 12% w/v PEG is added.

Example 8k

Transformation of *Zea mays* protoplasts by electropotation.

Examples 8a–8j are repeated with the modification that the pulses are applied at intervals of 3 seconds.

Example 8l

Transformation of *Zea mays* protoplasts by electroporation.

Examples 8a–8k are repeated wherein the protoplasts are placed after the electroporation in dishes placed on a plate cooled to a temperature of 16° C.

Example 8m

Transformation of *Zea mays* protoplasts by electroporation.

Examples 8a–8l are repeated with the modification that the protoplasts are placed in tubes after the electroporation step, and washed with 10 ml of 6/7 strength KMC solution, collected by centrifugation at 60 g for 10 minutes, resuspended in 0.3 ml of KM medium, and plated as in Example 8a.

Example 8n

Transformation of *Zea mays* protoplasts by electroporation.

Example 8m is repeated with the modification that the medium used for washing the protoplasts is W5 solution (380 mg/liter KCl; 18.375 g/liter CaCl$_2$.2H$_2$O; 9 g/liter NaCl; 9 g/liter glucose; pH 6.0).

Example 8o

Transformation of *Zea mays* protoplasts by electroporation.

Examples 8a–8n are repeated with the modification that the medium used to plate the protoplasts is KM medium containing 30% by volume of Schenk and Hildebrandt (1972) medium containing 30 μM Dicamba®, in which cell suspensions of *Dactylis glomerata* have previously been grown.

Example 8p

Transformation of *Zea mays* protoplasts by electroporation.

Examples 8a–8n are repeated with the modification that the medium used to plate the protoplasts is KM medium containing 15% by volume of Schenk and Hildebrandt medium [*Can. J. Bot.*, 50 (1972) 199–204] containing 30 μM Dicamba®, in which cell suspensions of *Dactylis glomerata* have previously been grown.

Example 8q

Transformation of *Zea mays* protoplasts by electroporation.

Examples 8a–8n are repeated with the modification that the medium used to plate the protoplasts is KM medium containing 30% by volume of N6 medium in which the cell suspensions described in example 3 have previously been grown.

Example 8r

Transformation of *Zea mays* protoplasts by electroporation.

Examples 8a–8n are repeated with the modification that the medium used to plate the protoplasts is KM medium containing 15% by volume of N6 medium in which the cell suspensions described in example 3 have previously been grown.

Example 8s

Transformation of *Zea mays* protoplasts by electroporation.

Examples 8a–8r are repeated with the modification that the protoplasts are taken up in culture medium (KM medium containing 0.5 mg/liter 2,4-D and 100 mg/liter O-acetyl-salicylic acid, and 1.2% w/v SeaPlaque® agarose) onto nurse culture filter, at a density of 0.5 million protoplasts/ml.

In this embodiment Durapore filters, [catalog number GVWP 04700, 0.22 μm pore size, 47 mm diameter] are numbered on the margin with a lead pencil on the upper surface as they are removed from the container. This is to insure that the upper side is facing up on the nurse cultures, and that only one filter is placed on each. The filters are autoclaved in distilled, deionized water in a translucent container (GA7® or any similar container), for 20 minutes. When they are cooled, the water is replaced with liquid KM media as described above, but without gelling agents for at least 3 hours prior to placing the filters on the nurse cultures.

Nurse cultures are prepared from Black Mexican Sweet Corn suspension culture (BMS) [Green, *Hort. Sci.*, 12 (1977) 131; Smith et al., *Plant Sci. Lett.*, 36 (1984) 67], or the embryogenic suspensions described in example 3.

When BMS is used as a nurse, sterile KM media with 0.5 mg/liter 2,4-D and 100 mg/liter O-acetyl-salicylic acid (2 mg/ml in 2% v/v DMSO containing 0.1% w/v MES, pH 6.0) is added to sterile SeaPlaqu® agarose to give a final concentration of agarose of 1.2% w/v. After heating to melt the agarose, the medium is cooled to 44° C. in a water bath, 1 ml PCV of BMS suspension added per 10 ml of medium, and 5 ml aliquots distributed into 60 mm diameter petri dishes. When the medium has solidified, sterile Durapore filters are placed on the surface, numbered side up.

When embryogenic corn suspension cultures are used as nurse, N6 media is increased in osmolality using glucose to ≈530–540 mOs/kgH$_2$O. The pH is re-adjusted to 6.0, and media is filter-sterilized through a 0.2 μm filter. 0.5 mg/liter 2,4-D and 100 mg/liter O-acetyl-salicylic acid (2 mg/ml in 2% v/v DMSO containing 0.1% w/v MES, pH 6.0) is added. The medium is added to sterile SeaPlaque® agarose to give a final concentration of agarose of 1.2% w/v. After heating to melt the agarose, the medium is cooled to 44° C. in a water bath, 1 ml PCV of the embryogenic suspension culture added per 10 ml of medium, and 5 ml aliquots distributed into 60 mm diameter petri dishes. When the medium has solidified, sterile Durapore filters are placed on the surface, numbered side up.

The protoplast preparation is diluted with cooled (44° C.) KM medium with 1.2% w/v SeaPlaque® agarose, containing 0.5 mg/liter 2,4-D and 100 mg/liter O-acetyl-salicylic acid to a concentration of 0.5 million protoplasts/ml. 0.5 ml of this preparation is pipetted slowly onto the surface of each of the filters.

Example 8t

Transformation of *Zea Mays* protoplasts by electroporation.

Examples 8a–8s are repeated with the modification that calf thymus carrier DNA is not added.

Example 8u

Transformation of *Zea mays* protoplasts by electroporation.

Examples 8a–8t are repeated with the modification that 50 micrograms of linearized pCIB712 plasmid is added.

Example 8v

Transformation of *Zea mays* protoplasts by electroporation.

Examples 8a–8u are repeated with the modification that the plasmid pCIB712 is not linearized.

Example 8w

Transformation of *Zea mays* protoplasts by electroporation.

Examples 8a–8v are repeated with the modification that the plating density of protoplasts is 2.0–2.5 million/ml.

Example 8x

Transformation of *Zea mays* protoplasts by electroporation.

Examples 8a–8w are repeated with the modification that the protoplasts are treated with a heat shock for 4 minutes.

Example 8y

Transformation of *Zea mays* protoplasts by electroporation.

Examples 8n–8w are repeated with the modification that the protoplasts are washed with the W6 solution instead of W5 solution of Example 8n. Solution W6 consists of 9 g/l each of CaCl$_2$.2H$_2$O, NaCl and glucose, and 1 g/l MES, pH 7.0.

Example 9a

Transformation of *Zea mays* protoplasts by treatment with polyethylene glycol.

The protoplasts are resuspended at the last step of example 3 in a 0.5M mannitol solution containing 12 to 30 mM MgCl$_2$. A heat shock of 45°·C. for 5 minutes is given as described in Example 8a or 8x.. The protoplasts are distributed in aliquots for transformation in centrifuge tubes, 0.3 ml of suspended protoplasts per tube. During the next 10 minutes the following are added: DNA (as for Example 8a–8v) and PEG solution (PEG 6000 40% w/v; Ca(NO$_3$)$_2$ 0.1M; mannitol 0.4M; pH 8–9 with KOH) comprising a final concentration of 20% w/v. The aliquots are incubated for 30 minutes with occasional gentle shaking and then the protoplasts placed in petri dishes (0.3 ml original protoplast suspension per 6 cm diameter dish) and cultured as described in Examples 8a or 8o–8w.

Example 9b

Transformation of *Zea mays* protoplasts by treatment with polyethylene glycol.

The protoplasts are resuspended at the last step of example 3 in a 0.5M mannitol solution containing 12 to 30 mM MgCl$_2$ at a density of 20 million protoplasts/ml. A heat shock of 45° C. for 4 minutes is given as described in Example 8a or 8x. The protoplasts are distributed in aliquots for transformation in centrifuge tubes, 0.5 ml protoplasts per tube. During the next 10 minutes. the following are added: DNA (as for Example 5a) and PEG solution (PEG 8000 [Sigma or other equivalent brand], 36% w/v, 0.1M Ca(NO$_3$)$_2$, 0.4M mannitol, 0.1% MES, adjusted over a period of 3 hours to pH 7 to 8 with KOH filter sterilized through a 0.2 μm filter) to a final concentration of 18% w/v. The aliquots are incubated for 30 minutes with gental shaking and then the protoplasts placed in petri dishes and cultured as described in Example 8a–8s.

Example 9c

Transformation of *Zea mays* protoplasts by treatment with polyethylene glycol.

Examples 9a and 9b are repeated and the protoplasts are washed after the 30 minute incubation in PEG by adding 0.3 ml of W5 solution of Example 8n 5 times at 2 to 3 minutes intervals, they are then centrifuged, the supernatant is removed, and the protoplasts cultured as for Examples 8a–8w.

Example 9d

Transformation of *Zea mays* protoplasts by treatment with polyethylene glycol.

Alternatively, the protoplasts are washed by the consecutive addition of 1 ml, 2 ml and 5 ml of W5 solution of Example 8n at 5 minute intervals. They are then centrifuged, the supernatant is removed, and the protoplasts cultured as for Examples 8a–8w.

Example 9e

Transformation of *Zea mays* photoplasts by treatment with polyethylene glycol.

Examples 9a to 9d are repeated with the modification that the final concentration of PEG is 15% w/v.

Example 9f

Transformation of *Zea mays* protoplasts by treatment with polyethylene glycol.

Examples 9a to 9e are repeated with the modification that the final concentration of PEG is 25% w/v.

Example 9g

Transformation of *Zea mays* protoplasts by treatment with polyethylene glycol.

Examples 9a to 9d are repeated with the modification that the final concentration of PEG is 12% w/v.

Example 9h

Transformation of *Zea mays* protoplasts by treatment with polyethylene glycol.

Examples 9b–9f are repeated with the modification that the protoplasts are washed with KMC salt solution according to Example 8n.

Example 9i

Transformation of *Zea mays* protoplasts by treatment with polyethylene glycol.

Examples 9b–9h are repeated with the modification that the protoplasts are washed with W6 salt solution according to Example 8y.

Example 10a

Regeneration of callus from protoplasts.

The plates containing the protoplasts in agarose are placed in the dark at 26° C. Within 14 days, cell colonies arise from the protoplasts. The agarose containing the colonies is transferred to the surface of a 9 cm diameter petri dish containing 30 ml of N6 medium with 2 mg/liter 2,4-D, solidified with 0.24% w/v Gelrite® (2N6). The colonies are cultured to give callus. The callus is cultured further in the dark at 26° C. and callus pieces subcultured every 2 weeks onto fresh N6 medium containing 2 mg/liter 2,4-D (solidified with 0.24% w/v Gelrite®).

Example 10b

Regeneration of callus from protoplasts.

The plates containing the protoplasts on the nurse cultures are placed in the dark at 26° C. In about 2 weeks, colonies will have appeared. Whole filters are then transferred to the surface of a 9 cm diameter petri dish containing N6 medium with 2 mg/liter 2,4-D, solidified with 0.24% w/v Gelrite® (2N6), or colonies are picked off and transferred individually to this medium. The callus which arises is cultured further in the dark at 26° C. and callus pieces subcultured every 2 weeks onto fresh N6 medium containing 2 mg/liter 2,4-D (solidified with 0.24% w/v Gelrite®).

Example 10c

Regeneration of callus from protoplasts of Funk genotype 5N984.

The plates containing the protoplasts, derived from suspension cultures of elite genotype Funk 5N984 on the nurse cultures are placed in the dark at 26° C. In about 2 weeks, colonies will have appeared. Whole filters are then transferred to the surface of a 9 cm diameter petri dish containing KMX medium, or colonies are picked off and transferred individually to this medium. The callus which arises is cultured further in the dark at 26° C. and callus pieces subcultured every 2 weeks onto fresh KMX medium.

Example 11a

Selection of transformed callus of *Zea mays*.

Examples 10a and 10b are repeated with the modification that 50 mg/liter hygromycin B is added to the 2N6 medium in order to select for transformed cells.

Example 11b

Selection of transformed callus of *Zea mays*.

Examples 10a and 10b are repeated with the modification that 100 mg/liter hygromycin B is added to the 2N6 medium in order to select for transformed cells.

Example 11c

Selection of transformed callus of *Zea may*.

Examples 10a and 10b are repeated with the modification that 200 mg/liter hygromycin B is added to the 2N6 medium in order to select for transformed material.

Example 12a

Regeneration of plants.

Callus is placed on 2N6 for maintenance and on ON6 (N6 medium without hormones) and N61 (0.25 mg/liter 2,4-D +10 mg/liter kinetin) to initiate regeneration. Material growing on ON6 and N61 medium is grown in the light (16 hours/daylight of 10 to 30 $\mu E/m^2 sec$ from white fluorescent lamps). Callus growing on N61 is transferred to ON6 after 2 weeks, as prolonged time on the N61 plates is detrimental. The callus is subcultured every 2 weeks even if the callus is to be transferred again on the same medium formulation. Plantlets take 4 to 8 weeks to appear.

Once the plantlets are at least 2 cm tall, they are transferred to ON6 medium in GA7 containers or other suitable culture vessels. Roots form in 2 to 4 weeks. Once the roots look to be well formed enough to support growth, the plantlets are transferred to soil in peat pots, under a light shading for the first 4 to 7 days. It is often helpful to invert a clear plastic cup over the transplants for several days.

Once the plants are established, they are treated as normal *Zea mays* plants and grown in the greenhouse to maturity to test for fertility and the inheritance of the introduced genes.

Example 12b

Regeneration of plants.

Examples 12a is repeated with the following modification. The N61 medium is replaced by N6 or MS media containing 1, 5 or 10 mg/l kinetin, or 1, 5, or 10 mg/l Benzylaminopurine. The callus is randomized and 16 peices per plate, 2 plates per treatment are used. The callus is left on the hormone for 2 weeks and then transferred to the corresponding basal medium without hormone. Callus is subsequently transferred every 2 weeks on this medium. Plantlets are transferred to Plantcons with ½ strength MS salts, full strength MS vitamins and 3% sucrose. When root growth appeared sufficient the plants are transferred to a mist bed in the greenhouse. The number of plantlets recovered in one experiment, and the plants which are placed in soil are shown in table 2.

TABLE 2

Plants regenerated and potted in soil mixture from treatment of protoplast-derived maize callus with BAP or kinetin and 2,4-D on two basal media (MS and N6).

| Basal medium | 2,4-D (mg/l) | BAP (mg/l) | | | | Kinetin (mg/l) | | | Zeatin (mg/l) | | |
|---|---|---|---|---|---|---|---|---|---|---|---|
| | | 0 | 1 | 5 | 10 | 1 | 5 | 10 | 0.1 | 0.5 | 1 |
| MS | 0 | 24 | 5 | 16 | 41 | 9 | 85 | 1 | 7 | 13 | 7 |
| MS | 0.25 | 34 | 26 | 16 | 162 | 38 | 115 | 3 | 38 | 5 | 11 |
| N6 | 0 | 0 | 2 | 0 | 0 | 0 | 4 | 0 | 1 | 0 | 1 |
| N6 | 0.25 | 0 | 0 | 16 | 0 | 0 | 23* | 0 | 4 | 5 | 0 |

*This medium is that described as N61 in example 12a.

Example 12c

Regeneration of plants.

Examples 12a and 12b are repeated with the modification that 50 mg/liter hygromycin B is added to the medium used to maintain callus.

Example 12d

Regeneration of plants.

Examples 12a and 12b are repeated with the modification that 100 mg/liter hygromycin B is added to the medium used to maintain the callus.

Example 12e

Regeneration of plants.

Examples 12a and 12b are repeated with the modification that 200 mg/liter hygromycin B is added to the medium used to maintain the callus.

Example 13

Transformation and Regeneration.

Examples 8, 9, 10, and 11 are repeated with the only modifications that plasmid pCIB10/35SBt is used as the plasmid DNA, and that the antibiotic G418 is substituted for hygromycin on the selection steps.

Example 14

Construction of pIRV, containing both the chimeric hygromycin-resistance and chimeric BT genes.

Plasmid pCIB 712 is digested with SmaI. Plasmic pCIB10/35S Bt is digested with SphI, treated with large fragment of DNA polymerase (Klenow enzyme) to create flush ends, then digested with SmaI. The approximately 4.8 kb fragment containing the chimeric BT gene is purified by agarose gel electrophoresis, and ligated to SmaI-cleaved pCIB 712 DNA. The resulting plasmid, pIRV, contains both the chimeric hygromycin-resistance gene and the chimeric Bt gene. pIRV is linearized at an appropriate site distal to the chimeric genes prior to electropotation.

Example 15

Transformation and Regeneration

Examples 8, 9, 10, and 11 are repeated with the modification that plasmid pIRV is used as plasmid DNA and hygromycin is used in selection.

Example 16

Construction of plasmid bearing chimeric chitinase and chimeric hygromycin resistance genes.

A cDNA clone, pSCH1 containing the coding region of a tobacco chitinase gene is identified in a library of tobacco cDNA's cloned into the Pst1 site of pBR322. Hybrid-selected translation gives a protein product that cross-reacts with antibody raised against bean chitinase [Shinshi et al., *Proc. Natl. Acad. Sci. USA* 84 (1987) 89–93]. From a lambda library of tobacco DNA, the corresponding genomic clone is identified using the cDNA clone as probe [Maniatis, op.cit.]. Hybridization and restriction mapping studies are used to identify a Pst1 site common to the cDNA clone and the genomic clone.

Sequence analysis of genomic DNA upstream from this common Pst1 site reveals the start of the open reading frame for the chitinase structural gene, as well as a SphI recognition site at a position −35 from that start site. The following steps are used to join this upstream genomic DNA fragment to the downstream cDNA fragment forming a full-length coding region for chitinase:

a/ The full length gene is constructed in a plasmid vector pGY1, which contains a CaMV 35S promoter fragment, a termination/poladenylation signal from CaMV and a poiylinker between these two. The polarity of the polylinker forces the orientation of the upstream fragment; correct orientation of the downstream fragment is determined by sequence analysis.

The upstream SphI/PstI fragment from the genomic clone is isolated and purified; it is then ligated into plasmid pGY1 which has been digested with SphI and PstI.

b/The resulting intermediate plasmid is digested with PstI. The downstream PstI fragment is isolated from clone pSCH1 and ligated into this digested intermediate vector.

c/ The clone having the correct orientation and in-frame fusion of the cDNA fragment to the upstream genomic DNA fragment is confirmed by DNA sequence analysis. The resulting plasmid is named pSCH1. The plasmid pSCH1 [in *E. coli* strain K12] is on deposit at the Deutsche Sammlung yon Mikroorganismen in Goettingen, W. Germany, accession number DSM 4129. This deposition was made in accordance with the requirements of the Budapest Treaty [date of deposit: May 29, 1987]. The complete chitinase gene flanked by the CaMV 35S promoter and terminator regions is excised from pSCH1 by EcoRI digestion. The fragment is rendered blunt-ended by use of the large fragment of DNA polymerase I [Maniatis, op. cit]. The receptor plasmid pCIB 712, which contains a chimeric hygromycin resistance gene that expresses in plant cells, is digested with SmaI. The SmaI-digested pCIB712 and the blunt-ended fragment containing the chimeric chitinase gene are ligated together using T4 ligase [Maniatis, op.cit]. The resulting plasmid is named pCIBcht. Prior to protoplast transformation, pCIBcht is linearized at a site distal to the chimeric genes.

Example 17

Construction of vector bearing chimeric AHAS gene conferring sulfonylurea resistance.

a. Isolation of Sulfonylurea-resistant (SU-R) Arabidopsis plants.

Ethylmethanesulfonate (EMS) mutagenized M2 *Arabidopsis thaliana* (race Columbia) seeds are produced according to Haughn and Somerville [*Mol. Gen. Genet.* 204 (1986) 430–434] and Somerville and Ogren (*Methods in Chloroplast Molecular Biology*, Edelman et al. (eds) (1982) 129–138.) The EMS is used at 0.3% concentration for 14 to 16 hours and the M1 seeds are sown and grown at a density of 2 to 3 plants per $cm^2$.

Sulfonylurea-resistant (SU-R) Arabidopsis plants are selected and grown from the M2 seed stocks according to aughn and Somerville (op. cit.).

b. Construction of recombinant lambda phage library of SU-R Arabidopsis DNA.

DNA is isolated from SU-R Arabidopsis plants according to Jen and Chilton [*J. Bacteriol.*, 166 (1986) 491–499.] Arabidopsis DNA is completely digested with XbaI (New England Biolabs). DNA fragments of size 4 to 8 kbp in length are isolated from an agarose gel using an NA45 DEAE membrane (Schleicher and Schuell, Keene, N. H. Catalog No. 03431) and cloned into lambda-ongC-X vector (Stratagene, 3770 Tansy St., San Diego, Calif. 92121) using manufacturer's recommended procedures. Recombinant phage DNA is encapsidated using Gigapack-plus kit from Stratagene.

c. Cloning of SU-R acetohydroxy acid synthase (AHAS) gene from SU-R Arabidopsis plants.

Plasmid pE16/8-c4 which contains the ILV2 locus of *Saccharomyces cerevisiae* [J. Polaina, *Carlsberg Res. Comm.* 49 (1984) 577–584.] is obtained from J. Polaina, is transformed into *E. coli* HB101, and a large-scale plasmid preparation is made. Plasmid pE16/8-c4 is on deposit with the American Type Culture Collection, accession number 67420. This deposition was made in accordance with the requirements of the Budapest Treaty [date of deposit: May 29, 1987]. Plasmid pE16/8-c4 DNA is digested with EcoRI and the 2.1 kbp (Eco 2.1) fragment containing the AHAS coding sequence [Falco et al., *Nucl. Acid Res.* 13 (1985) 4011–4027.] is isolated from an agarose gel. Eco 2.1 fragment is radiolabelled with 32-phosphorus to a specific activity of 5 to $8 \times 10^8$ cpm/µg with PRIME TIME kit (International Biotechnologies, Inc.).

Recombinant phages containing Arabidopsis XbaI fragments are plated on *E. coli* VCS 257 according to Maniatis et al., (1982) [Cold Spring Harbor, N.Y.] and Stratagene protocols.

Duplicate lambda plaque lifts are made of each phage plate with Colony/PlaqueScreen® membrane (New England Nuclear Research Products) according to the manufacturer's protocol. Plaque lifts are treated as follows:

i/ washed in 5× SSC, 2% SDS at 65° C. for 6 hours, [all recipes are as in Maniatis et al,(op. cit.);

ii/ prehybridized in hybridization mix (5× SSC, 1% SDS, 5× Denhardt's solution, 200 µg/ml of denatured and sheared salmon DNA, 25% formamide, 10% dextran sulfate; 10 ml of mix per 150 mm membrane) at 42° C. for 16 to 20 hours;

iii/hybridized in hybridization mix (10 ml per 150 mm membrane) containing 2 ng/ml of denatured radiolabelled Eco 2.1 fragment at 42° C. for 18 to 20 hours;

iv/ washed in 2× SSC, 1% SDS at room temperature for 30 minutes;

v/ washed in 5× SSC, 1% SDS, 25% formamide at 42° C. for 6 to 8 hours with four changes of the wash solution.

The membranes are exposed to X-Ray film (Kodak X-Omat AR). Phage plaques showing coincident hybridization on the duplicate membranes are purified with a second round of lambda plaque lifts and hybridization with the Eco 2.1 probe.

Plate lysates of recombinant phage containing insert homologous to yeast AHAS sequences are prepared according to Maniatis et al. (supra). Phage DNA is prepared from plate lysates with LambdaSorb (Promega, 2800 S. Fish Hatchery Rd., Madison, Wis. 53711) according to manufacturer's recommended procedures.

d. Construction and verification of transformation vector pCIB803 containing SU-R Arabidopsis AHAS gene.

The recombinant phage DNA is digested with XbaI and the 5.8 kbp insert fragment is cloned into a XbaI-digested pCIB10 transformation vector to yield pCIB803. Plasmid pCIB803 is transferred from the *E. coli* HB101 host to *Agrobacterium tumefaciens* CIB542 by triparental mating [Ditta et al., *Proc. Acad. Sci. USA*, 77 (1980) 262–269]. *A. tumefaciens* pCIB803/CIB542 is used to transform *Arabidopsis thaliana* leaf explants according to Lloyd et al. [*Science* 234 (1980) 464–466] and Sheikholeslam and Weeks [*Plant Molec. Biol.* 8 (1987) 291–298]. Transformed tissues are regenerated into plants according to Lloyd et al. (op.cit.) and Feldman and Marks [*Plant Sci.*, 47 (1986) 63–69]. The growth of transformed tissues in culture medium is shown to be tolerant to 3 to 10 ng/ml of chlorsulfuron. The germination and growth of transgenic Arabidopsis plants in agar media are shown to be tolerant of 10 to 30 ng/ml of chlorsulfuron.

e. Construction of transformation vector pCIB804 containing a chimeric SU-R AHAS gene.

The location of the AHAS coding sequence within the Xba 5.8 fragment is determined by nuclease-S1 mapping [*Maniatis* et al., op. cit.], primer extension [McKnight et al., *Cell*, 25 (1981) 385–398] and is verified by DNA sequencing [Sanger et al., *Proc. Nat. Acad. Sci. USA* 74 (1977) 5463–5467] and protein sequence comparisons to bacterial and yeast AHAS sequences [Falco et al., *Nucl. Acid Res.* 13 (1985) 4011–4027]. The 5.8 kb XbaI fragment is cloned into Bluescript (Strategene) and sequences upstream of the AHAS coding sequence are deleted to within 10 to 20 bp upstream of the AHAS initiation codon using the Exo/Mung Deletion kit (Strategene). An appropriate linker is attached to the deletion end point. The resected AHAS gene is cut at an appropriate restriction site at least 10 bp downstresm of the AHAS termination codon and the same linker used at the 5'-end of the gene is attached at the 3'-end of the gene. The fragment containing the AHAS coding sequence is excised from the vector by cutting at the linker sites and is cloned into the BamHI site of pCIB710.

The BamHI site of pCIB710 is adapted or converted to a site compatible with the linker used above as necessary in order to receive the linkered SU-R AHAS gene. The orientation of the AHAS gene insert in pCIB710 is determined with appropriate restriction enzymes. The clone containing the AHAS coding sequence correctly oriented with respect to the transcriptional direction of CaMV 35S promoter is designated pCIB804.

Example 18

Promotion of callus formation from protoplasts of *Zea mays* by 2,4-D and acetyl-salicylic acid Protoplasts are resuspended in the last step of example 3 in 6/7 strength KMC solution at 7.5 million per ml.

The O-acetyl-salicylic acid is dissolved at 2.5 mg/ml in KM medium. The solution is filter sterilized. The O-acetyl-salicylic acid is then added to the culture medium immediately before use. Aliquots of protoplast suspension are placed in 6 cm diameter petri dishes at room temperature. 3 ml of KM medium containing 1.2% w/v SeaPlaque® agarose, 2,4-D and O-acetyl salicylic acid is added so as to give the correct 2,4-D and O-acetyl-salicylic acid concentrations and a protoplast density of 0.5 million per ml. The agarose and protoplasts are mixed well, and the medium allowed to gel.

The dishes are cultured as described in example 7. After a period of 3 weeks, macroscopic colonies arising in the dishes are counted. The results are shown in tables 2 and 3 for protoplasts from two different independently obtained embryogenic suspension cultures.

TABLE 3

Colony formation of *Zea mays* protoplasts in the presence of O-acetyl-salicylic acid and 2,4-D.
[numbers are the numbers of colonies formed]

| 2,4-D | O-acetyl-salicylic acid (mg/l) | | | | | |
|---|---|---|---|---|---|---|
| (mg/liter) | 0 | 1 | 3 | 10 | 30 | 100 |
| 0 | 0 | 0 | 0 | 4 | 13 | 1 |
| 0.3 | 63 | 2 | 6 | 15 | 83 | 146 |
| 1.0 | 9 | 7 | NT | 20 | 64 | 215 |
| 3.0 | 3 | 1 | 0 | 6 | 45 | 111 |

NT: Not tested

TABLE 4

Colony formation of *Zea mays* protoplasts in thepresence of O-acetyl-salicylic acid and 2,4-D.
[numbers are numbers of colonies formed]

| 2,4-D | O-acetyl-salicylic acid (mg/l) | | | | | |
|---|---|---|---|---|---|---|
| (mg/liter) | 0 | 1 | 3 | 10 | 30 | 100 |
| 0 | 0 | 1 | 0 | 0 | 0 | 0 |
| 0.3 | 0 | 0 | 0 | 0 | 0 | 2 |
| 1.0 | 1 | 1 | 2 | 21 | 31 | 38 |
| 3.0 | 0 | 3 | 1 | 9 | 41 | 34 |

Figure 7A:
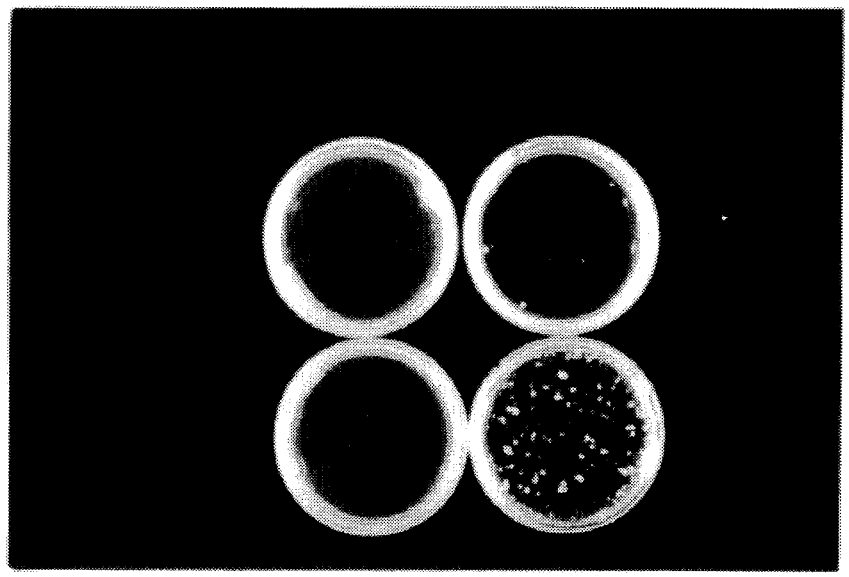
FIG. 7a shows colonies arising from *Zea mays* protoplasts plated in KM medium with and without 2,4-D and acetyl-salicylic acid. Upper left: no 2,4-D or acetyl-salicylic acid.
  Upper right: 1 mg/liter 2,4-D and no acetyl-salicylic acid.
  Lower left: 100 mg/liter acetyl-salicylic acid and no 2,4-D.
  Lower right: 100 mg/liter acetyl-salicylic acid and 1 mg/liter 2,4-D.
Figure 7B:
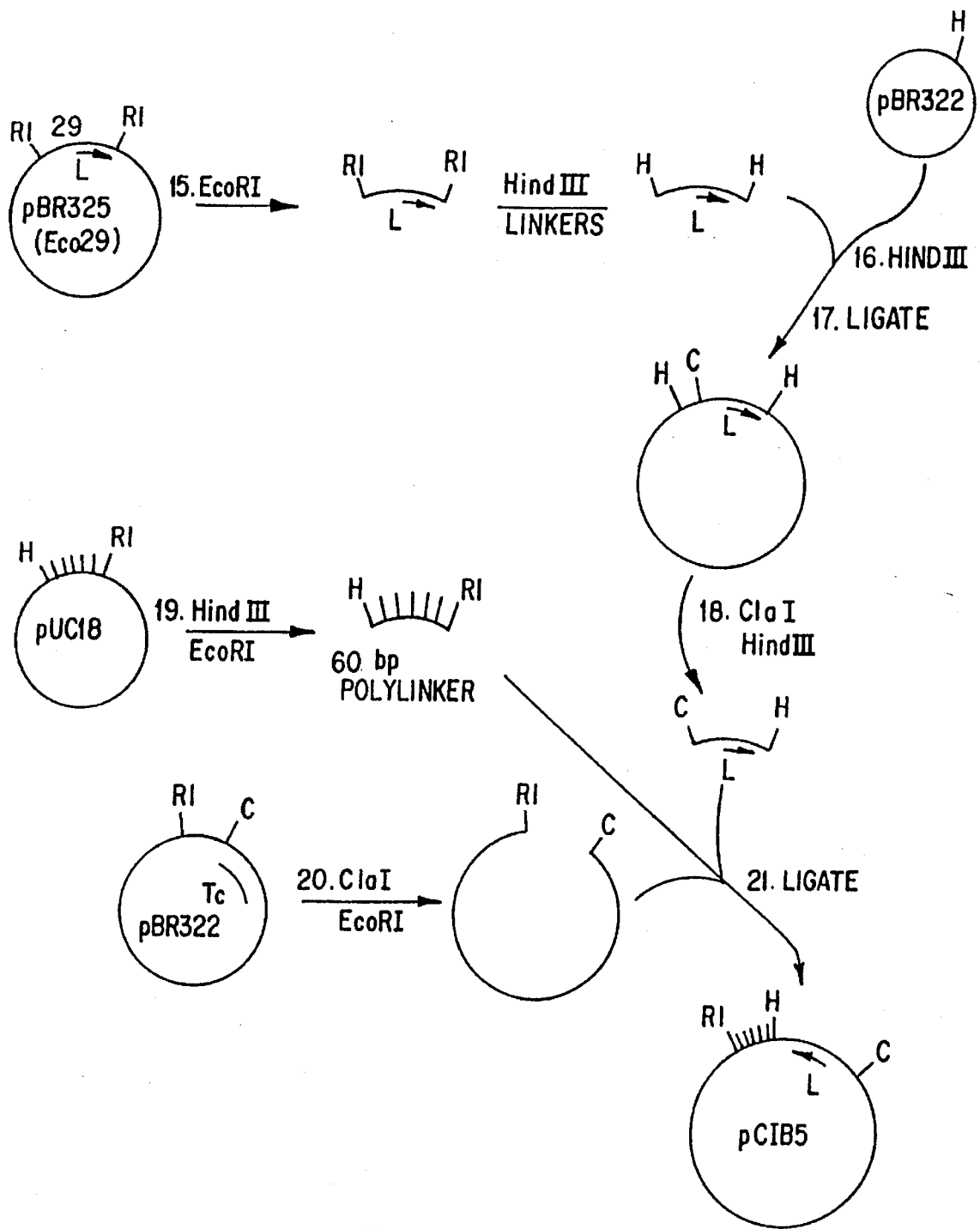
FIG. 7b shows the construction of pCIB5.
Figure 7C:
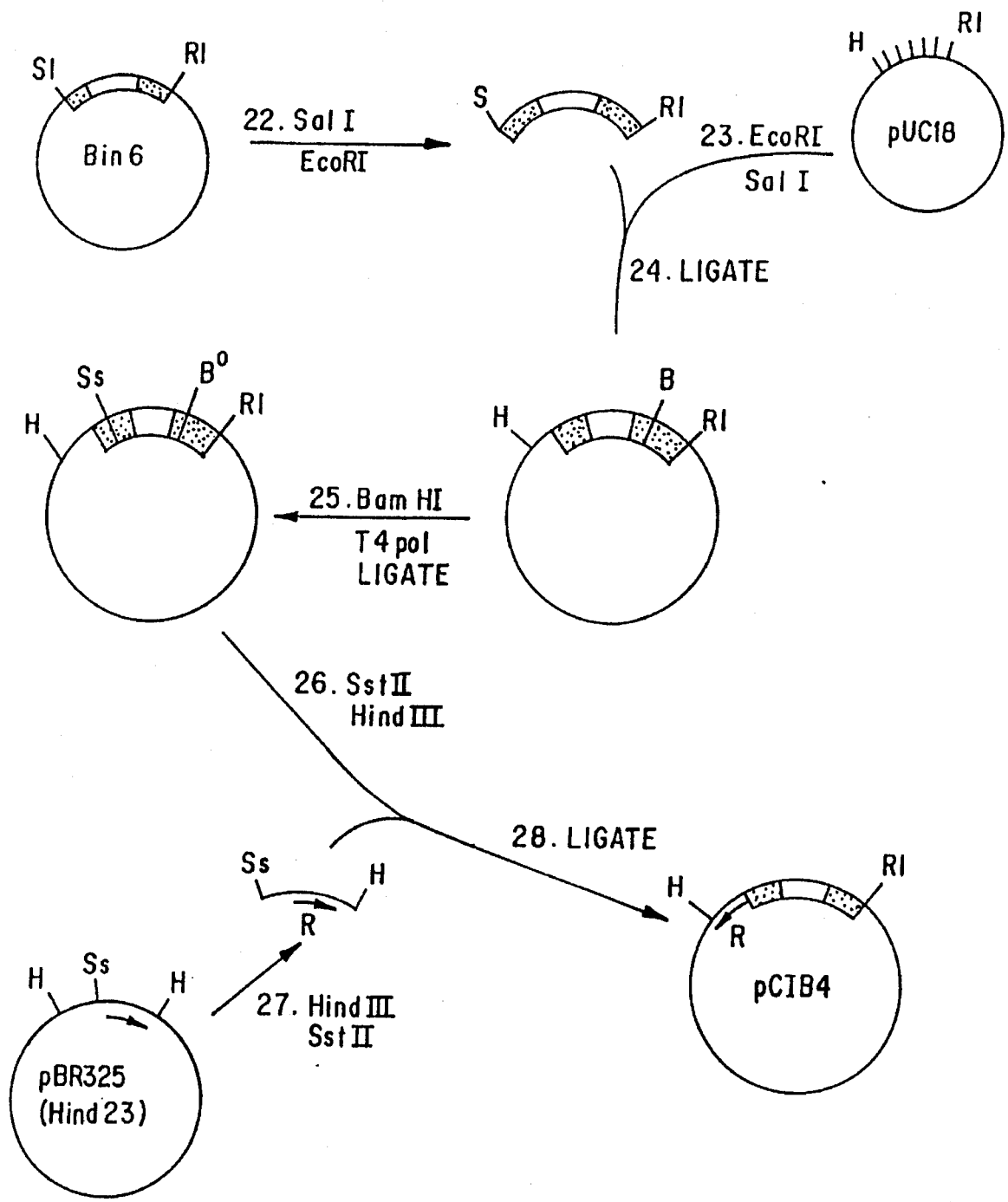
FIG. 7c shows the construction of pCIB4.
Figure 7D:
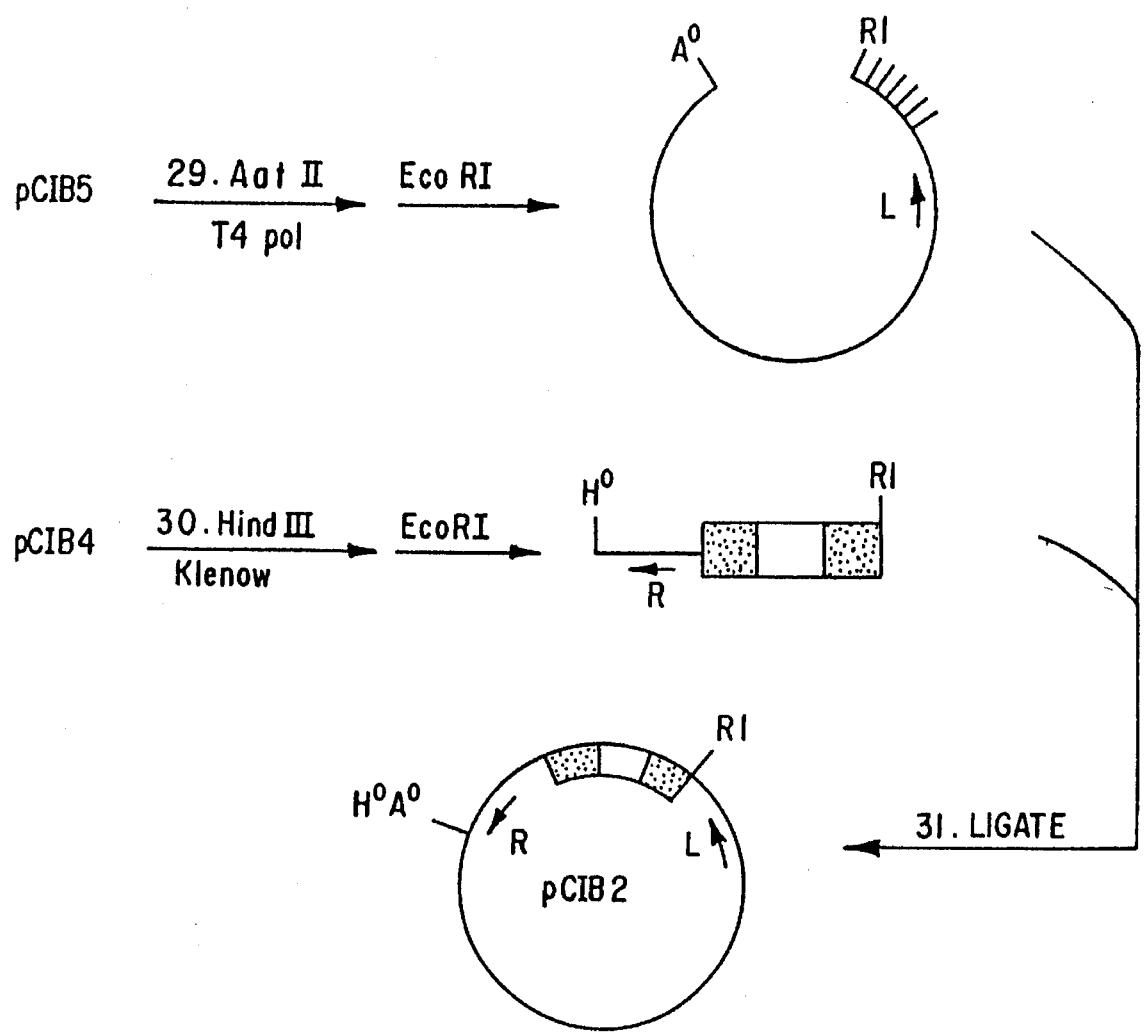
FIG. 7d shows the construction of pCIB2.
Figure 7E:
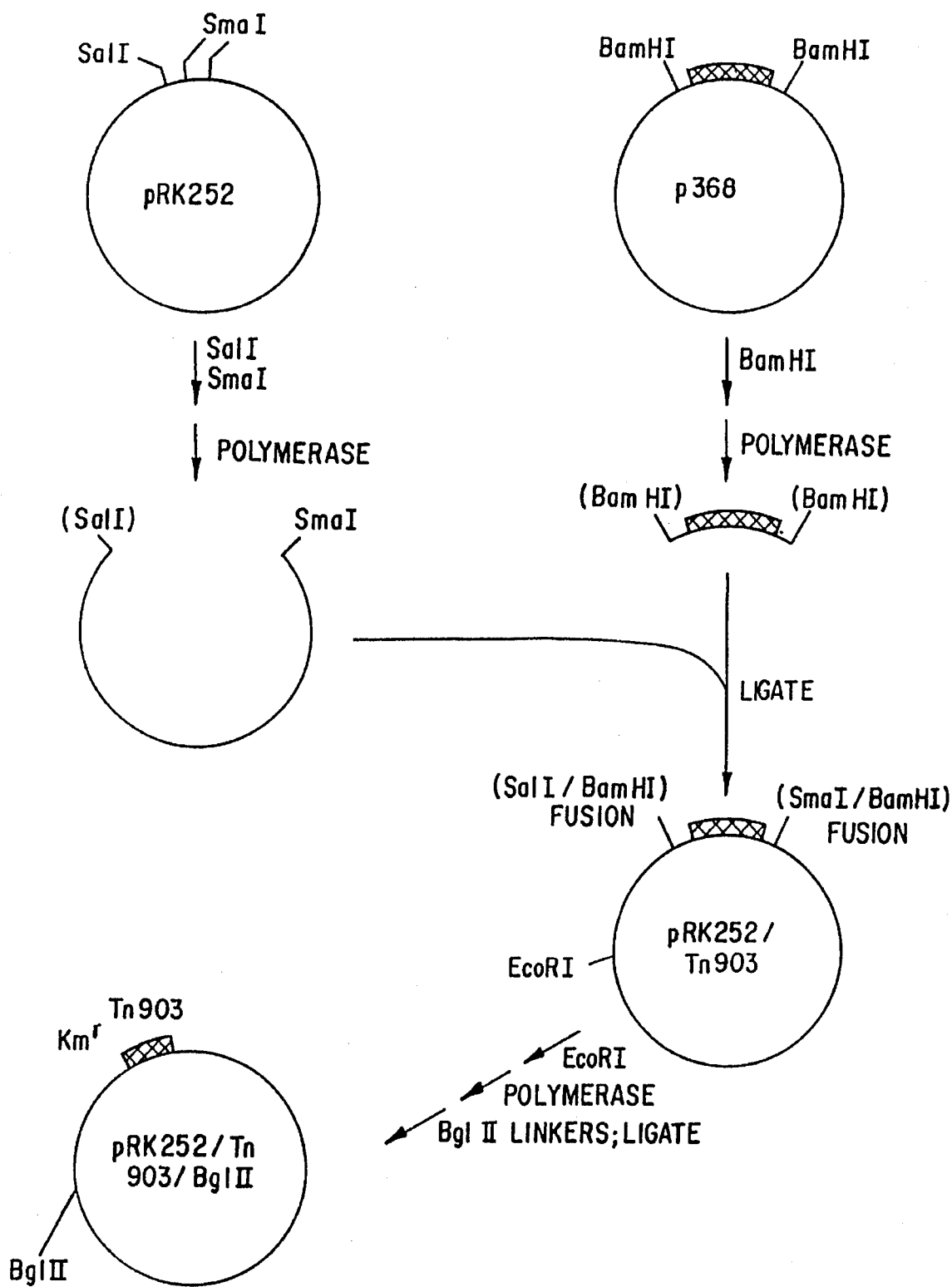
FIG. 7e shows the construction of pRK252Km.
Figure 7F:
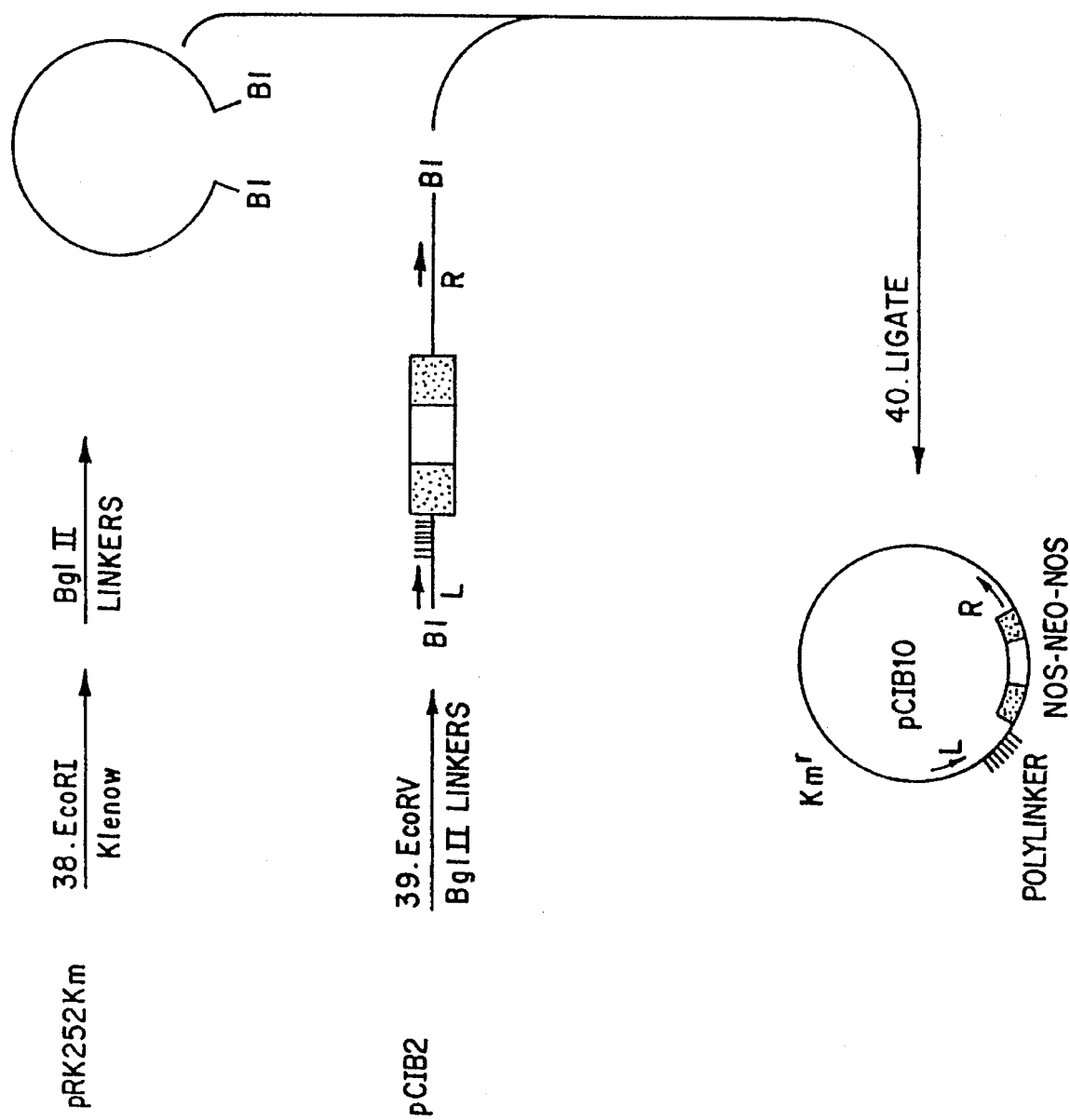
FIG. 7f shows the construction of pCIB10.
Figure 7G:
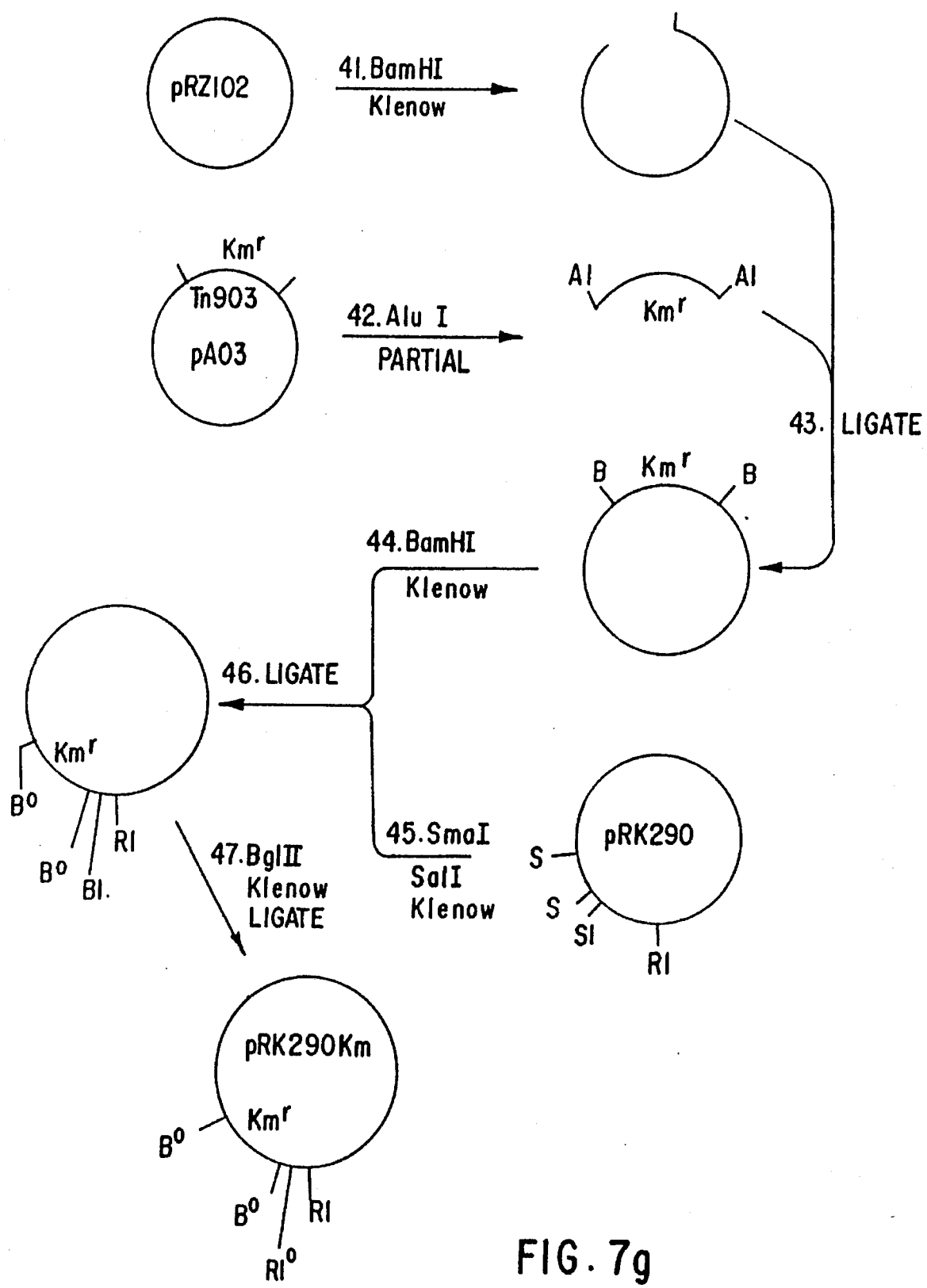
FIG. 7g shows the construction of pRK290Km.
Figure 7H:
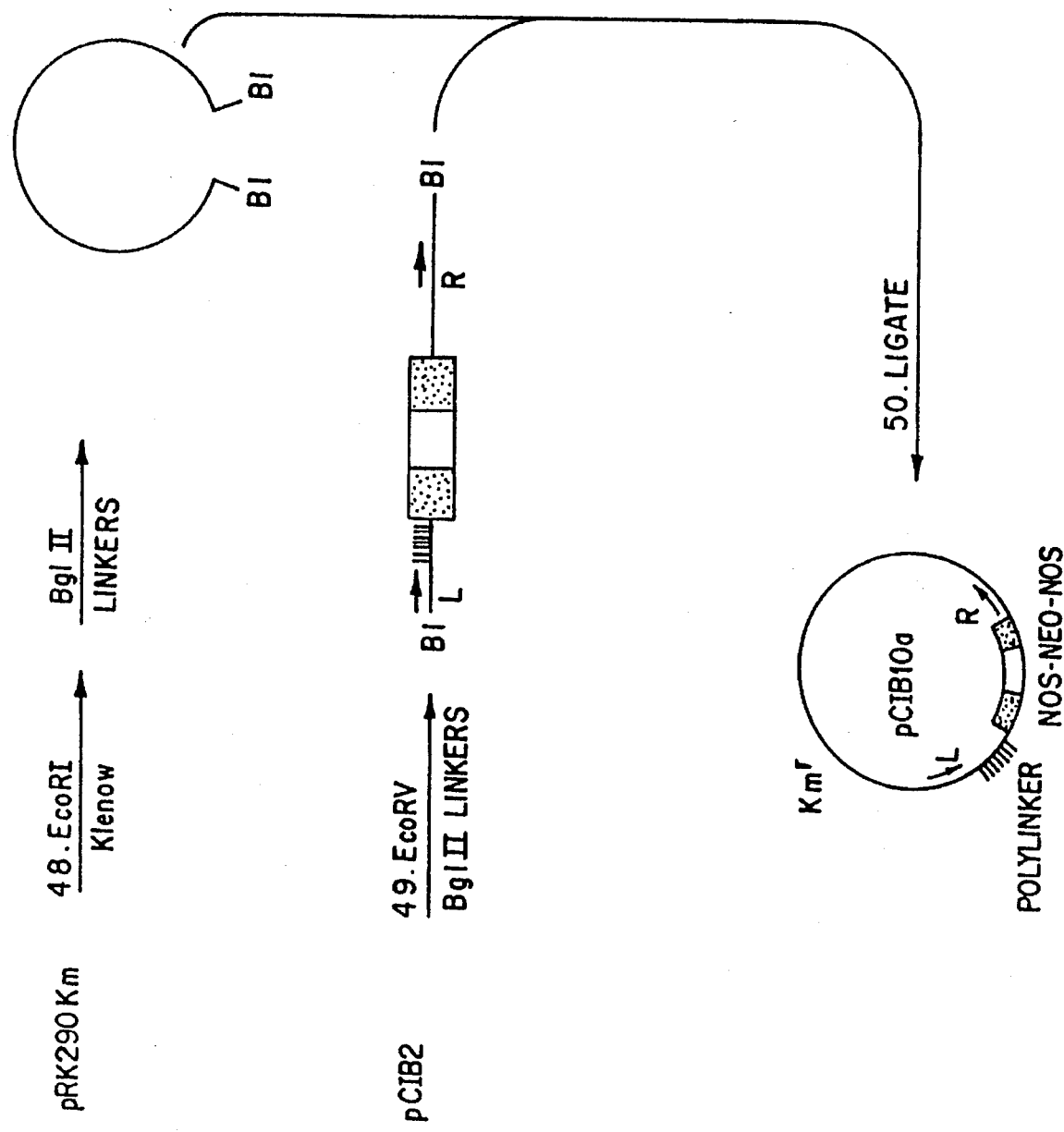
Figure 9:
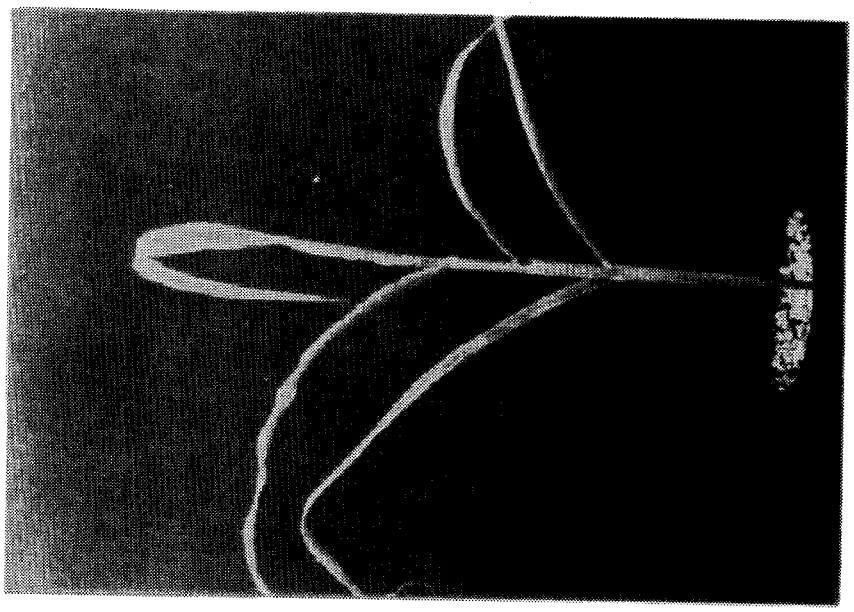
FIG. 9 shows a *Zea mays* plant regenerated from protoplast-derived callus.
Figure 8:
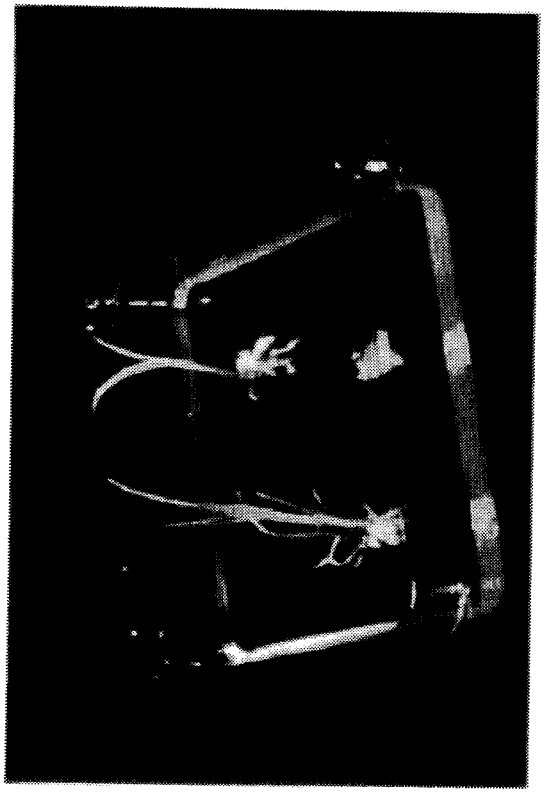
FIG. 8 shows plantlets regenerated from protoplast-derived callus of *Zea mays*.
Figure 10:
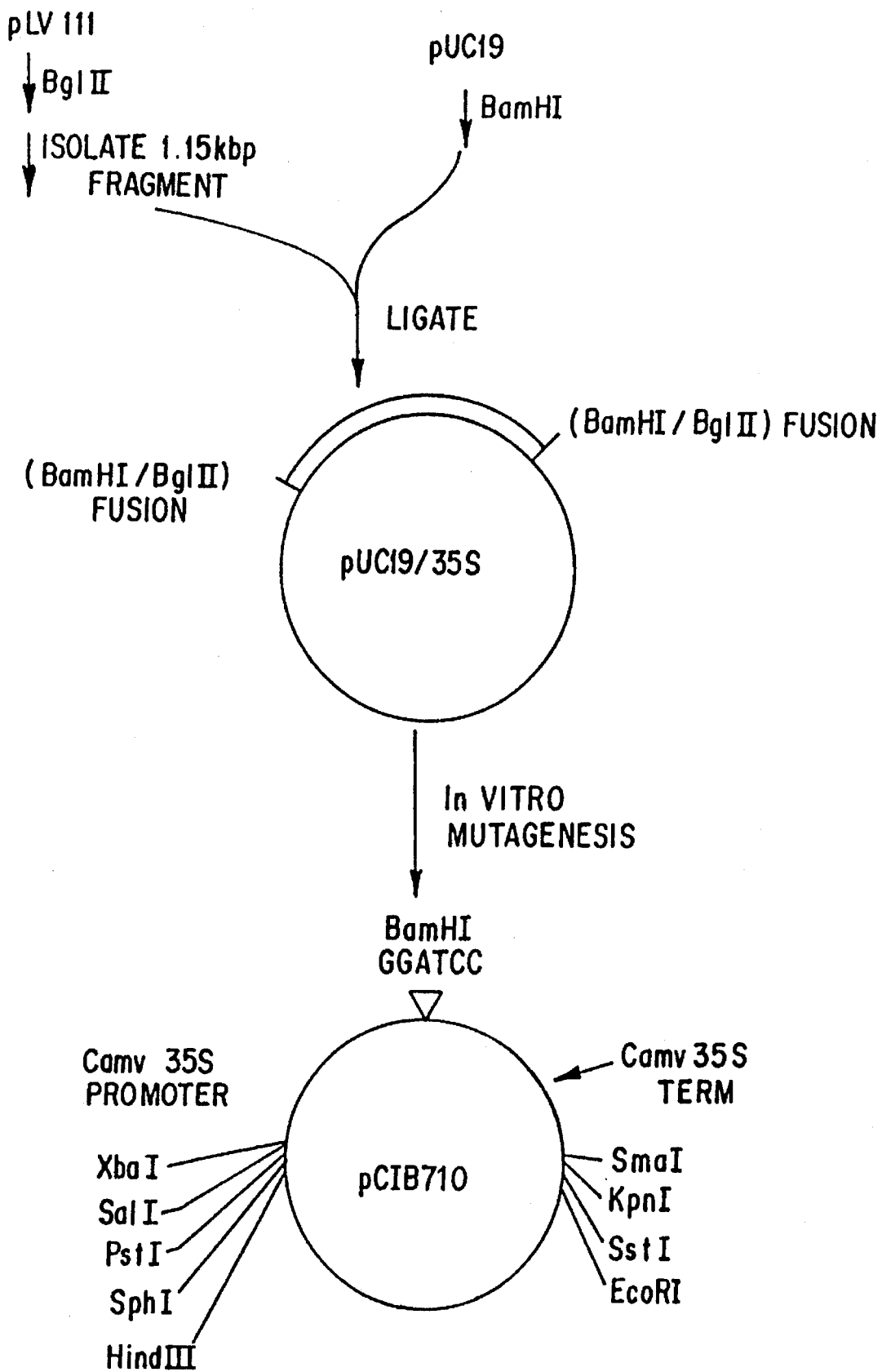
FIG. 10 shows the construction of plasmid pCIB710.

FIG. 7a: Colonies arising from *Zea mays* protoplasts plated in KM medium with and without 2,4-D and acetyl-salicylic acid. Upper left: no 2,4-D or acetyl-salicylic acid.

Upper right: 1 mg/liter 2,4-D and no acetyl-salicylic acid.

Lower left: 100 mg/liter acetyl-salicylic acid and no 2,4-D.

Lower right: 100 mg/liter acetyl-salicylic acid and 1 mg/liter 2,4-D.

Example 19

Increased colony formation from protoplasts of *Zea mays* by addition of O-acetyl-salicylic acid and 2,4-D.

The protoplasts are prepared and plated for culture as described in example 18, in 2 ml of medium in 6 cm diameter petri dishes.

The dishes are cultured as described in example 10. After a period of 3 weeks, macroscopic colonies arising in the dishes are counted. The results are shown in table 4. O-acetyl-salicylic acid is again found to stimulate colony formation. However, at 300 mg/liter and above, a toxic effect is found. It is considered that this may be due to a pH problem and it may be that it can be overcome by appropriate buffering of the medium.

TABLE 5

Colony formation (per dish) of *Zea mays* protoplasts in the presence of O-acetyl-salicylic acid and 2,4-D.
[numbers are numbers of colonies formed]

| 2,4-D | O-acetyl-salicylic acid (mg/l) | | | | |
|---|---|---|---|---|---|
| (mg/liter) | 0 | 30 | 100 | 300 | 1000 |
| 0 | 0 | 0 | 0 | 0 | 0 |
| 0.3 | 32 | 212 | 438 | 0 | 0 |
| 1.0 | 72 | 405 | 327 | 0 | 0 |
| 3.0 | 18 | 25 | 69 | 0 | 0 |

Example 20

Promotion of colony formation from *Zea mays* protoplasts by DMSO and O-acetyl-salicylic acid in the presence of 2,4-D.

The protoplasts are prepared and plated at 0.75 million per ml as described in example 18, using 1 ml of medium per 3.5 cm diameter petri dish. O-acetyl-salicylic acid is included in the medium. The O-acetyl-salicylic acid is dissolved in DMSO and then added to the medium before plating of the-protoplasts. To obtain a solution in DMSO, 1 g of O-acetyl-salicylic acid is dissolved in 10 ml DMSO, and added to 90 ml distilled water. The solution is then filter sterilized before use.

The dishes are cultured as described in example 10. After a period of 3 weeks, macroscopic colonies arising in the dishes are counted. The results are shown in table 6. DMSO alone (1% v/v) gives no significant increase or decrease in colony forming efficiency of *Zea mays* protoplasts and apparently potentiates the stimulatory activity of the O-acetyl-salicylic acid.

TABLE 6

Effect of O-acetyl-salicylic acid on colony formation by *Zea mays* protoplasts, showing the stimulatory effect of dissolving the O-acetyl-salicylic acid in DMSO.
[number of formed colonies]

| 2,4-D acid/liter mg/liter | No additions | 100 mg acetyl-salicylic |
|---|---|---|
| 0 | 0 | 0 |
| 0.1 | 1 | 28 |
| 0.3 | 2 | 235 |
| 1.0 | 45 | >300 |

Example 21

Increasing colony formation of *Zea mays* proto plasts by addition of 2,4-D, and related plant growth regulators (auxins)

Protoplasts are resuspended in the last step of example 3 in 6/7 strength KMC solution at 5 million per ml. Aliquots of protoplast suspension are placed in 6 cm diameter petri dishes at room temperature. 2 ml of KM medium containing 1.2% w/v SeaPlaque® agarose, and 2,4-D, Picloram, Dicamba or para-Chlorophenoxyacetic acid (pCPA) to give the correct plant growth regulator concentrations is added. The final protoplast density used is 0.54 million per ml. The agarose and protoplasts are mixed well, and the medium allowed to gel.

The dishes are cultured as described in example 10. After a period of 3 weeks, macroscopic colonies arising in the dishes are counted. The results are shown in Table 7.

TABLE 7

Colony formation from cultured protoplasts of Zea mays in the presence of various plant growth regulators (auxins) [number of colonies formed]

| auxin | Plant growth regulator concentration [mg/liter] | | | |
|---|---|---|---|---|
|  | 0 | 0.1 | 1 | 10 |
| 2,4-D | 0 | 140 | 0 | 0 |
| picloram | 0 | 6 | 101 | 7 |
| dicamba | 0 | 62 | 288 | 0 |
| pCPA | 0 | 52 | 0 | 0 |

Example 22

Construction of a deleted Bt protoxin gene containing approximately 725 amino acids, and construction of a chimeric gene containing this deleted gene with the CaMV 35S promoter.

Figure 11:
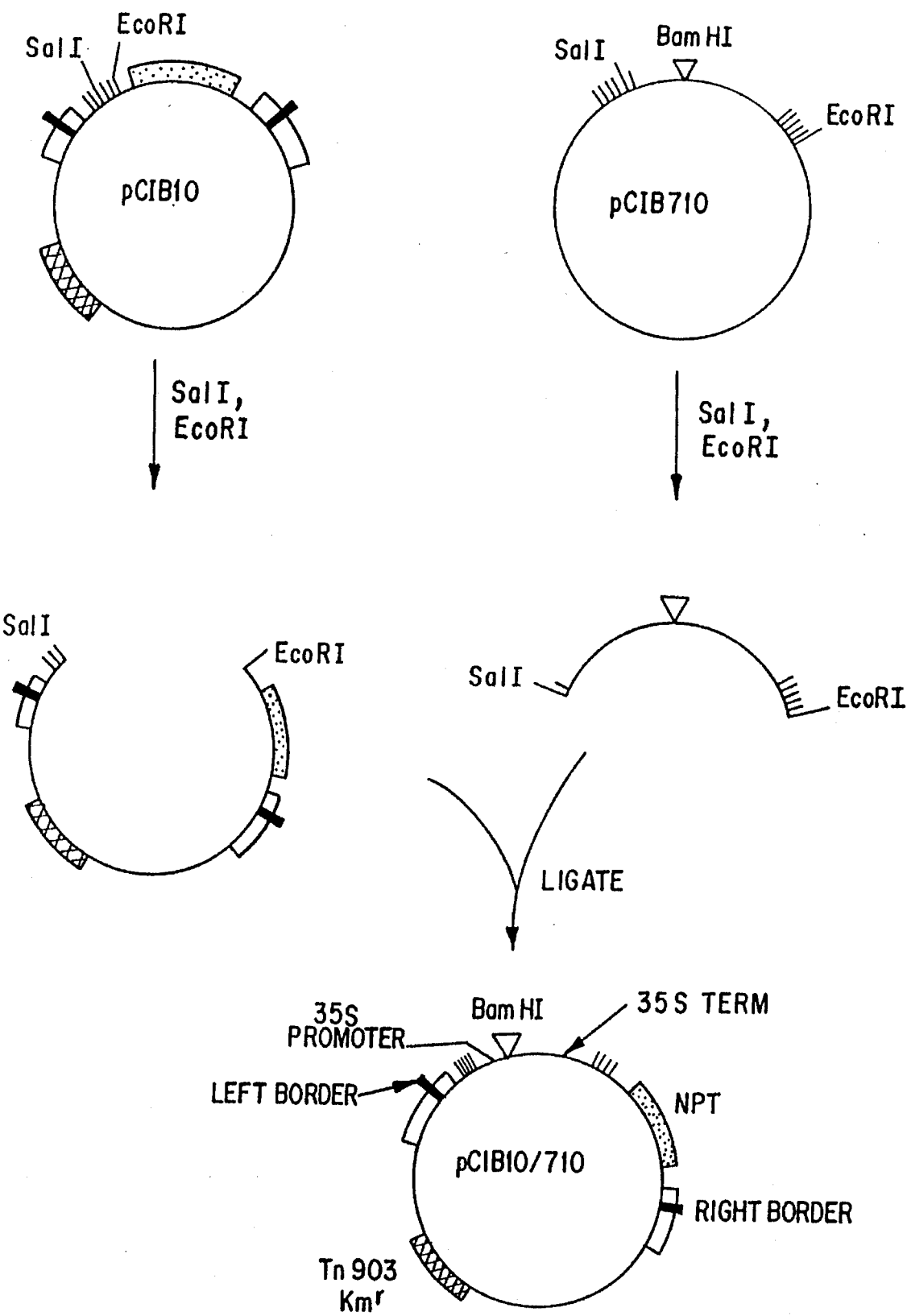
FIG. 11 shows the construction of plasmid pCIB10/710.
Figure 12:
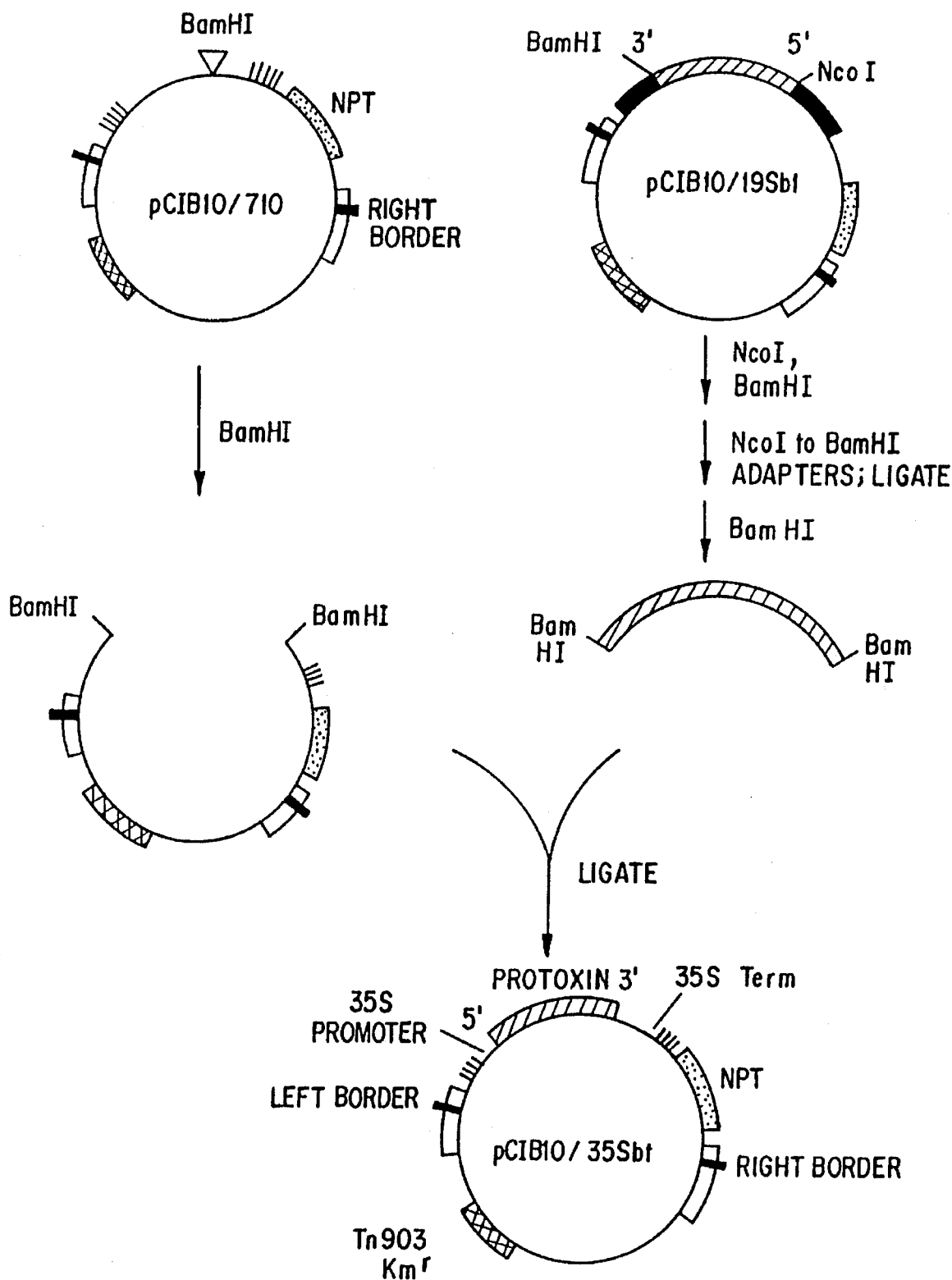
FIG. 12 shows the construction of plasmid pCIB10/35SBt.
Figure 14:
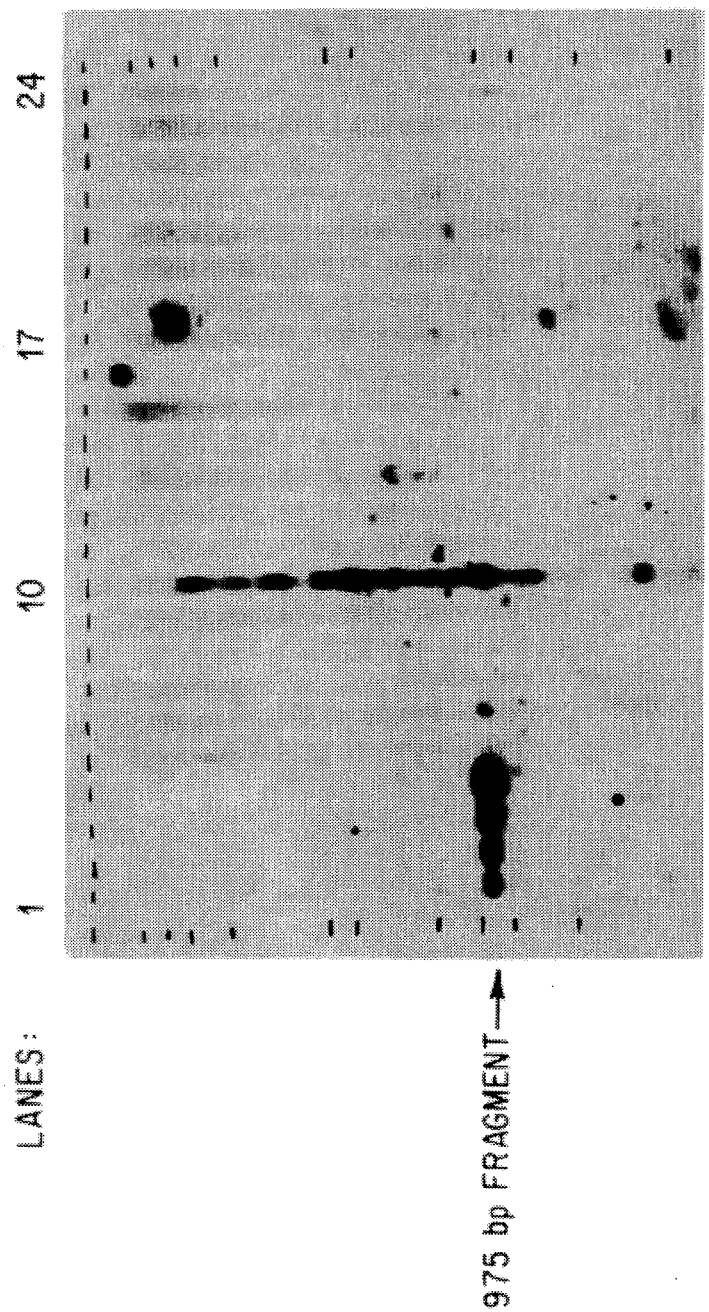
FIG. 14 shows the Southern blot analysis of different *Zea mays* calli recovered after transformation of *Zea mays* protoplasts with pCIB712, probed with the EcoRI fragment of pCIB712.

A deleted protoxin gene containing approximately 725 amino acids, is made by removing the COOH-terminal portion of the gene by cleaving at the KnpI restriction endonuclease site at position 2325 in the sequence shown in Formula I in FIG. 13. Plasmid pCIB10/35SBt (FIG. 12) is digested with BamHI and KnpI, and the approximately 2.2-kbp BamHI/KnpI fragment containing the deleted protoxin gene is isolated by preparative agarose gel electrophoresis. To convert the KnpI site at the 3' end to a BamHI site, the fragment is mixed with a KnpI/BamHI adapter oligonucleotide and ligated. This fragment is then mixed with BamHI-cleaved pCIB10/710 (FIG. 11). The resulting transformants, designed pCIB10/35SBt (KnpI) and shown in FIG. 15, contain the deleted protoxin gene of approximately 725 amino acids. These transformants are selected on kanamycin.

Example 23

Construction of a deleted Bt protoxin gene containing approximately 645 amino acids, and construction of a chimeric gene containing this deleted gene with the CaMV 35S promoter.

A deleted protoxin gene containing approximately 645 amino acids is made by removing the COOH-terminal portion of the gene by cleaving at the BClI restriction endonuclease site at the position 2090 in the sequence shown in Formula I in FIG. 13. Plasmid pCIB10/35SBt (FIG. 12) is digested with BamHI and BclI, and the approximately 1.9-kbp BamHI/BclI fragment containing the deleted protoxin gene is isolated by preparative agarose gel electrophoresis. Since BclI creates a cohesive end compatible with BamHI, no further manipulation is required prior to ligating this fragment into BamHI-cleaved pCIB10/710 (FIG. 11). The resulting plasmid, which has the structure pCIB10/35SBt(BclI) shown in FIG. 16, is selected on kanamycin.

Example 24

Construction of a deleted Bt protoxin gene containing approximately 607 amino acids, and construction of a chimeric gene containing this deleted gene with the CaMV 35S promoter.

A deleted protoxin gene is made by introducing a BamHI cleavage site (GGATCC) following nucleotide 1976 in the sequence shown in Formula I (FIG. 13). This is done by cloning the BamHI fragment containing the protoxin sequence from pCIB10/35SBt into mp18, and using standard oligonucleotide mutagenesis procedures described above. After mutagenesis, double-stranded replicative DNA is prepared from the M13 clone, which is then digested with BamHI. The approximately 1.9-kbp fragment containing the deleted protoxin gene is inserted into BamHI-cleaved pCIB10/710. The resulting plasmid, which has the structure pCIB10/35SBt(607) is shown in FIG. 17, is selected for on kanamycin.

What is claimed is:

1. A method of controlling insect larvae comprising:
   (a) feeding the larvae an insecticidal amount of transgenic Zea mays cells containing an isolated or synthetic DNA which encodes a polypeptide having the insect toxicity properties of a Bacillus thuringiensis crystal protein, wherein the cells have been grown or cultured in a manner to permit expression of the toxin in the cells.

2. The method of claim 1, wherein said cells comprise a part of a fertile Zea mays plant.

3. The method of claim 1 wherein said DNA is synthetic DNA.

4. The method of claim 1 wherein said DNA is isolated DNA.

* * * * *